(12) United States Patent
Corcoran, Jr. et al.

(10) Patent No.: US 9,738,539 B2
(45) Date of Patent: *Aug. 22, 2017

(54) SEPARATION AND STORAGE OF FLUIDS USING ITQ-55

(71) Applicant: ExxonMobil Research and Engineering Company, Annandale, NJ (US)

(72) Inventors: Edward W. Corcoran, Jr., Easton, PA (US); Pavel Kortunov, Flemington, NJ (US); Charanjit S. Paur, Phillipsburg, NJ (US); Peter I. Ravikovitch, Princeton, NJ (US); Yu Wang, Lebanon, NJ (US); Avelino Corma Canos, Valencia (ES); Fernando Rey Garcia, Valencia (ES); Susana Valencia Valencia, Valencia (ES); Angel Cantín Sanz, Valencia (ES); Miguel Palomino Roca, Valencia (ES)

(73) Assignee: ExxonMobil Research and Engineering Company, Annandale, NJ (US)

(*) Notice: Subject to any disclaimer, the term of this patent is extended or adjusted under 35 U.S.C. 154(b) by 6 days.

This patent is subject to a terminal disclaimer.

(21) Appl. No.: 14/744,485

(22) Filed: Jun. 19, 2015

(65) Prior Publication Data

US 2016/0008753 A1    Jan. 14, 2016

(30) Foreign Application Priority Data

Jun. 20, 2014    (ES) .................................. 201430935

(51) Int. Cl.
*C01B 39/48* (2006.01)
*B01J 20/18* (2006.01)
(Continued)

(52) U.S. Cl.
CPC .............. *C01B 39/48* (2013.01); *B01D 53/02* (2013.01); *B01D 53/04* (2013.01); *B01D 53/047* (2013.01); *B01D 53/0407* (2013.01); *B01D 53/0462* (2013.01); *B01D 53/228* (2013.01); *B01D 53/229* (2013.01); *B01D 71/028* (2013.01); *B01J 20/18* (2013.01); *B01J 20/3078* (2013.01); *B01J 29/70* (2013.01); *C01B 3/508* (2013.01); *C01B 17/167* (2013.01);
(Continued)

(58) Field of Classification Search
CPC ...... B01D 71/028; B01D 53/02; B01D 53/04; B01D 53/0407; B01D 53/047; B01D 53/0462; B01D 53/228; B01D 53/229; B01D 2257/302; B01D 2257/304; B01D 2257/40; B01D 2257/404; B01D 2257/406; B01D 2257/50; B01D 2257/504; B01D 2257/70; B01D 2257/702; B01D 2257/7022; B01D 2257/80; B01D 2256/10; B01D 2256/12; B01D 2256/16; B01D 2256/18; B01D 2256/20; B01D 2256/22; B01D 2256/24; B01D 2256/245; B01D 2256/26; B01D 2253/108; B01J 20/18; B01J 20/3078; B01J 29/70; C01C 1/12; Y02C 10/08; C01B 17/167; C01B 21/0466; C01B 2210/0018; C01B 37/002; C01B 37/007; C01B 37/02; C01B 39/06; C01B 39/08; C01B 39/12; C01B 39/48; C01B 3/508; C07C 1/20; C07C 1/322; C07C 2259/70; C07C 2259/76; C07C 2259/78; C07C 29/00; C07C 2/76; C07C 41/01
USPC ..... 95/90, 95, 127, 131, 132, 139, 141, 143, 95/144; 206/0.7; 423/210
See application file for complete search history.

(56) References Cited

U.S. PATENT DOCUMENTS

| | | |
|---|---|---|
| 5,871,650 A | 2/1999 | Lai et al. |
| 6,734,129 B2 | 5/2004 | Lai et al. |

(Continued)

FOREIGN PATENT DOCUMENTS

| | | |
|---|---|---|
| CA | 2306311 A1 | 10/2001 |
| WO | 2013156638 A1 | 10/2013 |
| WO | 2014122344 A1 | 8/2014 |

OTHER PUBLICATIONS

Jiang et al., "ITQ-54: a multi-dimensional extra-large pore zeolite with 20×14×12-ring channels", Chemical Science, Jan. 1, 2015, pp. 480-485, vol. 6, iss. 1, Royal Society of Chemistry.

(Continued)

*Primary Examiner* — Frank Lawrence
(74) *Attorney, Agent, or Firm* — Andrew T. Ward

(57) ABSTRACT

This invention refers to a microporous crystalline material of zeolitic nature that has, in its calcined state and in the absence of defects in its crystalline matrix manifested by the presence of silanols, the empirical formula

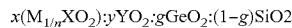
$x(M_{1/n}XO_2) \cdot yYO_2 \cdot gGeO_2 \cdot (1-g)SiO2$ in which
M is selected between $H^+$, at least one inorganic cation of charge +n, and a mixture of both,
X is at least one chemical element of oxidation state +3,
Y is at least one chemical element with oxidation state +4 different from Si,
x takes a value between 0 and 0.2, both included,
y takes a value between 0 and 0.1, both included,
g takes a value between 0 and 0.5, both included
that has been denoted ITQ-55, as well as a method for its preparation. This invention also relates to uses of the crystalline material of zeolitic nature for adsorption of fluid (Continued)

components, membrane separation of fluid components, storage of fluid components, and catalysis of various conversion reactions.

47 Claims, 28 Drawing Sheets

(51) Int. Cl.

| | |
|---|---|
| B01J 29/70 | (2006.01) |
| B01D 71/02 | (2006.01) |
| B01D 53/04 | (2006.01) |
| B01D 53/047 | (2006.01) |
| C01B 3/50 | (2006.01) |
| B01D 53/02 | (2006.01) |
| B01D 53/22 | (2006.01) |
| C01B 17/16 | (2006.01) |
| C01B 21/04 | (2006.01) |
| C01C 1/12 | (2006.01) |
| B01J 20/30 | (2006.01) |
| C07C 1/20 | (2006.01) |
| C07C 1/32 | (2006.01) |
| C07C 2/76 | (2006.01) |
| C07C 29/00 | (2006.01) |
| C07C 41/01 | (2006.01) |
| C01B 39/06 | (2006.01) |
| C01B 39/08 | (2006.01) |
| C01B 37/00 | (2006.01) |
| C01B 37/02 | (2006.01) |
| C01B 39/12 | (2006.01) |

(52) U.S. Cl.
CPC ........ *C01B 21/0466* (2013.01); *C01B 37/002* (2013.01); *C01B 37/007* (2013.01); *C01B 37/02* (2013.01); *C01B 39/06* (2013.01); *C01B 39/08* (2013.01); *C01B 39/12* (2013.01); *C01C 1/12* (2013.01); *C07C 1/20* (2013.01); *C07C 1/322* (2013.01); *C07C 2/76* (2013.01); *C07C 29/00* (2013.01); *C07C 41/01* (2013.01); *B01D 2253/108* (2013.01); *B01D 2256/10* (2013.01); *B01D 2256/12* (2013.01); *B01D 2256/16* (2013.01); *B01D 2256/18* (2013.01); *B01D 2256/20* (2013.01); *B01D 2256/22* (2013.01); *B01D 2256/24* (2013.01); *B01D 2256/245* (2013.01); *B01D 2256/26* (2013.01); *B01D 2257/302* (2013.01); *B01D 2257/304* (2013.01); *B01D 2257/40* (2013.01); *B01D 2257/404* (2013.01); *B01D 2257/406* (2013.01); *B01D 2257/50* (2013.01); *B01D 2257/504* (2013.01); *B01D 2257/70* (2013.01); *B01D 2257/702* (2013.01); *B01D 2257/7022* (2013.01); *B01D 2257/80* (2013.01); *C01B 2203/0405* (2013.01); *C01B 2210/0018* (2013.01); *C07C 2529/70* (2013.01); *C07C 2529/76* (2013.01); *C07C 2529/78* (2013.01); *Y02C 10/08* (2013.01)

(56) References Cited

U.S. PATENT DOCUMENTS

| | | |
|---|---|---|
| 7,049,259 B1 | 5/2006 | Deckman et al. |
| 7,094,275 B2 | 8/2006 | Keefer et al. |
| 7,476,635 B2 | 1/2009 | Chau et al. |
| 7,498,011 B2 | 3/2009 | Cao et al. |
| 7,828,875 B2 | 11/2010 | Li et al. |
| 7,959,720 B2 | 6/2011 | Deckman et al. |
| 8,002,880 B2 | 8/2011 | Carruthers |
| 8,067,327 B2 | 11/2011 | Li et al. |
| 8,529,664 B2 | 9/2013 | Deckman et al. |
| 8,603,432 B2 | 12/2013 | Andersen et al. |
| 8,641,810 B2 | 2/2014 | McAlister |
| 2006/0169142 A1 | 8/2006 | Rode et al. |
| 2006/0189476 A1 | 8/2006 | Deckman et al. |
| 2006/0252631 A1 | 11/2006 | Deckman et al. |
| 2009/0111959 A1 | 4/2009 | Cao et al. |
| 2009/0202416 A1* | 8/2009 | Corma Canos ........ B01D 15/00 423/351 |
| 2012/0133939 A1* | 5/2012 | Yaghi ...................... B01D 53/02 356/402 |
| 2015/0011815 A1 | 1/2015 | Ma et al. |

OTHER PUBLICATIONS

International Search Report with Written Opinion from PCT/US2015/036584 dated Jun. 19, 2015.
International Search Report with Written Opinion from PCT/US2015/036601 dated Jun. 19, 2015.
International Search Report with Written Opinion from PCT/US2015/036598 dated Jun. 19, 2015.
International Search Report with Written Opinion from PCT/US2015/036647 dated Jun. 19, 2015.
International Search Report with Written Opinion from PCT/US2015/036636 dated Jun. 19, 2015.
Broach et al., "Zeolites", Ullmann's Encyclopedia of Industrial Chemistry, pp. 1-35, 2012, Wiley-VCH Verlag GmbH & Co. KGaA, Weinheim.
Park et al., "Effects of cage shape and size of 8-membered ring molecular sieves on their deactivation in methanol-to-olefin (MTO) reactions", Applied Catalysis A: General, Jan. 17, 2008, pp. 36-44, vol. 339, Science Direct, Elsevier.
Anderson et al., "The crystal structure of lithium hydrazinium flouroberyllate", Acta Crystallographica Section B, Structural Science B, Crystal Engineering and Materials, Nov. 1973, pp. 2625-2627, vol. 29, iss. 11, Wiley Online Library.
Meier, et al., "The Topology of Three-Dimensional 4-Connected Nets: Classification of Zeolite Framework Types Using Coordination Sequences", Journal of Solid State Chemistry, Mar. 1979, pp. 349-355, vol. 27, iss. 3, Science Direct.
Reyes et al.,"Frequency Modulation Methods for Diffusion and Adsorption Measurements in Porous Solids", Journal of Physical Chemistry B, Jan. 23, 1997, pp. 614-622, vol. 101, iss. 4, ACS Publications.
Koller et al., "Five-Coordinate Silicon in High-Silica Zeolites", Journal of American Chemical Society, Mar. 23, 1999, pp. 3368-3376, vol. 121, iss. 14, ACS Publications.
Sastre et al., "ZeoTsites: a code for topological and crystallographic tetrahedral sites analysis in zeolites and zeotypes", Microporous and Mesoporous Materials, Mar. 2001, pp. 27-40, vol. 43, iss. 1, ScienceDirect, Elsevier.
Tuel et al., "NMR Characterization and Rietveld Refinement of the Structure of Rehydrated AlPO 4—34", Journal of Physical Chemistry B, in J. Phys. Chem. B, May 26, 2000, pp. 5697-5705, vol. 104, iss. 24, ACS Publications.
Serre et al., "Hydrothermal synthesis, structure determination from powder data of a three-dimensional zirconium diphosphonate with an exceptionally high thermal stability: Zr(O3P-(CH2)-PO3) or MIL-57", Journal of Materials Chemistry, Jun. 12, 2002, pp. 2367-2369, vol. 12, The Royal Society of Chemistry.
Zheng, "Microporous and Photoluminescent Chalcogenide Zeolite Analogs" Science, Dec. 20, 2002, pp. 2366-2369, vol. 298, AAAS, HighWirePress.
Huang et al., "Ligand-Directed Strategy for Zeolite-Type Metal—Organic Frameworks: Zinc(II) Imidazolates with Unusual Zeolitic Topologies", Angewandte Chemie International Edition, Jan. 27, 2006, pp. 1557-1559, vol. 45, iss. 10, Wiley Online Library.

* cited by examiner

Framework Structure of ITQ-55 showing only the tetrahedral atoms. There is a single unit cell, whose edges are defined by the gray box.

SEPARATION AND STORAGE OF FLUIDS USING ITQ-55

CLAIM OF FOREIGN PRIORITY

Pursuant to 35 U.S.C. 119(a), this application claims the benefit of Application No. P201430935 filed in Spain, reception office OEPM Madrid, on Jun. 20, 2014.

CROSS-REFERENCE TO RELATED APPLICATIONS

This application is related to four other co-pending U.S. applications, filed on Jun. 19, 2015 as follows: Ser. No. 14/744,169; Ser. No. 14/744,334; Ser. No. 14/744,248; and Ser. No. 14/744,211. Each of these co-pending U.S. applications are hereby incorporated by reference herein in their entirety.

FIELD OF THE INVENTION

This invention belongs to the technical field of microporous crystalline materials of zeolitic nature, useful as adsorbents, catalysts or catalytic components, for transformation processes and in particular for the adsorption and separation of organic and inorganic compound in gas or liquid phase.

BACKGROUND OF THE INVENTION

Zeolites are a microporous crystalline material formed by a matrix of TO4 tetrahedrons that share all their vertices giving rise to a three-dimensional structure that contains channels and/or cavities of molecular dimensions. They are of variable composition, and T generally represents atoms with formal oxidation state +3 or +4, such as for example Si, Ge, Ti, Al, B, or Ga. When some of the T atoms have an oxidation state less than +4, the crystalline matrix formed presents negative charges that are compensated by means of the presence in the channels or cavities of organic or inorganic cations. These channels and cavities may also contain organic molecules and $H_2O$, therefore, in a general manner, the chemical composition of the zeolites may be represented by means of the following empirical formula:

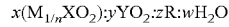

$$x(M_{1/n}XO_2):yYO_2:zR:wH_2O$$

where M is one or several organic or inorganic cations of charge +n; X is one or several trivalent elements; Y is one or several tetravalent elements, generally Si; and R is one or several organic substances. Although by means of postsynthesis treatments the nature of M, X, Y and R and the values of x, y, z, and w may vary, the chemical composition of a zeolite (just as is synthesized or after its calcining) possesses a characteristic range for each zeolite and its method of preparation.

The crystalline structure of each zeolite, with a system of channels and specific cavities, gives rise to a characteristic diffraction pattern of X-rays, which allows one to differentiate them from each other.

Many zeolites have been synthesized in presence of an organic molecule that acts as a structure director agent. The organic molecules that act as structure director agents (SDA) generally contain nitrogen in their composition, and they can give rise to stable organic cations in the reaction medium.

The mobilization of the precursor species during the zeolites synthesis may be carried out in the presence of hydroxyl groups and basic medium that can be introduced as hydroxide of the same SDA, such as for example tetrapropylammonium hydroxide in the case of the zeolite ZSM-5. The fluoride ions can also act as mobilizing agents in synthesis of zeolites, for example in the patent EP-TO-337479 the use of HF is described in $H_2O$ at low pH as a mobilizing agent of silica for the zeolite ZSM-5 synthesis.

SUMMARY OF THE INVENTION

This invention refers to a new microporous crystalline material of zeolitic nature, identified as "zeolite ITQ-55," its preparation method and its use.

ITQ-55 (INSTITUTO DE TECNOLOGÍA QUÍMICA number 55) is a new crystalline microporous material having a framework of tetrahedral atoms connected by bridging atoms, the tetrahedral atom framework being defined by the interconnections between the tetrahedrally coordinated atoms in its framework. ITQ-55 is stable to calcination in air, absorbs hydrocarbons, and is catalytically active for hydrocarbon conversion.

This material, both in its calcined form and synthesized without calcining has an X-ray diffraction pattern that is different from other well-known zeolitic material and, therefore, is characteristic of this material.

In various aspects, the material is suitable for use in separations based on selective adsorption of fluid components. In various aspects, the material is suitable for use in membrane separations of fluid components. In various aspects, the material is suitable for use for storage of a fluid component. In various aspects, the material is suitable for use in catalyzing conversion reactions of organic compounds and/or syngas.

DETAILED DESCRIPTION OF THE EMBODIMENTS

Figure 1:
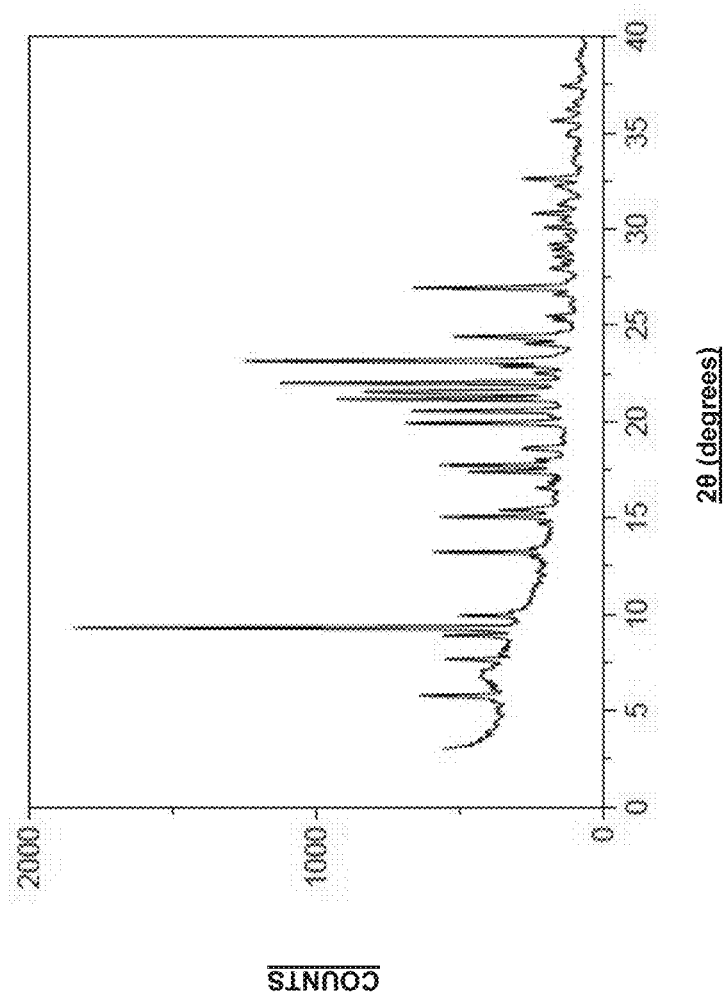
FIG. 1 represents the X-ray diffraction pattern of the most characteristic peaks of the purely siliceous ITQ-55 material, as is synthesized, obtained according to Example 2.

This invention refers in the first place to a microporous crystalline material of zeolitic nature that has, in calcined state and in absence of defects in its crystalline matrix manifested by the presence of silanols, the empirical formula

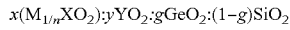

$x(M_{1/n}XO_2):yYO_2:gGeO_2:(1-g)SiO_2$ in which,

M is selected among H+, at least one inorganic cation of charge +n, and a mixture of both, preferably selected among H+, at least one inorganic cation of charge +n selected among alkaline, alkaline-earth metals and combinations thereof, and a mixture of both, X is at least one chemical element of oxidation state +3, selected preferably between Al, Ga, B, Fe, Cr and mixtures of the same.

Y is at least one chemical element with oxidation state +4 different from Si, selected preferably between Ti, Sn, Zr, V and mixtures of the same.

x takes a value between 0 and 0.2, both included, preferably less than 0.1.

y takes a value between 0 and 0.1, both included, preferably less than 0.05.

g takes a value between 0 and 0.5, both included, preferably less than 0.33.

and because the material, as it is synthesized, has an X-ray diffraction pattern with, at least, the angle values 2θ (degrees) and relative intensities ($I/I_0$) shown in the Table I, $I_0$ being the intensity of the highest peak to which is assigned a value of 100:

TABLE I

| 2θ (degrees) ± 0.5 | Intensity ($I/I_0$) |
|---|---|
| 5.8 | w |
| 7.7 | w |
| 8.9 | w |
| 9.3 | mf |
| 9.9 | w |
| 10.1 | w |
| 13.2 | m |
| 13.4 | w |
| 14.7 | w |
| 15.1 | m |
| 15.4 | w |
| 15.5 | w |
| 17.4 | m |
| 17.7 | m |
| 19.9 | m |
| 20.6 | m |
| 21.2 | f |
| 21.6 | f |
| 22.0 | f |
| 23.1 | mf |
| 24.4 | m |
| 27.0 | m | where w is a relative weak intensity between 0 and 20%, m is an relative medium intensity between 20 and 40%, f is a relative strong intensity between 40 and 60%, and mf is a very strong relative intensity between 60 and 100%.

The microporous crystalline material of zeolitic nature according to the invention, after being calcined to eliminate the organic compounds occluded in its interior, possesses an X-ray diffraction pattern with, at least, the angle values 2θ (degrees) and relative intensities ($I/I_0$) indicated in the Table II:

TABLE II

| 2θ (degrees) ± 0.5 | Intensity ($I/I_0$) |
|---|---|
| 6.2 | w |
| 7.8 | w |
| 8.0 | w |
| 9.8 | mf |
| 10.0 | m |
| 10.3 | w |
| 12.3 | w |
| 13.4 | w |
| 13.7 | w |
| 15.0 | w |
| 15.2 | w |
| 16.8 | w |
| 18.1 | w |
| 20.1 | w |
| 21.3 | w |
| 23.5 | w |
| 23.9 | w |
| 26.8 | w | where w, m, f and mf have the previous meaning.

According to a preferred embodiment of this invention the microporous crystalline material of zeoltic nature ITQ-55, has, in calcined state and in absence of defects in its crystalline matrix manifested by the presence of silanols, the empirical formula

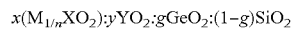

in which
M is selected among $H^+$, at least one inorganic cation of charge +n, preferably alkaline or alkaline earth, alkaline, alkaline-earth metals and combinations of the same,
X is at least one chemical element of oxidation state +3, selected between Al, Ga, B, Fe, Cr and mixtures of the same,
Y is at least one chemical element with oxidation state +4 different from Si, selected among Ti, Sn, V, Zr and mixtures of the same,
x takes a value between 0 and 0.1, both included,
y takes a value between 0 and 0.05, both included,
g takes a value between 0 and 0.33, both included,
and the material, as is synthesized, has an X-ray diffraction pattern with at least, the angle values 2θ (degrees) and relative intensities mentioned previously (Table I) and this material in calcined state has an X-ray diffraction pattern with, at least, the angle values 2θ (degrees) and relative intensities ($I/I_0$) mentioned previously (Table II).

According to a preferred embodiment of this invention the microporous crystalline material of zeolitic nature ITQ-55 is a pure silica material, that is to say that in the general formula indicated previously "x", "y" and "g" they take the value 0.

According to another preferred embodiment of this invention the microporous crystalline material of zeolitic nature ITQ-55 is a material that can have in the general formula previously indicated "x" equal to 0, "y" equal to 0 and "g" different from 0.

According to another preferred embodiment of this invention the microporous crystalline material of zeolitic nature ITQ-55 is a material in whose general formula:
X is selected between Al, Ga, B, Fe, Cr, and combinations of the same,
y takes the value 0, and
g takes the value 0.

Another preferred embodiment of this invention the microporous crystalline material of zeolitic nature ITQ-55 is a material, which can have in its general formula:
Y is selected between Ti, Zr, Sn, and combinations of the same,
x takes the value 0, and
g takes the value 0.

According to another preferred embodiment the microporous crystalline material of zeolitic nature ITQ-55 is a material in whose general formula:
X is Al, Ga, Fe, Cr, and combinations of the same,
Y is Ti, Zr, Sn, and combinations of the same and
g take the value 0.

In one particular embodiment, the microporous crystalline material of zeolitic nature ITQ-55 is a material in whose general formula:
X is Al, Ga. B, Fe, Cr, and combinations of the same,
y takes the value 0, and
g takes a value different from 0 and less than 0.33.

Another particular embodiment describes the microporous crystalline material of zeolitic nature ITQ-55 in whose general formula:
Y is Ti, Zr, Sn, and combinations of the same,
x takes the value 0, and
g takes a value different from 0 and less than 0.33.

In another particular embodiment, the microporous crystalline material of zeolitic nature ITQ-55 is a material in whose general formula:
X is Al, Ga, B, Fe, Cr, and combinations of the same,
Y is Ti, Zr or Sn, and
g takes a value different from 0 and less than 0.33.

The X-ray diffraction patterns of the ITQ-55 material has been obtained by the powder method using a fixed divergence slit of ⅛° and using the Kα radiation of Cu. It should be kept in mind that the diffraction data listed for this zeolite sample ITQ-55 as single or unique lines, can be formed from multiple overlapping reflections that, under certain conditions, such as differences in crystallographic changes, may appear as resolved or partially resolved lines. Generally, the crystallographic changes may include small variations in the parameters of the unit cell and/or changes in the symmetry of the unit cell, without a change taking place in the structure. Thus, the positions, widths and relative intensities of the peaks depend in a certain measure on the chemical composition of the material, as well as of the degree of hydration and the crystal size.

In particular, when the matrix is composed exclusively by silicon oxide and has been synthesized in the presence of fluoride anions using the quaternary cation diammonium $N^2,N^2,N^2,N^5,N^5,N^5,3a,6a$-octamethylo-octahydropentalene-2,5-diammonium as structure director agent, the ITQ-55 zeolite as synthesized presents an X-ray diffraction pattern like the one that is shown in FIG. 1. This diagram is characterized by the angle values 2θ (degrees) and relative intensities ($I/I_0$) that are presented in Table III, where w, m, f and mf have the same meaning as in the Table I.

TABLE III

| 2θ (degrees) ± 0.5 | Intensity ($I/I_0$) |
|---|---|
| 5.78 | w |
| 7.68 | w |
| 8.91 | w |
| 9.31 | mf |
| 9.93 | w |
| 10.14 | w |
| 13.23 | m |
| 13.42 | w |
| 14.70 | w |
| 15.06 | m |
| 15.40 | w |
| 15.52 | w |
| 16.55 | w |
| 16.84 | w |
| 17.05 | w |
| 17.40 | m |
| 17.73 | m |
| 18.02 | w |
| 18.60 | w |
| 19.93 | m |
| 20.56 | m |
| 21.17 | f |
| 21.47 | m |
| 21.56 | f |
| 22.01 | f |
| 22.51 | w |
| 22.88 | w |
| 23.14 | mf |
| 24.05 | w |
| 24.42 | m |
| 24.62 | w |
| 25.28 | w |
| 25.49 | w |
| 26.61 | w |
| 26.95 | m |
| 27.95 | w |
| 28.24 | w |
| 28.59 | w |
| 28.93 | w |
| 29.21 | w |
| 29.68 | w |

Figure 2:
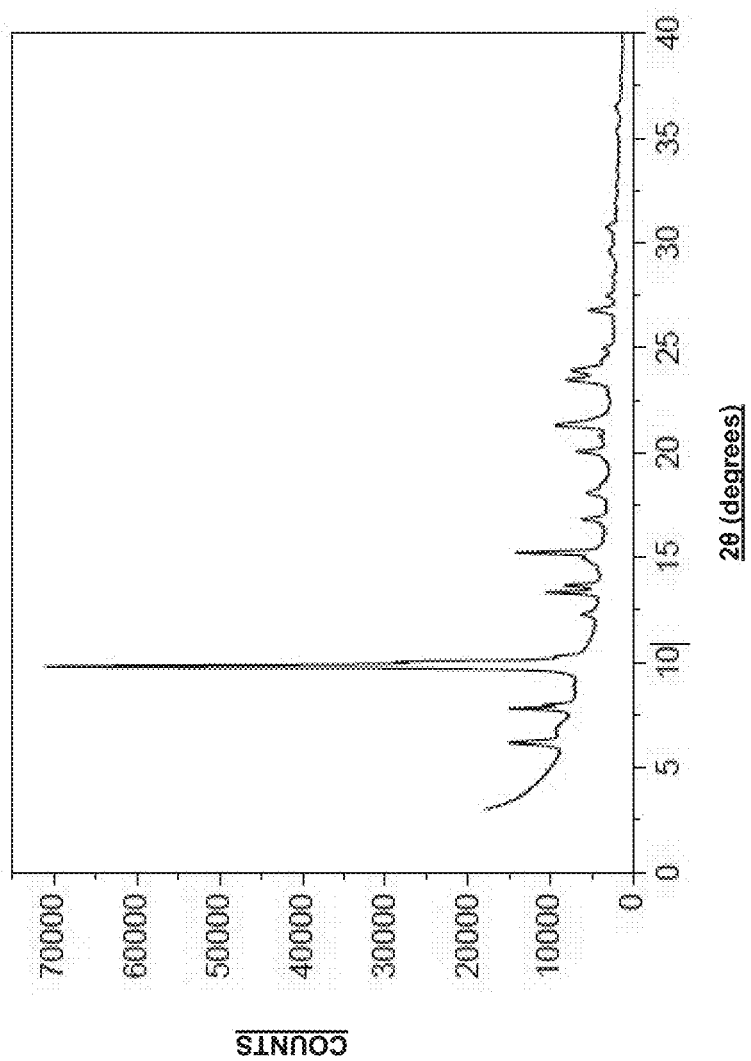
FIG. 2 represents the X-ray diffraction pattern of the most characteristic peaks of the material of the example 2 in calcined state.

The X-ray diffraction pattern of the previous sample of ITQ-55 after being calcined at 800° C. to eliminate the organic compounds occluded in its interior is shown in the FIG. 2. This diffractogram is characterized by the angle values 2θ (degrees) and relative intensities (I/I$_0$) that are shown in the Table IV, where w, m, f and mf have the same meanings as in Table I. The comparison of the diffractograms of X-rays corresponding to zeolite ITQ-55 as is synthesized and in calcined state show that the material is thermally stable.

TABLE IV

| 2θ (degrees) | Intensity (I/I$_0$) |
|---|---|
| 6.18 | w |
| 7.80 | w |
| 7.98 | w |
| 9.82 | mf |
| 10.02 | m |
| 10.29 | w |
| 12.31 | w |
| 13.35 | w |
| 13.68 | w |
| 14.98 | w |
| 15.22 | w |
| 15.52 | w |
| 16.82 | w |
| 18.09 | w |
| 18.43 | w |
| 20.06 | w |
| 20.81 | w |
| 21.34 | w |
| 21.67 | w |
| 23.45 | w |
| 23.92 | w |
| 24.39 | w |
| 24.99 | w |
| 26.80 | w |
| 27.48 | w |
| 27.91 | w |
| 28.43 | w |
| 29.61 | w |

As with any porous crystalline material, the structure of ITQ-55 can be defined not only by its X-ray diffraction pattern but by its framework structure, i.e., the interconnections between the tetrahedrally coordinated atoms in its framework. In particular, ITQ-55 has a framework of tetrahedral (T) atoms connected by bridging atoms, wherein the tetrahedral atom framework is defined by connecting the nearest tetrahedral (T) atoms in the manner given in Table V.

TABLE V

ITQ-55 tetrahedral atom interconnections

| T atom | Connected to: |
|---|---|
| T1 | T6, T7, T55, T73 |
| T2 | T3, T5, T9, T56 |
| T3 | T2, T7, T21, T27 |
| T4 | T8, T9, T58, T73 |
| T5 | T2, T8, T52, T59 |
| T6 | T1, T8, T53, T60 |
| T7 | T1, T3, T50, T61 |
| T8 | T4, T5, T6, T51 |
| T9 | T2, T4, T21, T63 |
| T10 | T15, T16, T64, T74 |
| T11 | T12, T14, T18, T65 |
| T12 | T11, T16, T30, T36 |
| T13 | T17, T18, T67, T74 |
| T14 | T11, T17, T43, T68 |
| T15 | T10, T17, T44, T69 |
| T16 | T10, T12, T41, T70 |
| T17 | T13, T14, T15, T42 |
| T18 | T11, T13, T30, T72 |
| T19 | T24, T25, T37, T73 |
| T20 | T21, T23, T27, T38 |
| T21 | T3, T9, T20, T25 |
| T22 | T26, T27, T40, T73 |
| T23 | T20, T26, T41, T70 |
| T24 | T19, T26, T42, T71 |
| T25 | T19, T21, T43, T68 |
| T26 | T22, T23, T24, T69 |
| T27 | T3, T20, T22, T45 |
| T28 | T33, T34, T46, T74 |
| T29 | T30, T32, T36, T47 |
| T30 | T12, T18, T29, T34 |
| T31 | T35, T36, T49, T74 |
| T32 | T29, T35, T50, T61 |
| T33 | T28, T35, T51, T62 |
| T34 | T28, T30, T52, T59 |
| T35 | T31, T32, T33, T60 |
| T36 | T12, T29, T31, T54 |
| T37 | T19, T42, T43, T75 |
| T38 | T20, T39, T41, T45 |
| T39 | T38, T43, T57, T63 |
| T40 | T22, T44, T45, T75 |
| T44 | T16, T23, T38, T44 |
| T42 | T17, T24, T37, T44 |
| T43 | T14, T25, T37, T39 |
| T44 | T15, T40, T41, T42 |
| T45 | T27, T38, T40, T57 |
| T46 | T28, T51, T52, T76 |
| T47 | T29, T48, T50, T54 |
| T48 | T47, T52, T66, T72 |
| T49 | T31, T53, T54, T76 |
| T50 | T7, T32, T47, T53 |
| T51 | T8, T33, T46, T53 |
| T52 | T5, T34, T46, T48 |
| T53 | T6, T49, T50, T51 |
| T54 | T36, T47, T49, T66 |
| T55 | T1, T60, T61, T75 |
| T56 | T2, T57, T59, T63 |
| T57 | T39, T45, T56, T61 |
| T58 | T4, T62, T63, T75 |
| T59 | T5, T34, T56, T62 |
| T60 | T6, T35, T55, T62 |
| T61 | T7, T32, T55, T57 |
| T62 | T33, T58, T59, T60 |
| T63 | T9, T39, T56, T58 |
| T64 | T10, T69, T70, T76 |
| T65 | T11, T66, T68, T72 |
| T66 | T48, T54, T65, T70 |
| T67 | T13, T71, T72, T76 |
| T68 | T14, T25, T65, T71 |
| T69 | T15, T26, T64, T71 |
| T70 | T16, T23, T64, T66 |
| T71 | T24, T67, T68, T69 |
| T72 | T18, T48, T65, T67 |
| T73 | T1, T4, T19, T22 |
| T74 | T10, T13, T28, T31 |
| T75 | T37, T40, T55, T58 |
| T76 | T46, T49, T64, T67 |

Tetrahedral atoms are those capable of having tetrahedral coordination, including one or more of, but not limiting, lithium, beryllium, boron, magnesium, aluminum, silicon, phosphorous, titanium, chromium, manganese, iron, cobalt, nickel, copper, zinc, zirconium, gallium, germanium, arsenic, indium, tin, and antimony.

The synthetic porous crystalline material of this invention, ITQ-55, is a crystalline phase which has a unique 1-dimensional channel system comprising 8-member rings of tetrahedrally coordinated atoms.

Figure 5:
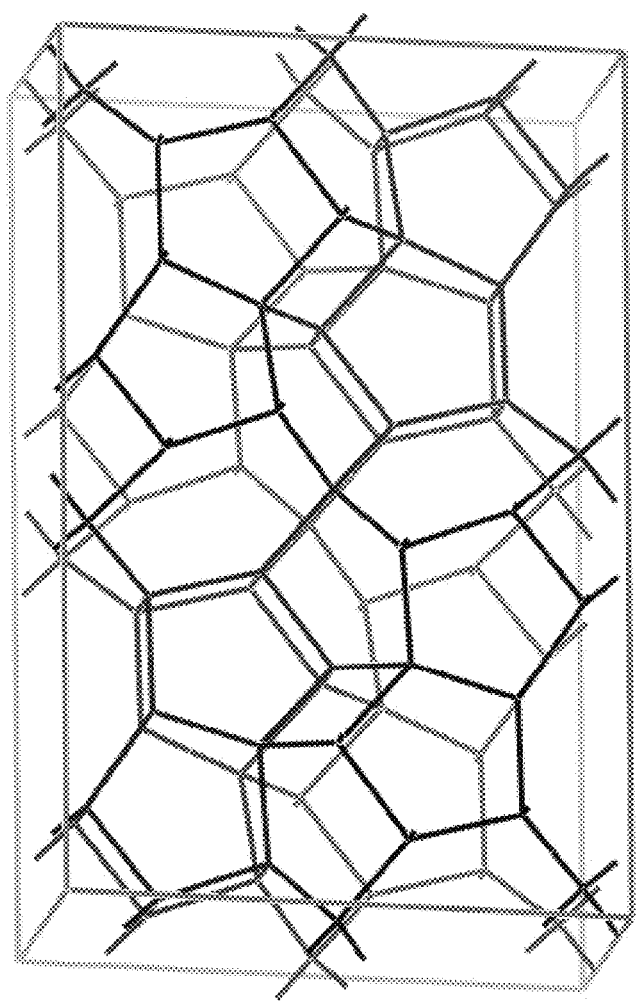
FIG. 5 represents the framework structure of ITQ-55 showing only the tetrahedral atoms.

In addition, to describing the structure of ITQ-55 by the interconnections of the tetrahedral atoms as in Table V above, it may be defined by its unit cell, which is the smallest repeating unit containing all the structural elements of the material. The pore structure of ITQ-55 is illustrated in FIG. 5 (which shows only the tetrahedral atoms) down the direction of the straight 10-membered ring channels. There is a single unit cell unit in FIG. 5, whose limits are defined by the box. Table VI lists the typical positions of each tetrahedral atom in the unit cell in units of Ångströms. Each tetrahedral atom is bonded to bridging atoms, which are also bonded to adjacent tetrahedral atoms. Tetrahedral atoms are those capable of having tetrahedral coordination, including one or more of, but not limiting, lithium, beryllium, boron, magnesium, aluminum, silicon, phosphorous, titanium, chromium, manganese, iron, cobalt, nickel, copper, zinc, zirconium, gallium, germanium, arsenic, indium, tin, and antimony. Bridging atoms are those capable of connecting two tetrahedral atoms, examples which include, but not limiting, oxygen, nitrogen, fluorine, sulfur, selenium, and carbon atoms.

TABLE VI

Positions of tetrahedral (T) atoms for the ITQ-55 structure. Values, in units of Ångströms, are approximate and are typical when T = silicon and the bridging atoms are oxygen.

| Atoms | x(Å) | y(Å) | z(Å) |
|---|---|---|---|
| T01 | 12.759 | 8.224 | 8.934 |
| T02 | 14.059 | 11.794 | 0.998 |
| T03 | 11.771 | 10.088 | 13.568 |
| T04 | 12.623 | 11.812 | 5.674 |
| T05 | 16.530 | 11.780 | 2.714 |
| T06 | 15.245 | 8.218 | 7.129 |
| T07 | 13.401 | 8.226 | 11.857 |
| T08 | 15.507 | 10.720 | 5.364 |
| T09 | 11.679 | 11.813 | 2.804 |
| T10 | 1.566 | 1.554 | 8.934 |
| T11 | 2.866 | 5.124 | 0.998 |
| T12 | 0.577 | 3.418 | 13.568 |
| T13 | 1.430 | 5.141 | 5.674 |
| T14 | 5.337 | 5.109 | 2.714 |
| T15 | 4.051 | 1.548 | 7.129 |
| T16 | 2.208 | 1.556 | 11.857 |
| T17 | 4.314 | 4.050 | 5.364 |
| T18 | 0.486 | 5.143 | 2.804 |
| T19 | 8.980 | 8.224 | 5.550 |
| T20 | 7.680 | 11.794 | 13.487 |
| T21 | 9.968 | 10.088 | 0.917 |
| T22 | 9.116 | 11.812 | 8.811 |
| T23 | 5.209 | 11.780 | 11.770 |
| T24 | 6.495 | 8.218 | 7.355 |
| T25 | 8.338 | 8.226 | 2.627 |
| T26 | 6.232 | 10.720 | 9.121 |
| T27 | 10.060 | 11.813 | 11.680 |
| T28 | 20.173 | 1.554 | 5.550 |
| T29 | 18.873 | 5.124 | 13.487 |
| T30 | 21.162 | 3.418 | 0.917 |
| T31 | 20.309 | 5.141 | 8.811 |
| T32 | 16.403 | 5.109 | 11.770 |
| T33 | 17.688 | 1.548 | 7.355 |
| T34 | 19.532 | 1.556 | 2.627 |
| T35 | 17.426 | 4.050 | 9.121 |
| T36 | 21.253 | 5.143 | 11.680 |
| T37 | 8.980 | 5.116 | 5.550 |
| T38 | 7.680 | 1.546 | 13.487 |
| T39 | 9.968 | 3.252 | 0.917 |
| T40 | 9.116 | 1.529 | 8.811 |
| T41 | 5.209 | 1.561 | 11.770 |
| T42 | 6.495 | 5.123 | 7.355 |
| T43 | 8.338 | 5.115 | 2.627 |
| T44 | 6.232 | 2.620 | 9.121 |
| T45 | 10.060 | 1.527 | 11.680 |
| T46 | 20.173 | 11.786 | 5.550 |
| T47 | 18.873 | 8.216 | 13.487 |
| T48 | 21.162 | 9.923 | 0.917 |
| T49 | 20.309 | 8.199 | 8.811 |
| T50 | 16.403 | 8.231 | 11.770 |
| T51 | 17.688 | 11.793 | 7.355 |
| T52 | 19.532 | 11.785 | 2.627 |
| T53 | 17.426 | 9.290 | 9.121 |
| T54 | 21.253 | 8.198 | 11.680 |
| T55 | 12.759 | 5.116 | 8.934 |
| T56 | 14.059 | 1.546 | 0.998 |
| T57 | 11.771 | 3.252 | 13.568 |
| T58 | 12.623 | 1.529 | 5.674 |
| T59 | 16.530 | 1.561 | 2.714 |
| T60 | 15.245 | 5.123 | 7.129 |
| T61 | 13.401 | 5.115 | 11.857 |
| T62 | 15.507 | 2.620 | 5.364 |
| T63 | 11.679 | 1.527 | 2.804 |
| T64 | 1.566 | 11.786 | 8.934 |
| T65 | 2.866 | 8.216 | 0.998 |
| T66 | 0.577 | 9.923 | 13.568 |
| T67 | 1.430 | 8.199 | 5.674 |
| T68 | 5.337 | 8.231 | 2.714 |
| T69 | 4.051 | 11.793 | 7.129 |
| T70 | 2.208 | 11.785 | 11.857 |
| T71 | 4.314 | 9.290 | 5.364 |
| T72 | 0.486 | 8.198 | 2.804 |
| T73 | 10.870 | 9.915 | 7.242 |
| T74 | 22.063 | 3.244 | 7.242 |
| T75 | 10.870 | 3.426 | 7.242 |
| T76 | 22.063 | 10.096 | 7.242 |

In the case of oxygen, it is also possible that the bridging oxygen is also connected to a hydrogen atom to form a hydroxyl group (—OH—). In the case of carbon, it is also possible that the carbon is also connected to two hydrogen atoms to form a methylene group (—$CH_2$—). For example, bridging methylene groups are present in the zirconium diphosphonate, MIL-57. See: C. Serre, G. Férey, *J. Mater. Chem.* 12, p. 2367 (2002). In the case of nitrogen, it is also possible that the nitrogen bridging atom is part of an imidazolate anion. For example, bridging imidazolate groups are present in the zinc(II) imidazolate zeolite-type compounds, Zn(mim)$_2$.2H$_2$O, Zn(eim)$_2$.H$_2$O, and Zn(eim/mim)$_2$.1.25H$_2$O. See: X-C. Huang, Y-Y. Lin, J-P. Zhang. X-M. Chen, *Angew. Chem. Int. Ed.* 45, p. 1557-1559 (2006). Bridging sulfur and selenium atoms have been seen in the UCR-20-23 family of microporous materials. See: N. Zheng, X. Bu, B. Wang, P. Feng, *Science* 298, p. 2366 (2002). Bridging fluorine atoms have been seen in lithium hydrazinium fluoroberyllate, which has the ABW structure type. See: M. R. Anderson, I. D. Brown, S. Vilminot, *Acta Cryst.* B29, p. 2626 (1973). Since tetrahedral atoms may move about due to other crystal forces (presence of inorganic or organic species, for example), or by the choice of tetrahedral and bridging atoms, a range of ±1.0 Ångström is implied for the x and coordinate positions and a range of ±0.5 Ångström for the y and z coordinate positions.

The complete structure of ITQ-55 is built by connecting multiple unit cells as defined above in a fully-connected three-dimensional framework. The tetrahedral atoms in one unit cell are connected to certain tetrahedral atoms in all of its adjacent unit cells. While Table V lists the connections of all the tetrahedral atoms for a given unit cell of ITQ-55, the connections may not be to the particular atom in the same unit cell but to an adjacent unit cell. All of the connections listed in Table V are such that they are to the closest tetrahedral (T) atoms, regardless of whether they are in the same unit cell or in adjacent unit cells.

Although the Cartesian coordinates given in Table VI may accurately reflect the positions of tetrahedral atoms in an idealized structure, the true structure can be more accurately described by the connectivity between the framework atoms as shown in Table V above.

Another way to describe this connectivity is by the use of coordination sequences as applied to microporous frameworks by W. M. Meier and H. J. Moeck, in the *Journal of Solid State Chemistry* 27, p. 349 (1979). In a microporous framework, each tetrahedral atom, $N_0$, (T-atom) is connected to $N_1$=4 neighboring T-atoms through bridging atoms (typically oxygen). These neighboring T-atoms are then connected to $N_2$ T-atoms in the next shell. The $N_2$ atoms in the second shell are connected to $N_3$ T-atoms in the third shell, and so on. Each T-atom is only counted once, such that, for example, if a T-atom is in a 4-membered ring, at the fourth shell the $N_0$ atom is not counted second time, and so on. Using this methodology, a coordination sequence can be determined for each unique T-atom of a 4-connected net of T-atoms. The following line lists the maximum number of T-atoms for each shell.

$N_0$=1  $N_1 \leq 4$  $N_2 \leq 12$  $N_3 \leq 36$  $N_k \leq 4 \cdot 3^{k-1}$

TABLE VII

Coordination sequence for ITQ-55 structure

| Atom | coordination sequence | | | | | | | | | |
|---|---|---|---|---|---|---|---|---|---|---|
| T1 | 4 | 10 | 20 | 36 | 54 | 73 | 100 | 135 | 181 | 224 |
| T2 | 4 | 9 | 17 | 30 | 53 | 81 | 102 | 123 | 161 | 209 |
| T3 | 4 | 10 | 20 | 34 | 52 | 76 | 104 | 133 | 165 | 203 |
| T4 | 4 | 11 | 21 | 32 | 49 | 76 | 108 | 141 | 173 | 210 |
| T5 | 4 | 12 | 22 | 34 | 46 | 74 | 108 | 144 | 174 | 212 |
| T6 | 4 | 10 | 18 | 32 | 56 | 82 | 103 | 128 | 170 | 217 |
| T7 | 4 | 10 | 20 | 34 | 54 | 81 | 106 | 134 | 176 | 222 |
| T8 | 4 | 10 | 21 | 36 | 54 | 74 | 98 | 131 | 172 | 217 |
| T9 | 4 | 11 | 19 | 33 | 57 | 79 | 103 | 136 | 172 | 217 |
| T10 | 4 | 9 | 17 | 31 | 51 | 75 | 104 | 133 | 165 | 206 |

One way to determine the coordination sequence for a given structure is from the atomic coordinates of the framework atoms using the computer program zeoTsites (see G. Sastre, J. D. Gale, *Microporous and mesoporous Materials* 43, p. 27 (2001).

The coordination sequence for the ITQ-55 structure is given in Table VII. The T-atom connectivity as listed in Table V and is for T-atoms only. Bridging atoms, such as oxygen usually connects the T-atoms. Although most of the T-atoms are connected to other T-atoms through bridging atoms, it is recognized that in a particular crystal of a material having a framework structure, it is possible that a number of T-atoms may not connected to one another. Reasons for non-connectivity include, but are not limited by T-atoms located at the edges of the crystals and by defects sites caused by, for example, vacancies in the crystal. The framework listed in Table V and Table VII is not limited in any way by its composition, unit cell dimensions or space group symmetry.

While the idealized structure contains only 4-coordinate T-atoms, it is possible under certain conditions that some of the framework atoms may be 5- or 6-coordinate. This may occur, for example, under conditions of hydration when the composition of the material contains mainly phosphorous and aluminum T-atoms. When this occurs it is found that T-atoms may be also coordinated to one or two oxygen atoms of water molecules (—$OH_2$), or of hydroxyl groups (—OH). For example, the molecular sieve $AlPO_4$-34 is known to reversibly change the coordination of some aluminum T-atoms from 4-coordinate to 5- and 6-coordinate upon hydration as described by A. Tuel et al. in *J. Phys. Chem. B* 104, p. 5697 (2000). It is also possible that some framework T-atoms can be coordinated to fluoride atoms (—F) when materials are prepared in the presence of fluorine to make materials with 5-coordinate T-atoms as described by H. Koller in *J. Am. Chem. Soc.* 121, p. 3368 (1999).

In second place this invention refers to a method to synthesize the microporous crystalline material ITQ-55.

According to this invention, the method to synthesize the microporous crystalline material, ITQ-55, may include a reaction mixture that includes at least: one or several sources of $SiO_2$, one or several sources of organic cation R, at least one source of anions selected among hydroxide anions, fluoride anions and combinations of the same and water, it undergoes heating at a temperature between 80 and 200° C., and because the reaction mixture has a composition, in terms of molar ratios, between the intervals $R^+/SiO_2$=0.01-1.0,
$OH^-/SiO_2$=0-3.0
$F^-/SiO_2$=0-3.0
$(F^-+OH^-)/SiO_2$=0.01-3.0,
$H_2O/SiO_2$=1-50.

According to an additional particular embodiment of the method the reaction mixture may include, also, one or more source of $GeO_2$ and because it has a composition, in terms of molar ratios, included between the intervals $GeO_2/SiO_2$=0 and 0.5
$R^+/(SiO_2+GeO_2)$=0.01-1.0,
$F^-/(SiO_2+GeO_2)$=0.0-3.0,
$OH^-/(SiO_2+GeO_2)$=0.0-3.0.
$(F^-+OH^-)/(SiO_2+GeO_2)$=0.01-3.0
$H_2O/(SiO_2+GeO_2)$=1-50.

According to one additional particular embodiment of the method, the anion is preferably fluoride and the reaction mixture has a composition, in terms of molar ratios, between the intervals $GeO_2/SiO_2$=0 and 0.5
$R^+/(SiO_2+GeO_2)$=0.01-1.0,
$F^-/(SiO_2+GeO_2)$=0.01-3.0,
$H_2O/(SiO_2+GeO_2)$=1-50.

According to another additional particular embodiment of the method, the anion is preferably hydroxide and may have a reaction mixture that has a composition, in terms of molar ratios, between the intervals $GeO_2/SiO_2$=0 and 0.5
$R^+/(SiO_2+GeO_2)$=0.01-1.0,
$OH^-/(SiO_2+GeO_2)$=0.01-3.0,
$H_2O/(SiO_2+GeO_2)$=1-50.

According to one additional particular embodiment of the method, the reaction mixture can include, also, at least, one source of one or more trivalent elements X.

In one particular embodiment, the reaction mixture comprises exclusively: one or several sources of $SiO_2$, at least one source of one or several trivalent elements X, one or several sources of organic cation R, at least one source of anions selected among hydroxide anions, fluoride anions and the combinations of the same, and water, and it has a composition, in terms of molar ratios, between the intervals $R^+/SiO_2$=0.01-1.0,
$X_2O_3/SiO_2$=0-0.1, excluding the value 0.
$OH^-/SiO_2$=0-3.0
$F^-/SiO_2$=0-3.0
$(OH^-+F^-)/SiO_2$=0.0-3.0, excluding the value 0, and
$H_2O/SiO_2$=1-50.

According to this embodiment, if you add to the reaction mixture, at least one source of $GeO_2$, the composition, in terms of molar ratios will be between the intervals $GeO_2/SiO_2$=0 and 0.5, excluding the value 0
$R^+/(SiO_2+GeO_2)$=0.01-1.0,
$X_2O_3/(SiO_2+GeO_2)$=0-0.1, excluding the value 0,
$OH^-/(SiO_2+GeO_2)$=0-3.0
$F^-/(SiO_2+GeO_2)$=0-3.0
$(OH^-+F^-)/(SiO_2+GeO_2)$=0.0-3.0, excluding the value 0, and
$H_2O/(SiO_2+GeO_2)$=1-50.

According to another particular embodiment the reaction mixture comprises exclusively: one or several sources of $SiO_2$, at least one source of one or several trivalent elements X, one or several sources of organic cation R, one or several sources of hydroxide anions, and water, and it has a composition, in terms of molar ratios, between the intervals $R^+/SiO_2$=0.01-1.0,
$X_2O_3/SiO_2$=0-0.1, excluding the value 0,
$OH^-/SiO_2$=0-3.0, excluding the value 0, and
$H_2O/SiO_2$=1-50.

According to this embodiment, if you add to a reaction mixture, at least one source of $GeO_2$, the composition, in terms of molar ratios will be between the intervals $GeO_2/SiO_2$=0 and 0.5, excluding the value 0
$R^+/(SiO_2+GeO_2)$=0.01-1.0,
$X_2O_3/(SiO_2+GeO_2)$=0-0.1, excluding the value 0,
$OH^-/(SiO_2+GeO_2)$=0-3.0, excluding the value 0, and
$H_2O/(SiO_2+GeO_2)$=1-50.

According to a particular embodiment the reaction mixture comprises exclusively: one or several sources of $SiO_2$,
at least one source of one or several trivalent elements X
one or several sources of organic cation R,
one or several sources of fluoride anions, and
water,
and has a composition, in terms of molar ratios, between the intervals $R^+/SiO_2$=0.01-1.0,
$X_2O_3/SiO_2$=0-0.1, excluding the value 0,
$F^-/SiO_2$=0-3.0, excluding the value 0, and
$H_2O/SiO_2$=1-50.

According to this embodiment, if to reaction mixture you add, at least one source of $GeO_2$, the composition, in terms of molar ratios will be between the intervals $GeO_2/SiO_2$=0 and 0.5, excluding the value 0
$R^+/(SiO_2+GeO_2)$=0.01-1.0,
$X_2O_3/(SiO_2+GeO_2)$=0-0.1, excluding the value 0,
$F^-/(SiO_2+GeO_2)$=0-3.0, excluding the value 0, and
$H_2O/(SiO_2+GeO_2)$=1-50.

According to another preferred embodiment, in the method previously described, the reaction mixture may also include, at least one source of other tetravalent elements Y, different from Si and Ge.

According to one particular embodiment, the reaction mixture comprises exclusively: one or several sources of $SiO_2$, at least one source of one or several tetravalent elements Y, one or several sources of organic cation R, at least one source of anions selected between hydroxide anions, fluoride anions and combinations of them, and water, and it has a composition, in terms of molar ratios, between the intervals $R^+/SiO_2$=0.01-1.0,
$YO_2/SiO_2$=0-0.1, excluding the value 0,
$OH^-/SiO_2$=0-3.0,
$F^-/SiO_2$=0-3.0
$(OH^-+F^-)/SiO_2$=0-3.0, excluding the value 0, and
$H_2O/SiO_2$=1-50.

According to this embodiment, if to the reaction mixture you add, at least one source of $GeO_2$, the composition, in terms of molar ratios will be between the intervals $GeO_2/SiO_2$=0 and 0.5, excluding the value 0
$R^+/(SiO_2+GeO_2)$=0.01-1.0,
$YO_2/(SiO_2+GeO_2)$=0-0.1, excluding the value 0,
$OH^-/(SiO_2+GeO_2)$=0-3.0,
$F^-/(SiO_2+GeO_2)$=0-3.0
$(OH^-+F^-)/(SiO_2+GeO_2)$=0-3.0, excluding the value 0, and
$H_2O/(SiO_2+GeO_2)$=1-50.

According to another particular embodiment of the method, the reaction mixture comprises exclusively: one or several sources of $SiO_2$, at least a source of one or several tetravalent elements Y one or several sources of organic cation R, one or several sources of hydroxide anions, and water, and it has a composition, in terms of molar ratios, between the intervals $R^+/SiO_2$=0.01-1.0,
$YO_2/SiO_2$=0-0.1, excluding the value 0,
$OH^-/SiO_2$=0-3.0, excluding the value 0, and
$H_2O/SiO_2$=1-50.

According to this embodiment, if you add to the reaction mixture, at least one source of $GeO_2$, the composition, in terms of molar ratios will be between the intervals $GeO_2/SiO_2$=0 and 0.5, excluding the value 0
$R^+/(SiO_2+GeO_2)$=0.01-1.0,
$YO_2/(SiO_2+GeO_2)$=0-0.1, excluding the value 0,
$OH^-/(SiO_2+GeO_2)$=0-3.0, excluding the value 0, and
$H_2O/(SiO_2+GO_2)$=1-50.

According to another particular embodiment of the method, the reaction mixture comprises exclusively: one or several sources of $SiO_2$, at least one source of one or several tetravalent elements Y, one or several sources of organic cation R, one or several sources of fluoride anions, and water, and it has a composition, in terms of molar ratios, between the intervals $R^+/SiO_2$=0.01-1.0,
$YO_2/SiO_2$=0-0.1, excluding the value 0,
$F^-/SiO_2$=0-3.0, excluding the value 0, and
$H_2O/SiO_2$=1-50.

According to this embodiment, if you add to the reaction mixture, at least one source of $GeO_2$, the composition, in terms of molar ratios will be between the intervals $GeO_2/SiO_2$=0 and 0.5, excluding the value 0
$R^+/(SiO_2+GeO_2)$=0.01-1.0,
$YO_2/(SiO_2+GeO_2)$=0-0.1, excluding the value 0,
$F^-/(SiO_2+GeO_2)$=0-3.0, excluding the value 0, and
$H_2O/(SiO_2+GeO_2)$=1-50.

According to another particular embodiment of the described method, the reaction mixture may include one or several sources of several trivalent elements X as well as one or several sources of one or several tetravalent elements.

According to one particular embodiment, the reaction mixture comprises exclusively: one or several sources of $SiO_2$, at least one source of one or several trivalent elements X, at least one source of one or several tetravalent elements Y, and/or several sources of organic cation R, at least one source of anions selected among hydroxide anions, fluoride anions and combinations of the same, and water, and the reaction mixture has a composition, in terms of molar ratios, between the intervals $R^+/SiO_2$=0.01-1.0.
$X_2O_3/SiO_2$=0-0.1, excluding the value 0,
$YO_2/SiO_2$=0-0.1, excluding the value 0,
$OH^-/SiO_2$=0-3.0
$F^-/SiO_2$=0-3.0

$(OH^-+F^-)/SiO_2$=0-3.0, excluding the value 0, and
$H_2O/SiO_2$=1-50

According to this embodiment, if you add to the reaction mixture, at least one source of $GeO_2$, the composition, in terms of molar ratios will be between the intervals $GeO_2/SiO_2$=0 and 0.5, excluding the value 0
$R^+/(SiO_2+GeO_2)$=0.01-1.0,
$X_2O_3/(SiO_2+GeO_2)$=0-0.1, excluding the value 0,
$YO_2/(SiO_2+GeO_2)$=0-0.1, excluding the value 0,
$OH^-/(SiO_2+GeO_2)$=0-3.0
$F^-/(SiO_2+GeO_2)$=0-3.0
$(OH^-+F^-)/(SiO_2+GeO_2)$=0-3.0, excluding the value 0, and
$H_2O/(SiO_2+GeO_2)$=1-50

According to another particular embodiment the reaction mixture comprises exclusively: one or several sources of $SiO_2$, at least one source of one or several trivalent elements X, at least one source of one or several tetravalent elements Y, one or several sources of organic cation R, one or several sources of hydroxide anions, and water, and it has a composition, in terms of molar ratios, between the intervals $R^+/SiO_2$=0.01-1.0.
$X_2O_3/SiO_2$=0-0.1, excluding the value 0,
$YO_2/SiO_2$=0-0.1, excluding the value 0,
$OH^-/SiO_2$=0-3.0, excluding the value 0, and
$H_2O/SiO_2$=1-50.

According to this embodiment, if you add to the reaction mixture, at least one source of $GeO_2$, the composition, in terms of molar ratios will be between the intervals $GeO_2/SiO_2$=0 and 0.5, excluding the value 0
$R^+/(SiO_2+GeO_2)$=0.01-1.0,
$X_2O_3/(SiO_2+GeO_2)$=0-0.1, excluding the value 0,
$YO_2/(SiO_2+GeO_2)$=0-0.1, excluding the value 0,
$OH^-/(SiO_2+GeO_2)$=0-3.0, excluding the value 0, and
$H_2O/(SiO_2+GeO_2)$=1-50.

According to another particular embodiment the reaction mixture comprises exclusively: one or several sources of $SiO_2$, at least one source of one or several trivalent elements X, at least one source of one or several tetravalent elements Y, one or several sources of organic cation R, one or several sources of fluoride anions, and water, and it has a composition, in terms of molar ratios, between the intervals $R^+/SiO_2$=0.01-1.0,
$X_2O_3/SiO_2$=0-0.1, excluding the value 0,
$YO_2/SiO_2$=0-0.1, excluding the value 0,
$F^-/SiO_2$=0-3.0 excluding the value 0, and
$H_2O/SiO_2$=1-50

According to this embodiment, if you add to the reaction mixture, at least one source of $GeO_2$, the composition, in terms of molar ratios will be between the intervals $GeO_2/SiO_2$=0 and 0.5, excluding the value 0
$R^+/(SiO_2+GeO_2)$=0.01-1.0,
$X_2O_3/(SiO_2+GeO_2)$=0-0.1, excluding the value 0,
$YO_2/(SiO_2+GeO_2)$=0-0.1, excluding the value 0,
$F^-/(SiO_2+GeO_2)$=0-3.0 excluding the value 0, and
$H_2O/(SiO_2+GeO_2)$=1-50.

According to the method previously described, the reaction mixture can include, also, a source of inorganic cations M of charge +n, selected among H+, at least one inorganic cation of charge +n selected between alkaline, alkaline earth metals and combinations of the same, and a mixture of both.

According to a preferred embodiment of the described method, the cation R can be $N^2,N^2,N^2,N^5,N^5,N^5$,3a,6a-octamethyloctahydropentalene-2,5-diammonium. In a general manner, one may say that the reaction mixture can have a composition, in terms of molar ratios, between the intervals $GeO_2/SiO_2$=0 and 0.5,
$R^+/(SiO_2+GeO_2)$=0.01-1.0,
$M^{+n}/(SiO_2+GeO_2)$=0-1.0
$OH^-/(SiO_2+GeO_2)$=0-3.0
$F^-/(SiO_2+GeO_2)$=0-3.0
$(F^-+OH^-)/(SiO_2+GeO_2)$=0-3,
$X_2O_3/(SiO_2+GeO_2)$=0-0.1,
$YO_2/(SiO_2+GeO_2)$=0-0.1, and
$H_2O/(SiO_2+GeO_2)$=1-50.

According to one particular embodiment, the composition of the reaction mixture that gives rise to obtaining the ITQ-55 material may represent in a general way the following formula with the values of the parameters that are indicated in terms of molar ratios:

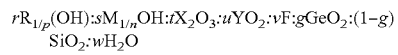

$$rR_{1/p}(OH){:}sM_{1/n}OH{:}tX_2O_3{:}uYO_2{:}vF{:}gGeO_2{:}(1-g)SiO_2{:}wH_2O$$

where M is one or several inorganic cations of charge +n; preferably alkaline or alkaline earth, X is one or several trivalent elements, preferably Al, B, Ga, Fe, Cr or mixtures of them; Y is one or several tetravalent elements different from Si, preferably Zr, Ti, Sn, V or mixtures of them; R is one or more organic cations, p is the charge of the cation or the average charge of the cations, preferably $N^2,N^2,N^2,N^5,N^5,N^5$,3a,6a-octamethylo-octahydropentalene-2,5-diammonium; F is one or more sources of fluoride ions, preferably HF, $NH_4F$, or a mixture of both, and the values of g, r, s, t, u, v and w vary in the intervals:

g=0-0.5, preferably 0-0.33
r=$ROH/SiO_2$=0.01-1.0, preferably 0.1-1.0
s=$M_{1/n}OH/SiO_2$=0-1.0, preferably 0-0.2
t=$X_2O_3/SiO_2$=0-0.1, preferably 0-0.05
u=$YO_2/SiO_2$=0-0.1, preferably 0-0.05
v=$F/SiO_2$=0-3.0, preferably 0-2.0
w=$H_2O/SiO_2$=1-50, preferably 1-20

The components of the synthesis mixture may come from different sources, and depending on these, the times and crystallization conditions may vary.

Preferably the thermal treatment of the mixture is carried out at a temperature between 110 and 200° C. The thermal treatment of the reaction mixture can be carried out as static or with stirring of the mixture. Once the crystallization is concluded the solid product is separated by filtration or centrifuging and dried. The subsequent calcining at temperatures greater than 350° C., preferably between 400 and 1300° C., and more preferably between 600 and 1000° C., produces the decomposition of the organic remnants occluded within the zeolite and their expulsion, leaving the zeolitic channels clear.

The source of $SiO_2$ may be, for example, tetraethylorthosilicate, colloidal silica, amorphous silica and mixtures thereof.

The fluoride anion may be used as mobilizing agent of the precursor species. The source of fluoride ions is preferably HF, $NH_4F$ or a mixture of both.

The organic cation(s), represented by R, are added to the reaction mixture preferably in hydroxide form, of another salt, for example, a halide, and a hydroxide mixture and another salt, that is to say additionally, a source may be added of alkaline, alkaline earth ions, or mixtures of both (M), in hydroxide form or in salt form.

In a preferred way the organic cation R is $N^2,N^2,N^2,N^5$, $N^5,N^5$,3a,6a-octamethyl-octahydropentalene-2,5-diammonium, and it is added preferably in a form selected between hydroxide, another salt and a hydroxide mixture and another salt, preferably a halide.

The organic cation $N^2,N^2,N^2,N^5,N^5,3a,6a$-octamethylo-octahydropentalene-2,5-diammonium is synthesized following the process represented in the following outline:

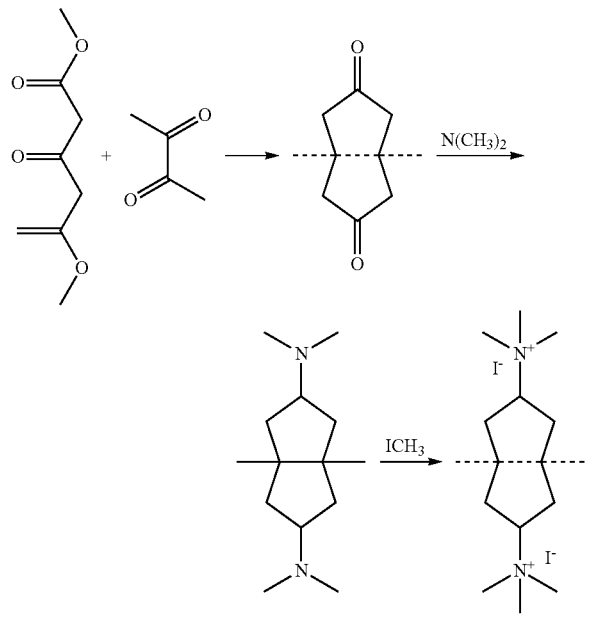

In this process a aldolic condensation reaction is carried out followed by a decarboxylation reaction between the dimethyl 1,3-acetonadicarboxylate with 2,3-butanodione to give rise to the corresponding diketone, 3a,6a-dimethyltetrahydropentalene-2,5(1H,3H)-dione. The diketone is transformed into the corresponding diamine by means of a reductive amination reaction in the presence of dimethylamine and using sodium cyanoborohydride as reducer, giving rise to the diamine, $N^2,N^2,N^5,N^5,3a,6a$-hexamethyloctahydropentalene-2,5-diamine. This diamine is subsequently quaternized with methyl iodide to give rise to the salt of $N^2,N^2,N^2,N^5,N^5,N^5,3a,6a$-octamethyloctahydropentalene-2,5-diammonium di-iodide.

The salt of dialkylammonium diodide may be dissolved in water and exchanged with its hydroxide form using an anionic exchange resin in hydroxide form.

According to one particular embodiment of the method, a quantity is added to the reaction mixture of microporous crystalline material, ITQ-55, from this invention as promoter of the crystallization in a quantity between 0.01 and 20% by weight, preferably between 0.05 and 10% by weight with regard to the total of added inorganic oxides.

Also, the material produced by means of this invention may be pelletized in accordance with well-known techniques.

This invention also refers to the use of the microporous crystalline material previously described and obtained according to the process previously described.

The material of this invention, may be used as a catalyst or component of catalysts in transformation processes of organic compounds, or as adsorbent in adsorption and separation processes of organic compounds.

For its use in the previously mentioned processes it is preferable that ITQ-55 is in its calcined form without organic matter in its interior.

The ITQ-55 material used in these catalytic applications may be in its acidic form and/or exchanged with appropriate cations, such as $H^+$ and/or an inorganic cation of charge +n, selected among alkaline, alkaline-earth metals, lanthanides and combinations thereof.

The ITQ-55 material used in adsorption/separation processes may be in its purely siliceous form, that is to say, not containing elements other than silicon and oxygen in its composition.

The ITQ-55 material used in adsorption/separation processes may be in silica-germania form, that is to say, not containing elements other than silicon, germanium and oxygen in its composition.

The ITQ-55 material is particularly appropriate for use as selective adsorbent of $CO_2$ in the presence of hydrocarbons, preferably methane, ethane, ethylene and combinations of the same, in streams that contain these gases, well as adsorbent in powdered or pelletized form or in membrane form.

According to one specific embodiment, the ITQ-55 material may be used for the separation of $CO_2$ and methane.

According to one specific embodiment, the ITQ-55 material may be used for the separation of $CO_2$ and ethane.

According to one specific embodiment, the ITQ-55 material may be used for the separation of $CO_2$ and ethylene.

According to another particular embodiment, the ITQ-55 material is particularly appropriate for the separation in adsorption processes of hydrocarbons of 1 or 2 carbon atoms that contain these gases, as well as adsorbent in powdered or pelletized form or in membrane form.

According to one specific embodiment, the ITQ-55 material is used as a selective adsorbent of ethylene in the presence of ethane.

According to another specific embodiment, the ITQ-55 material is used as selective adsorbent of ethylene in the presence of methane.

Throughout the description and the claims the word "includes" and its variants does not seek to exclude other technical characteristics, additives, components or steps. For the experts in the matter, other objects, advantages and characteristic of the invention shall come partly from the description and partly from the practice of the invention.

Separation Process and Method of Use Overview

In this discussion, a fluid is defined as a gas or a liquid, including mixtures of both gas and liquid. In this discussion, ambient temperature generally refers to a pressure of about 1 atmosphere (about 101 kPa) and a temperature of about 20° C.

In various aspects, processes are provided that implement a molecular sieve corresponding to zeolite ITQ-55 as described herein for adsorption and/or separation of components of fluid streams, such as gas streams, liquid streams, or streams corresponding to a mixture of gas and liquid. The zeolite ITQ-55 can be suitable for separating a variety of small molecules and/or noble gases. At some temperatures, a molecular sieve corresponding to zeolite ITQ-55 can be suitable for adsorbing a variety of small molecules while reducing, minimizing, or even substantially eliminating adsorption of methane and other compounds containing at least one methyl group. For example, zeolite ITQ-55 can be suitable for performing separations to separate $H_2$, $N_2$, or $CO_2$ from methane. A variety of other types of fluid separations can also be performed depending on the composition of an input gas and the temperature and pressure during the separation process.

The pore structure of zeolite ITQ-55 includes 8-member ring channels. The 8-member ring channels include a minimum pore channel size in the pore network of 5.9 Angstroms×2.1 Angstroms at ambient temperature. This minimum pore channel size can limit the types of compounds that can effectively enter and/or pass through the pore network. However, the 8-member ring that provides the minimum size is also believed to have flexibility. This flexibility can allow the 8-member ring to deform, such as due to thermal fluctuations and/or due to fluctuations induced at elevated pressures, which can lead to a potential temporary change in the size of the pore channel. Without being bound by any particular theory, it is believed that the flexibility of the 8-member ring defining the size of the pore channel can allow for additional tuning of separations of various compounds based on temperature and/or pressure.

Additionally or alternately, the particle size of ITQ-55 crystals used in an adsorbent structure or membrane structure can have an impact on the ability of the adsorbent structure or membrane structure to perform a separation. As one example, the particle size of the ITQ-55 crystals can have an influence on the amount of "dead space" that is present at the surface and/or within the interior of an adsorbent structure or membrane structure. Mathematically, the packing density of a collection of hard spheres of similar size is dependent on the radius of the spheres. For a collection of hard spheres, the larger the average radius, the larger the size of the spaces or gaps between the hard spheres. Without being bound by any particular theory, it is believed that for a collection of ITQ-55 crystals of similar size, the size of the voids or dead spaces created after close packing of crystals can be related to the average particle size. Having a smaller particle size can reduce such dead space, thus providing an increased pore surface area for accepting fluid components for separation.

Additionally or alternately, the composition of ITQ-55 crystals used in an adsorbent structure or membrane structure can have an impact on the ability of the adsorbent structure or the membrane structure to perform a separation. In some aspects, ITQ-55 can be synthesized to have a framework structure composed of primarily silicon and oxygen. In other aspects, a portion of the framework atoms in the ITQ-55 structure can be replaced with other elements. For example, a portion of the silicon in the framework structure can be replaced with atoms from a different group in the periodic table, such as Al, P, or B. As another example, a portion of the silicon in the framework can be replaced with atoms from a different row of the periodic table, such as Ge or P. Such composition variations can modify the size of the pores within the crystal structure and/or modify the affinity of the ITQ-55 relative to one or more potential components for adsorption. Such modifications of pore size and/or affinity can potentially improve selectivity (such as kinetic selectivity) for one or more types of separation.

Zeolite ITQ-55 can be used to separate components in a fluid stream (for example, a gas stream) in various manners. In some aspects, zeolite ITQ-55 can be used to form a membrane structure, so that separation of fluid components is performed by forming a permeate and a retentate portion of a fluid on respective sides of the membrane. Zeolite ITQ-55 can assist with such a membrane separation, for example, by having varying selectivities for allowing fluid components to pass through the membrane.

In other aspects, zeolite ITQ-55 can be used to form an adsorbent structure within a separation vessel, so that separation of fluid components can be performed by adsorbing a portion of a fluid stream within the adsorbent structure while allowing a remainder of the fluid stream to exit from the separation vessel. The adsorbent structure can be composed of the zeolite ITQ-55, or the zeolite ITQ-55 can form a coating as part of an adsorbent structure, so that molecules can pass through the pores of ITQ-55 crystals in order to enter the underlying structure. The zeolite ITQ-55 can assist with performing separations using such an adsorbent structure, for example, by having varying selectivities for allowing fluid components to enter the adsorbent structure.

In still other aspects, zeolite ITQ-55 can be used as part of a storage structure for fluids, such as a storage structure within a storage vessel. A storage structure can in some aspects be similar to an adsorbent structure. However, the storage structure can be used in a different manner, so that gases (or more generally fluids) that enter the storage structure can be retained for an extended period of time. The storage structure can be composed of the zeolite ITQ-55, or the zeolite ITQ-55 can form a coating for a storage structure, so that molecules can pass through the pores of ITQ-55 crystals in order to enter the storage structure. The zeolite ITQ-55 can assist with storage of fluid components using such a storage structure, for example, by having varying selectivities for allowing fluid components to enter the storage structure. The zeolite ITQ-55 can potentially also assist with storage of fluids using such a storage structure, for example, by having a rate of transfer through the pore network that is greater at higher temperature and lower at reduced temperatures. The difference in rate of transfer or movement within the pores of ITQ-55 can be enhanced by the flexible nature of the 8-member ring that defines the minimum pore size for ITQ-55.

Separation of Fluid Components

When a fluid stream is exposed to a membrane structure, adsorbent structure, storage structure, or other porous structure that includes zeolite ITQ-55 as part of the surface of the structure, a selective separation of components within the fluid stream may occur if one or more of the components in the fluid stream has a sufficiently small kinetic diameter.

Some fluid separations can be performed based on one component of a fluid having a sufficiently small kinetic diameter to enter the pores of zeolite ITQ-55 while a second component is too large to enter the pore network under the exposure conditions. For example, it has been determined that hydrocarbons having a terminal methyl group (including methane) and/or other hydrocarbons containing 3 or more carbon atoms generally have kinetic diameters that are too large to enter and/or pass through the pore network of ITQ-55 at typical ambient conditions, such as about 20° C. and about 0.1 MPaa. This is in contrast to compounds with a smaller kinetic diameter, such as $H_2$ or $N_2$, which can enter and/or pass through the pore network. In this type of situation, a separation can be performed with a high degree of selectivity, as the amount of hydrocarbon entering an ITQ-55 layer can be substantially limited to hydrocarbons that enter at a discontinuity in the ITQ-55 layer, such as a mesopore or macropore at a crystal or grain boundary.

Other types of separations can be dependent on differences in uptake by zeolite ITQ-55 between two (or more) fluid components that have sufficiently small kinetic diameters to enter and/or pass through the pore network of ITQ-55. In this situation, separation of components in an input fluid stream can be performed based on a kinetic separation or an equilibrium separation of the components. The nature of the separation can be dependent on, for example, the relative kinetic diameters of the components and/or the relative affinities of the components for the ITQ-55.

One example of a process where the relationship between the kinetic diameters and/or affinities of molecules and the size of the pore network of a zeolite can be relevant is in selective adsorption of components from a fluid stream. In equilibrium controlled adsorption processes, most of the selectivity is imparted by the equilibrium adsorption properties of the adsorbent, and the competitive adsorption isotherm of a first fluid component in the micropores or free volume of the adsorbent is not favored relative to a second component. In kinetically controlled processes, most of the selectivity is imparted by the diffusional properties of the adsorbent and the transport diffusion coefficient in the micropores and free volume of the competing adsorbed components. In some kinetically controlled processes, a component with a higher diffusivity can be preferentially adsorbed relative to a component with a lower diffusivity. Additionally or alternately, the relative affinity of competing adsorbed components for ITQ-55 can be a factor, which may alter the selectivity for separation of components relative to an expected selectivity based just on diffusivity. Also, in kinetically controlled processes with microporous adsorbents, diffusional selectivity can arise from diffusion differences in the micropores of the adsorbent and/or from selective diffusional surface resistance in the crystals or particles that make-up the adsorbent.

Unless otherwise noted, the term "adsorbent selectivity" as used herein is based on binary (pairwise) comparison of the molar concentration of components in the feed stream and the total number of moles of each of these components that are adsorbed by the particular adsorbent during the adsorption step of a process cycle (such as a swing adsorption process cycle) under the specific system operating conditions and feedstream composition. For a feed containing component A, component B, as well as additional components, an adsorbent that has a greater "selectivity" for component A than component B will have at the end of the adsorption step of a process cycle a ratio: $U_A$=(total moles of A in the adsorbent)/(molar concentration of A in the feed) that is greater than the ratio: $U_B$=(total moles of B in the adsorbent)/(molar concentration of B in the feed), where $U_A$ is the "Adsorption Uptake of component A" and $U_B$ is the "Adsorption Uptake of component B". Therefore for an adsorbent having a selectivity for component A over component B that is greater than one: Selectivity=$U_A/U_B$ (where $U_A > U_B$). Amongst a comparison of different components in the feed, the component with the smallest ratio of the total moles picked up in the adsorbent to its molar concentration in the feed can be referred to as the "lightest" component in the swing adsorption process, while the component with the largest ratio of the total moles picked up in the adsorbent to its molar concentration in the feed can be referred to as the "heaviest" component. This means that the molar concentration of the lightest component in the stream coming out during the adsorption step is greater than the molar concentration of that lightest component in the feed.

In some aspects, the selectivity of an adsorbent can additionally or alternatively be characterized based on a "kinetic selectivity" for two or more fluid components. As used herein, the term "kinetic selectivity" is defined as the ratio of single component diffusion coefficients, D (in $m^2$/sec), for two different species. These single component diffusion coefficients are also known as the transport diffusion coefficients that are measured for a given adsorbent for a given pure gas component. Therefore, for example, the kinetic selectivity for a particular adsorbent for component A with respect to component B would be equal to $D_A/D_B$. The single component diffusion coefficients for a material can be determined by tests well known in the adsorptive materials art. The preferred way to measure the kinetic diffusion coefficient is with a frequency response technique described by Reyes et al. in "Frequency Modulation Methods for Diffusion and Adsorption Measurements in Porous Solids", J. Phys. Chem. B. 101, pages 614-622, 1997.

In other aspects, the selectivity of an adsorbent can additionally or alternatively be characterized based on an "equilibrium selectivity" for two or more fluid components. As used herein, the term "equilibrium selectivity" is defined in terms of the slope of the single component uptake into the adsorbent (in μmol/g) vs. pressure (in torr) in the linear portion, or "Henry's regime", of the uptake isotherm for a given adsorbent for a given pure component. The slope of this line is called herein the Henry's constant or "equilibrium uptake slope", or "H". The "equilibrium selectivity" is defined in terms of a binary (or pairwise) comparison of the Henrys constants of different components in the feed for a particular adsorbent. Therefore, for example, the equilibrium selectivity for a particular adsorbent for component A with respect to component B would be $H_A/H_B$.

Another example of a process where the relationship between the kinetic diameters of molecules (or atoms), affinities of molecules (or atoms) for ITQ-55, and the size of the pore network of a zeolite can be relevant is in selective separation of components from a fluid stream using a membrane. Membrane separations can primarily be performed based on the kinetic selectivity of a membrane. Unlike an adsorbent, any fluid components passing through a membrane to form a permeate can be removed periodically or continuously. For example, the permeate side of the membrane can be exposed to a sweep stream. This can prevent a substantial concentration of a component from accumulating on the permeate side of a membrane, so that transport of a fluid component of interest from the retentate side to the permeate side is enhanced or maximized.

Unless otherwise noted, the term "membrane selectivity" as used herein is based on binary (pairwise) comparison of the molar concentration of components in the feed stream and the total number of moles of these components that pass through the membrane to form a permeate during a membrane separation under the specific system operating conditions and feedstream composition. For a feed containing component A, component B, as well as additional components, a membrane that has a greater "selectivity" for component A than component B will have at various times during the membrane separation and/or at the end of the membrane separation a ratio: $X_A$=(molar concentration of A in the permeate)/(molar concentration of A in the feed) is greater than the ratio: Xa=(molar concentration of B in the permeate)/(molar concentration of B in the feed). Therefore, for a membrane having a selectivity for component A over component B that is greater than one, a selectivity can be defined as Selectivity=$X_A/X_B$ (where $X_A > X_B$).

Still another example of a process where the relationship between the kinetic diameters of molecules (or atoms), the affinities of the molecules (or atoms) for ITQ-55, and the size of the pore network of a zeolite can be relevant is in storage of a fluid component. In a storage situation, if a fluid component for storage is exposed to a storage (adsorbent) structure as part of a substantially pure stream of the fluid component, the kinetic diameter of a component and/or relative affinity of a component for ITQ-55 may be less important so long as the component can enter the pore network. However, if the fluid component for storage is introduced as part of a multi-component stream, the ability to load the storage structure can be dependent on the selectivity of the storage structure (either kinetic or equilibrium) for the desired component. Additionally, during a storage period, the ability to modify the storage conditions for the storage structure can be beneficial in retaining a fluid component within the storage structure, such as by reducing or minimizing the ability of the component to exit the storage structure during the storage period.

Based on the minimum 8-member ring size in the pore network of zeolite ITQ-55, fluid components that can be adsorbed and/or separated using the zeolite at ambient conditions (i.e., 20° C. and 0.1 MPaa) can correspond to components with relatively small kinetic diameters, such as kinetic diameters of about 0.40 nm or less, or about 0.38 nm or less. The following list of molecules (and noble gas atoms) provides a listing of components that can be adsorbed and/or separated using zeolite ITQ-55. The following list is not intended to be exhaustive. The listing is roughly based on previously determined values of kinetic diameters for the listed components. It is noted that many of these previously determined values are based an assumption of a spherical molecule. As a result, the order shown in the following list may not necessarily correspond to the actual kinetic selectivity. For example, literature values for the kinetic diameter of $H_2O$ and $H_2$ are similar, with $H_2O$ sometimes having a smaller kinetic diameter as shown in the list. However, in practice $H_2$ may be kinetically favored for adsorption under some adsorption and/or separation conditions.

The following molecules and atoms are generally below methane in kinetic diameter: He, $H_2O$, $H_2$, Ne, $N_2O$, NO, HCl, $Cl_2$, $CO_2$, $C_2H_2$, Ar, $NO_2$, $O_2$, $Br_2$, HBr, $NH_3$, $H_2S$, $SO_2$, $CS_2$, Kr, $N_2$, CO. In addition to this list, it is noted that ethylene and formaldehyde, which have apparent kinetic diameters (under an assumption of a spherical molecule) larger than methane, can also be adsorbed and/or separated by zeolite ITQ-55. It is noted that ethylene and formaldehyde are effectively planar molecules, and therefore the assumption of a spherical molecule is less appropriate. Similarly, molecules like acetylene are less well represented by a spherical molecule assumption. Without being bound by any particular theory, it is believed that the kinetic diameter for methane is similar to 0.38 nm or 0.40 nm along any axis of methane, due to the roughly spherical shape of a methane molecule (based on the tetrahedral symmetry). By contrast, the kinetic diameter of molecules such as acetylene, ethylene, and formaldehyde is believed to vary depending on the orientation of the molecule. Thus, even though the apparent kinetic diameters of ethylene and formaldehyde (under the assumption of spherical molecules) may be greater than methane, a properly oriented ethylene or formaldehyde molecule can present a smaller kinetic cross-section, which can allow these molecules to enter an ITQ-55 pore network.

In some aspects, it can be desirable to use zeolite ITQ-55 for adsorption and/or separation of components where the zeolite ITQ-55 can provide sufficient selectivity between components. For example, use of ITQ-55 can provide a selectivity for a first fluid component over a second fluid component, either for adsorption or for separation via membrane, of at least about 5, or at least about 10, or at least about 20, or at least about 30.

Examples of separations that can be performed (either via adsorption or membrane separation) include, but are not limited to:

a) Separation of $CO_2$ and/or CO from hydrocarbons, alcohols, and/or other organic compounds having three or more heavy (non-hydrogen) atoms, such as $CO_2$ and/or CO from methane, ethane, ethylene, acetylene, natural gas, flue gas, natural gas liquids, or a combination thereof. Due to the low or minimal adsorption of hydrocarbons by ITQ-55, this separation can be performed under any convenient conditions, so long as the temperature is low enough to substantially minimize adsorption of hydrocarbons.

b) Separation of $CO_2$ and/or CO from nitrogen. Optionally, this separation can be performed at temperatures below (or substantially below) 0° C. and at low to moderate pressures to further improve the selectivity of the separation under either kinetic separation conditions or equilibrium separation conditions.

c) Separation of ethylene, formaldehyde, and/or acetylene from organic compounds having three or more heavy (non-hydrogen) atoms. Due to the low or minimal adsorption of larger hydrocarbons and/or organic compounds by ITQ-55, this separation can be performed under any convenient conditions, so long as the temperature is low enough to substantially minimize adsorption of the larger hydrocarbons and/or organic compounds.

d) Separation of acetylene from ethylene, methane, and/or ethane.

e) Separation of $NO_2$ and/or $SO_2$ from flue gas. Flue gas can contain a variety of hydrocarbons. Due to the low or minimal adsorption of hydrocarbons by ITQ-55, this separation can be performed under any convenient conditions, so long as the temperature is low enough to substantially minimize adsorption of hydrocarbons.

f) Separation of $NO_2$ from $SO_2$. This separation can optionally be performed at ambient temperature or greater as a kinetic separation or an equilibrium separation. Alternatively, the separation can be performed at temperatures less than ambient.

g) Separation of HCl, HBr, $Cl_2$, and/or $Br_2$ from other components.

h) Separation of $N_2$ from methane, natural gas, natural gas liquids ($C_2$+), other hydrocarbons, and/or other organic compounds having three or more heavy atoms (i.e., atoms other than hydrogen). Due to the low or minimal adsorption of hydrocarbons by ITQ-55, this separation can be performed under any convenient conditions, so long as the temperature is low enough to substantially minimize adsorption of hydrocarbons. Additionally or alternately, the separation can be performed at any convenient operating conditions based on kinetic selectivity. This can be in contrast to conventional methods for separation of $N_2$ from hydrocarbons or organic compounds, as conventional methods often involve separation at cryogenic conditions. It is noted that for natural gas, separation of $N_2$, $H_2S$, and/or $CO_2$ from natural gas can be performed prior to liquefying the natural gas, after liquefying the natural gas, or a combination thereof.

i) Separation of $O_2$ from $N_2$ or air. This separation can optionally be performed at ambient temperature or greater as a kinetic separation or an equilibrium separation, or optionally at temperatures below ambient. In some aspects, the separation conditions can be in contrast to conventional methods for separation of $O_2$ from $N_2$ or air, as conventional methods often involve separation at cryogenic conditions.

j) Syngas separations. One example is a separation of methane from other syngas components, such as CO, $CO_2$, and $H_2$, which can be facilitated by the reduced or minimized adsorption of methane by ITQ-55. Another example is separation of $H_2$ from other syngas components, which can optionally be performed as a kinetic separation due to the small kinetic diameter of $H_2$. Optionally, water can be separated from syngas (such as by reducing the temperature to separate water as a liquid) to improve the selectivity for forming an $H_2$ product stream.

k) Separation of CO from methane and/or other compounds. Due to the low or minimal adsorption of hydrocarbons by ITQ-55, separation from typical hydrocarbons and/or organic compounds can be performed under any convenient conditions, so long as the temperature is low enough to substantially minimize adsorption of hydrocarbons.

l) Separation of $H_2$ from water, hydrocarbons, $N_2$. $CO_2$, $NH_3$, CO, other gas components, or a combination thereof.

m) Separation of He from water, hydrocarbons, natural gas, $N_2$, $CO_2$, CO, other gas components, or a combination thereof.

n) Separation of Ne, Ar, and/or Kr from air and/or other gas components.

o) Separation of $NH_3$ from components with a larger kinetic diameter and/or lower affinity for ITQ-55.

p) Separation of $CO_2$ from methane and other higher molecular weight hydrocarbons in a natural gas feedstream.

q) Separation of $H_2O$ from methane and other higher molecular weight hydrocarbons in a natural gas feedstream.

r) Separation of $N_2$ from methane and other higher molecular weight hydrocarbons in a natural gas feedstream.

s) Separation of $H_2O$, $N_2$, or a combination thereof from methane and other higher molecular weight hydrocarbons in a natural gas feedstream.

t) Separation of $H_2S$ from methane and other higher molecular weight hydrocarbons in a natural gas feedstream.

u) Separation of $CS_2$ and/or COS from components with a larger kinetic diameter.

v) Separation of methanol and/or dimethyl ether from higher molecular weight hydrocarbons and organic compounds.

w) Separation of methanol and/or dimethyl ether from methane, ethane, ethylene, acetylene, and/or formaldehyde.

x) Separation of methane or ethane from higher molecular weight hydrocarbons and organic compounds.

y) Separation of $H_2S$ and/or $H_2O$ from methane and/or other higher molecular weight hydrocarbons and/or other organic compounds having three or more heavy (non-hydrogen) atoms.

Adsorbent Separations (Including Swing Processing)

Gas separation (or other fluid separation) is important in various industries and can typically be accomplished by flowing a mixture of gases over an adsorbent that preferentially adsorbs a more readily adsorbed component relative to a less readily adsorbed component of the mixture. Swing adsorption is an example of a commercially valuable separation technique, such as pressure swing adsorption (PSA) or temperature swing adsorption (TSA). PSA processes rely on the fact that under pressure fluids tend to be adsorbed within the pore structure of a microporous adsorbent material or within the free volume of a polymeric material. The higher the pressure, the more fluid is adsorbed. When the pressure is reduced, the fluid is released, or desorbed. PSA processes can be used to separate fluids in a mixture because different fluids tend to fill the micropore or free volume of the adsorbent to different extents. If a gas mixture, such as natural gas, for example, is passed under pressure through a vessel containing polymeric or microporous adsorbent that fills with more nitrogen than it does methane, part or all of the nitrogen will stay in the adsorbent bed, and the gas coming out of the vessel will be enriched in methane. When the adsorbent bed reaches the end of its capacity to adsorb nitrogen, it can be regenerated by reducing the pressure, thereby releasing the adsorbed nitrogen. It is then ready for another cycle.

Another important fluid separation technique is temperature swing adsorption (TSA). TSA processes also rely on the fact that under pressure fluids tend to be adsorbed within the pore structure of a microporous adsorbent material or within the free volume of a polymeric material. When the temperature of the adsorbent is increased, the fluid is released, or desorbed. By cyclically swinging the temperature of adsorbent beds, TSA processes can be used to separate fluids in a mixture when used with an adsorbent that selectively picks up one or more of the components in the fluid mixture.

In addition to swings of pressure and/or temperature in order to form the adsorbed product stream, formation of an adsorbed product stream can be facilitated by exposing the adsorbent to a displacement fluid stream. After performing a separation by selectively adsorbing a component from an input stream, the selectively adsorbed component can be desorbed at least in part by displacing the selectively adsorbed component with another fluid component that has a greater affinity for adsorption. This additional fluid component can be referred to as a displacement fluid component. Optionally, the displacement fluid component can be readily separated from the selectively adsorbed component, such as by condensation and/or phase separation.

Adsorbents for PSA systems are usually very porous materials chosen because of their large surface area. Typical adsorbents are activated carbons, silica gels, aluminas and zeolites. In some cases a polymeric material can be used as the adsorbent material. Though the fluid adsorbed on the interior surfaces of microporous materials may consist of a layer only one, or at most a few molecules thick, surface areas of several hundred square meters per gram enable the adsorption of a significant portion of the adsorbent's weight in gas. The molecular species that selectively fill the micropores or open volume of the adsorbent are typically referred to as the "heavy" components and the molecular species that do not selectively fill the micropores or open volume of the adsorbent are usually referred to as the "light" components.

Various types swing adsorption can be used in the practice of the present invention. Non-limiting examples of such swing adsorption processes include thermal swing adsorption (TSA) and various types of pressure swing adsorption processes including conventional pressure swing adsorption (PSA), and partial pressure swing or displacement purge adsorption (PPSA) technologies. These swing adsorption processes can be conducted with rapid cycles, in which case they are referred to as rapid cycle thermal swing adsorption (RCTSA), rapid cycle pressure swing adsorption (RCPSA), and rapid cycle partial pressure swing or displacement purge adsorption (RCPPSA) technologies. The term swing adsorption processes shall be taken to include all of these processes (i.e. TSA, PSA, PPSA, RCTSA, RCPSA, and RCPPSA) including combinations of these processes. Such processes require efficient contact of a gas mixture with a solid adsorbent material.

Although any suitable adsorbent contactor can be used in the practice of the present invention, including conventional adsorbent contactors, in some aspects structured parallel channel contactors can be utilized. The structure of parallel channel contactors, including fixed surfaces on which the adsorbent or other active material is held, can provide significant benefits over previous conventional gas separation methods, such as vessels containing adsorbent beads or extruded adsorbent particles. With parallel channel contactors, total recovery of the light component (i.e., the component that is not preferentially adsorbed) achieved in a swing adsorption process can be greater than about 80 vol %, or greater than about 85 vol %, or greater than about 90 vol %, or greater than about 95 vol % of the content of the light component introduced into the process. Recovery of the light component is defined as the time averaged molar flow rate of the light component in the product stream divided by the time averaged molar flow rate of the light component in the feedstream. Similarly, recovery of the heavy component (i.e., the component that is preferentially adsorbed) is defined as the time averaged molar flow rate of the heavy component in the product stream divided by the time averaged molar flow rate of the heavy component in the feedstream.

The channels, also sometimes referred to as "flow channels", "fluid flow channels", or "gas flow channels", are paths in the contactor that allow gas or other fluids to flow through. Generally, flow channels provide for relatively low fluid resistance coupled with relatively high surface area. Flow channel length should be sufficient to provide the mass transfer zone which is at least, a function of the fluid velocity, and the surface area to channel volume ratio. The channels are preferably configured to minimize pressure drop in the channels. In many embodiments, a fluid flow fraction entering a channel at the first end of the contactor does not communicate with any other fluid fraction entering another channel at the first end until the fractions recombine after exiting at the second end. It is important that there be channel uniformity to ensure that substantially all of the channels are being fully utilized, and that the mass transfer zone is substantially equally contained. Both productivity and gas/fluid purity will suffer if there is excessive channel inconsistency. If one flow channel is larger than an adjacent flow channel, premature product break through may occur, which leads to a reduction in the purity of the product gas to unacceptable purity levels. Moreover, devices operating at cycle frequencies greater than about 50 cycles per minute (cpm) require greater flow channel uniformity and less pressure drop than those operating at lower cycles per minute. Further, if too much pressure drop occurs across the bed, then higher cycle frequencies, such as on the order of greater than 100 cpm, are not readily achieved.

The dimensions and geometric shapes of the parallel channel contactors can be any dimension or geometric shape that is suitable for use in swing adsorption process equipment. Non-limiting examples of geometric shapes include various shaped monoliths having a plurality of substantially parallel channels extending from one end of the monolith to the other; a plurality of tubular members; stacked layers of adsorbent sheets with and without spacers between each sheet; multi-layered spiral rolls, bundles of hollow fibers, as well as bundles of substantially parallel solid fibers. The adsorbent can be coated onto these geometric shapes or the shapes can, in many instances, be formed directly from the adsorbent material plus suitable binder. An example of a geometric shape formed directly from the adsorbent/binder would be the extrusion of a zeolite/polymer composite into a monolith. Another example of a geometric shape formed directly from the adsorbent would be extruded or spun hollow fibers made from a zeolite/polymer composite. An example of a geometric shape that is coated with the adsorbent would be a thin flat steel sheet that is coated with a microporous, low mesopore, adsorbent film, such as a zeolite film. The directly formed or coated adsorbent layer can be itself structured into multiple layers or the same or different adsorbent materials. Multi-layered adsorbent sheet structures are taught in United States Patent Application Publication No. 2006/0169142, which is incorporated herein by reference.

The dimensions of the flow channels can be computed from considerations of pressure drop along the flow channel. It is preferred that the flow channels have a channel gap from about 5 to about 1,000 microns, preferably from about 50 to about 250 microns. In some RCPSA applications, the flow channels are formed when adsorbent sheets are laminated together. Typically, adsorbent laminates for RCPSA applications have flow channel lengths from about 0.5 centimeter to about 10 meter, more typically from about 10 cm to about 1 meter and a channel gap of about 50 to about 250 microns. The channels may contain a spacer or mesh that acts as a spacer. For laminated adsorbents, spacers can be used which are structures or material, that define a separation between adsorbent laminates. Non-limiting examples of the type of spacers that can be used in the present invention are those comprised of dimensionally accurate: plastic, metal, glass, or carbon mesh; plastic film or metal foil; plastic, metal, glass, ceramic, or carbon fibers and threads; ceramic pillars; plastic, glass, ceramic, or metal spheres, or disks; or combinations thereof. Adsorbent laminates have been used in devices operating at PSA cycle frequencies up to at least about 150 cpm. The flow channel length may be correlated with cycle speed. At lower cycle speeds, such as from about 20 to about 40 cpm, the flow channel length can be as long as or longer than one meter, even up to about 10 meters. For cycle speeds greater than about 40 cpm, the flow channel length typically is decreased, and may vary from about 10 cm to about 1 meter. Longer flow channel lengths can be used for slower cycle PSA processes. Rapid cycle TSA processes tend to be slower than rapid cycle PSA processes and as such longer flow channel lengths can also be used with TSA processes.

In various aspects, an adsorbent contactor can contain a very low volume fraction of open mesopores and macropores. For example, an adsorbent contactor, such as a structured bed adsorbent contactor, can contain less than about 20 vol %, or less than about 15 vol %, or less than about 10 vol %, or less than about 5 vol % of their pore volume in open pores in the mesopore and macropore size range. Mesopores are defined by the IUPAC (and defined herein) to be pores with sizes in the 20 to 500 angstrom size range. Macropores are defined herein to be pores with sizes greater than about 500 Angstroms and less than about 1 micron. It is noted that flow channels within a contactor for allowing an input gas (or fluid) stream to be exposed to the contactor can typically be larger than about 1 micron in size, and therefore are not considered to be part of the macropore volume. Open pores are defined mesopores and macropores that are not occupied by a blocking agent and that are capable of being occupied, essentially non-selectively, by components of a gas mixture. Different test methods as described below can be used to measure the volume fraction of open pores in a contactor depending on the structure of the contactor.

The preferred test for determining the volume fraction of open mesopores and macropores of the contactor is defined as follows and involving an analysis of the isotherm of a condensable vapor adsorbed by the contactor. A liquid which has a vapor pressure greater than about 0.1 torr at the temperature of the test is a material that can be used to produce a condensable vapor. At about 20° C., water, hexane, trimethylbenzene, toluene, xylenes, and isooctane have sufficiently high vapor pressures that they can be used as condensable vapors. In the adsorption branch of the isotherm, capillary condensation fills empty micropore, mesopore, and much of the empty macropore volume with liquid. During desorption, micropores, mesopores, and macropores pores filled with liquid are emptied. It is well known that there is a hysteresis between the adsorption and desorption branches of the isotherm. Detailed analysis of the adsorption isotherm relies in part on the Kelvin equation which is well known to those skilled in the art. The detailed analysis provides a measurement of the volume fraction of the mesopores and macropores in the structured adsorbent and to some extent the size distribution of open mesopores and macropores.

Although the open pore volume for the contactor is determined by the test procedure described above, scanning electron microscopy may be used to further confirm the relative volume of mesopores and macropores in the sample. When scanning electron microscopy is used the surface as well as a cross section of the contactor should be imaged.

Open mesopore and macropore volume includes the volume fraction of all mesopores and macropores that are not filled with an optional blocking agent, and that are non-selective and thus are capable of being occupied essentially by all components of the gas mixture. Non-limiting examples of blocking agents that can be used in the practice of the present invention include polymers, microporous materials, solid hydrocarbons, and liquids that can fill the open mesoporous and macroporous spaces but still allow molecules to transport into the micropores in the selective adsorbent. When the blocking agent is a polymer or liquid, it is preferred that the molecular size of the blocking agent be large enough so that is does not significantly invade micropores of the adsorbent, but not so large that it does not fill the mesopores and macropores. When solid blocking agents are used the particle size of the solid is greater than any selective micropores in the adsorbent but smaller than the meso and macropores. As such the blocking agent can fit into the meso and macropores without significantly occluding or filling micropores which may be present in the adsorbent.

The blocking agent fills the open meso and macropores of the adsorbent to an extent that the volume fraction of the open meso and macropores of the adsorbent meets the aforementioned requirements. Non-limiting examples of polymers that can be used as blocking agents include polyimides, polysulfones, and silicone rubbers. Non-limiting examples of liquids that can be used as blocking agents include amines, aromatics such as 1,3,5 trimethylbenzene and branched saturated hydrocarbons such a heptamethylnonane as well as liquid hydrocarbons having carbon numbers in the about 5 to about 60 range. When a liquid blocking agent is used it is advantageous to saturate, or nearly saturate, the feed gas with the liquid blocking agent. Non-limiting examples of solid blocking agents include hydrocarbons such as waxes and those having carbon numbers in the 10-1000 range. Non-limiting examples of microporous materials that can be used in the practice of the present invention include microporous carbons and zeolites having pore sizes larger than those of the selective structured adsorbent of this invention. An example of an adsorbent formulated with a blocking agent is a silica or alumina bound zeolite layer having about 30% mesoporous and macroporous volume in the interstices between the zeolite particles that is filled in with a liquid so that substantially all voids are filled with liquid (i.e., the total resulting macro and mesoporosity in the layer is less than about 20%). In some cases, the blocking agent forms a continuous network and the adsorbent is a composite structure with the microporous material embedded within the blocking agent. A non-limiting example of such a structure is a zeolite/polymer composite where the polymer is continuous and the composite has less than about 20 vol % in open mesopores and macropores.

It is also possible to formulate the adsorbent using a mesoporous material that fills the macropores to reduce the overall void, or open, volume. An example of such a structure would be an adsorbent having about 30 vol % of macropores that are filled in with a mesoporous sol gel so that the resulting mesopore and macropore volume is less than about 20 vol %.

An example of a process where an adsorbent structure comprising ITQ-55 can be used is a swing adsorption process. A swing adsorption process can include an adsorption step followed by a desorption step to recover the adsorbed component. During the adsorption step, "heavy" components are selectively adsorbed and the weakly adsorbed (i.e., "light") components pass through the bed to form the product gas. It is possible to remove two or more contaminants simultaneously but for convenience, the component or components, that are to be removed by selective adsorption will be referred to in the singular and referred to as a contaminant or heavy component. In a swing adsorption process, the gaseous mixture is passed over a first adsorption bed in a first vessel and a light component enriched product stream emerges from the bed depleted in the contaminant, or heavy component, which remains sorbed in the bed. After a predetermined time or, alternatively when a break-through of the contaminant or heavy component is observed, the flow of the gaseous mixture is switched to a second adsorption bed in a second vessel for the purification to continue. While the second bed is in adsorption service, the sorbed contaminant, or heavy component is removed from the first adsorption bed by a reduction in pressure. In some embodiments, the reduction in pressure is accompanied by a reverse flow of gas to assist in desorbing the heavy component. As the pressure in the vessels is reduced, the heavy component previously adsorbed in the bed is progressively desorbed to a heavy component enriched product stream. When desorption is complete, the sorbent bed may be purged with an inert gas stream, e.g., nitrogen or a purified stream of process gas. Purging may also be facilitated by the use of a purge stream that is higher in temperature than the process feedstream.

After breakthrough in the second bed and after the first bed has been regenerated so that it is again ready for adsorption service, the flow of the gaseous mixture is switched back to the first bed, and the second bed is regenerated. The total cycle time is the length of time from when the gaseous mixture is first conducted to the first bed in a first cycle to the time when the gaseous mixture is first conducted to the first bed in the immediately succeeding cycle, i.e., after a single regeneration of the first bed. The use of third, fourth, fifth, etc. vessels in addition to the second vessel can serve to increase cycle time when adsorption time is short but desorption time is long.

In some aspects, an RCPSA process can be used for separation. The total cycle times of RCPSA may be less than about 30 seconds, preferably less than about 15 seconds, more preferably less than about 10 seconds, even more preferably less than about 5 seconds, and even more preferably less than about 1 second. Further, the rapid cycle pressure swing adsorption units can make use of substantially different sorbents, such as, but not limited to, structured materials such as monoliths, laminates, and hollow fibers.

An adsorbent contactor may optionally contain a thermal mass (heat transfer) material to help control heating and cooling of the adsorbent of the contactor during both the adsorption step and desorption step of a pressure swing adsorption process. Heating during adsorption is caused by the heat of adsorption of molecules entering the adsorbent. The optional thermal mass material also helps control cooling of the contactor during the desorption step. The thermal mass can be incorporated into the flow channels of the contactor, incorporated into the adsorbent itself, or incorporated as part of the wall of the flow channels. When it is incorporated into the adsorbent, it can be a solid material distributed throughout the adsorbent layer or it can be included as a layer within the adsorbent. When it is incorporated as part of the wall of the flow channel, the adsorbent is deposited or formed onto the wall. Any suitable material can be used as the thermal mass material in the practice of the present invention. Non-limiting examples of such materials include metals, ceramics, and polymers. Non-limiting examples of preferred metals include steel alloys, copper, and aluminum. Non-limiting examples of preferred ceramics include silica, alumina, and zirconia. An example of a preferred polymer that can be used in the practice of the present invention is polyimide. Depending upon the degree to which the temperature rise is to be limited during the adsorption step, the amount of thermal mass material used can range from about 0 to about 25 times the mass of the microporous adsorbent of the contactor. A preferred range for the amount of thermal mass in the contactor is from about 0 to 5 times the mass of the microporous adsorbent of the contactor. A more preferred range for the amount of thermal mass material will be from about 0 to 2 times the mass of the microporous adsorbent material, most preferably from about 0 to 1 times the mass of the microporous material of the contactor.

The overall adsorption rate of the swing adsorption processes is characterized by the mass transfer rate from the flow channel into the adsorbent. It is desirable to have the mass transfer rate of the species being removed (i.e., the heavy component) high enough so that most of the volume of the adsorbent is utilized in the process. Since the adsorbent selectively removes the heavy component from the gas stream, inefficient use of the adsorbent layer can lower recovery of the light component and/or decrease the purity of the light product stream. With use of the adsorbent contactors described herein, it is possible to formulate an adsorbent with a low volume fraction of meso and macroporous such that most of the volume of the adsorbent, which will be in the microporous range, is efficiently used in the adsorption and desorption of the heavy component. One way of doing this is to have an adsorbent of substantially uniform thickness where the thickness of the adsorbent layer is set by the mass transfer coefficients of the heavy component and the time of the adsorption and desorption steps of the process. The thickness uniformity can be assessed from measurements of the thickness of the adsorbent or from the way in which it is fabricated. It is preferred that the uniformity of the adsorbent be such that the standard deviation of its thickness is less than about 25% of the average thickness. More preferably, the standard deviation of the thickness of the adsorbent is less than about 15% of the average thickness. It is even more preferred that the standard deviation of the adsorbent thickness be less than about 5% of the average thickness.

Calculation of these mass transfer rate constants is well known to those having ordinary skill in the art and may also be derived by those having ordinary skill in the art from standard testing data. D. M. Ruthven & C. Thaeron, Performance of a Parallel Passage Absorbent Contactor, Separation and Purification Technology 12 (1997) 43-60, which is incorporated herein by reference, clarifies many aspects of how the mass transfer is affected by the thickness of the adsorbent, channel gap and the cycle time of the process. Also, U.S. Pat. No. 6,607,584 to Moreau et al., which is also incorporated by reference, describes the details for calculating these transfer rates and associated coefficients for a given adsorbent and the test standard compositions used for conventional PSA.

Figure 6:
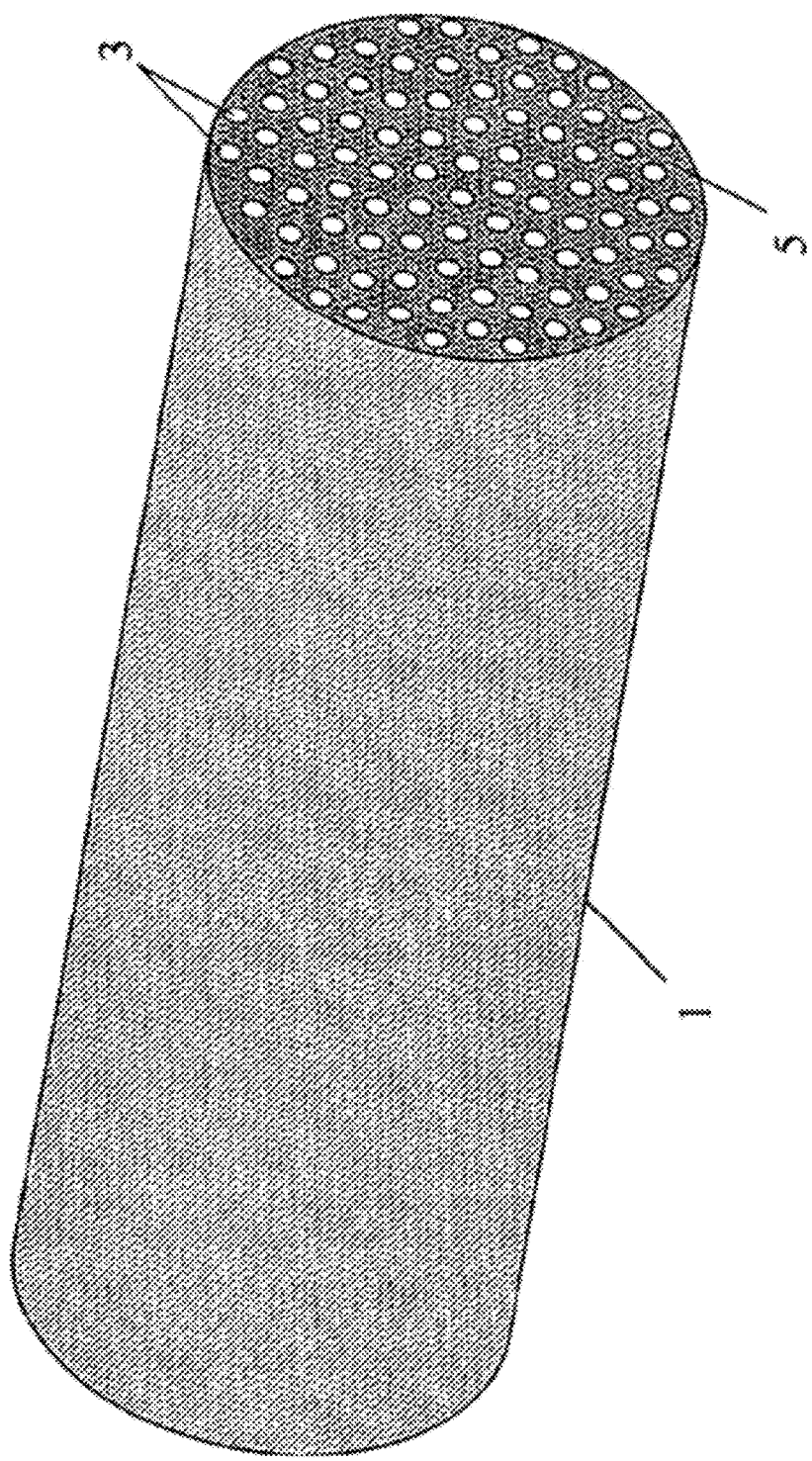
FIG. 6 hereof is a representation of one embodiment of a parallel channel contactor in the form of a monolith directly formed from a microporous adsorbent and containing a plurality of parallel channels.

FIG. 6 hereof is a representation of a parallel channel contactor in the form of a monolith formed directly from a microporous adsorbent plus binder and containing a plurality of parallel flow channels. A wide variety of monolith shapes can be formed directly by extrusion processes. An example of a cylindrical monolith 1 is shown schematically in FIG. 6 hereof. The cylindrical monolith 1 contains a plurality of parallel flow channels 3. These flow channels 3 can have channel gaps from about 5 to about 1,000 microns, preferably from about 50 to about 250 microns, as long as all channels of a given contactor have substantially the same size channel gap. The channels can be formed having a variety of shapes including, but not limited to, round, square, triangular, and hexagonal. The space between the channels is occupied by the adsorbent 5. As shown the channels 3 occupy about 25% of the volume of the monolith and the adsorbent 5 occupies about 75% of the volume of the monolith. The adsorbent 5 can occupy from about 50% to about 98% of the volume of the monolith. The effective thickness of the adsorbent can be defined from the volume fractions occupied by the adsorbent 5 and channel structure as:

Effective Thickness of Adsorbent=½ Channel Diameter*(Volume Fraction of Adsorbent)/(Volume Fraction of Channels)

Figure 7:
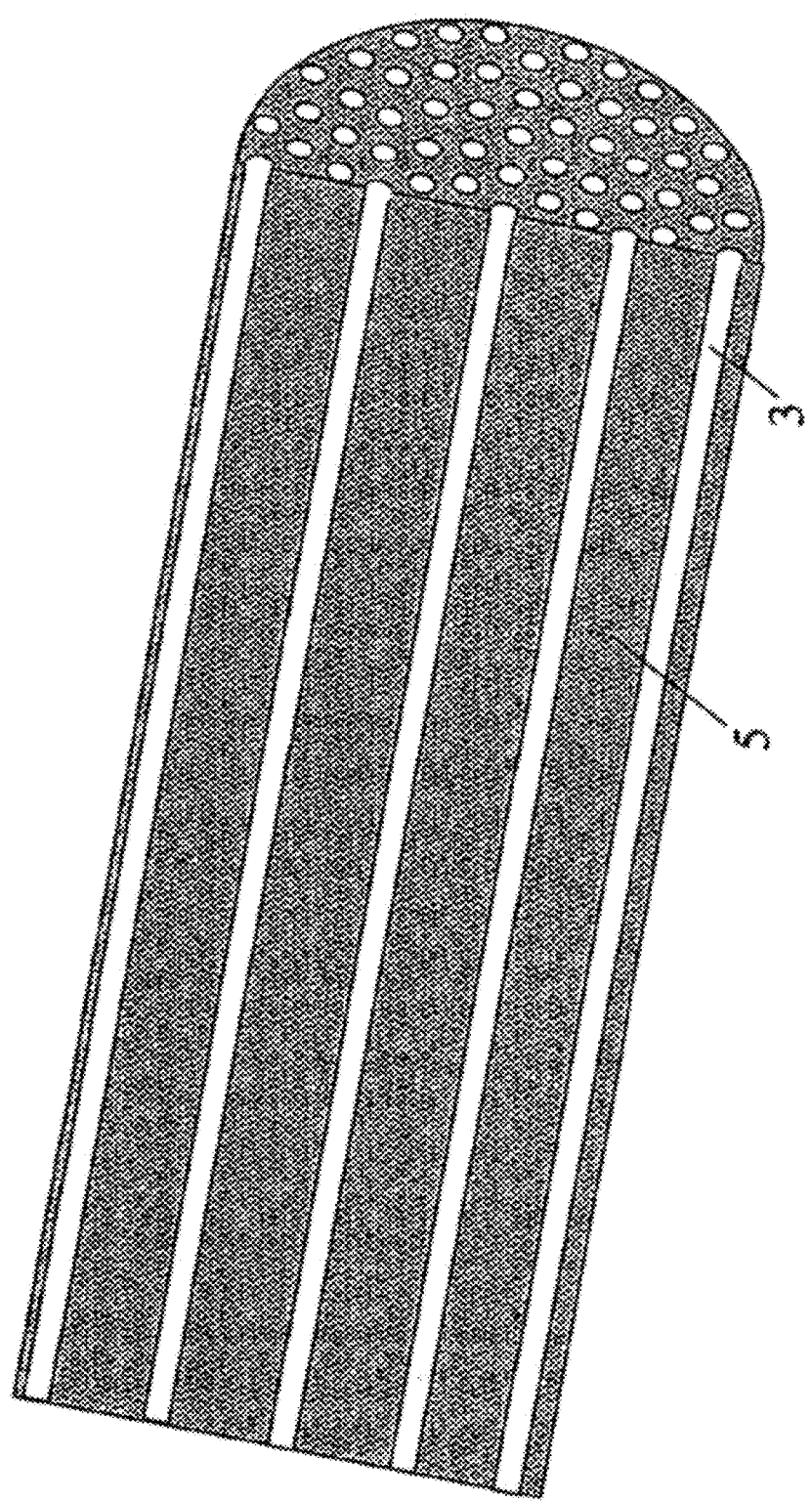
FIG. 7 hereof is a cross-sectional representation along the longitudinal axis of the monolith of FIG. 6.
Figure 8:
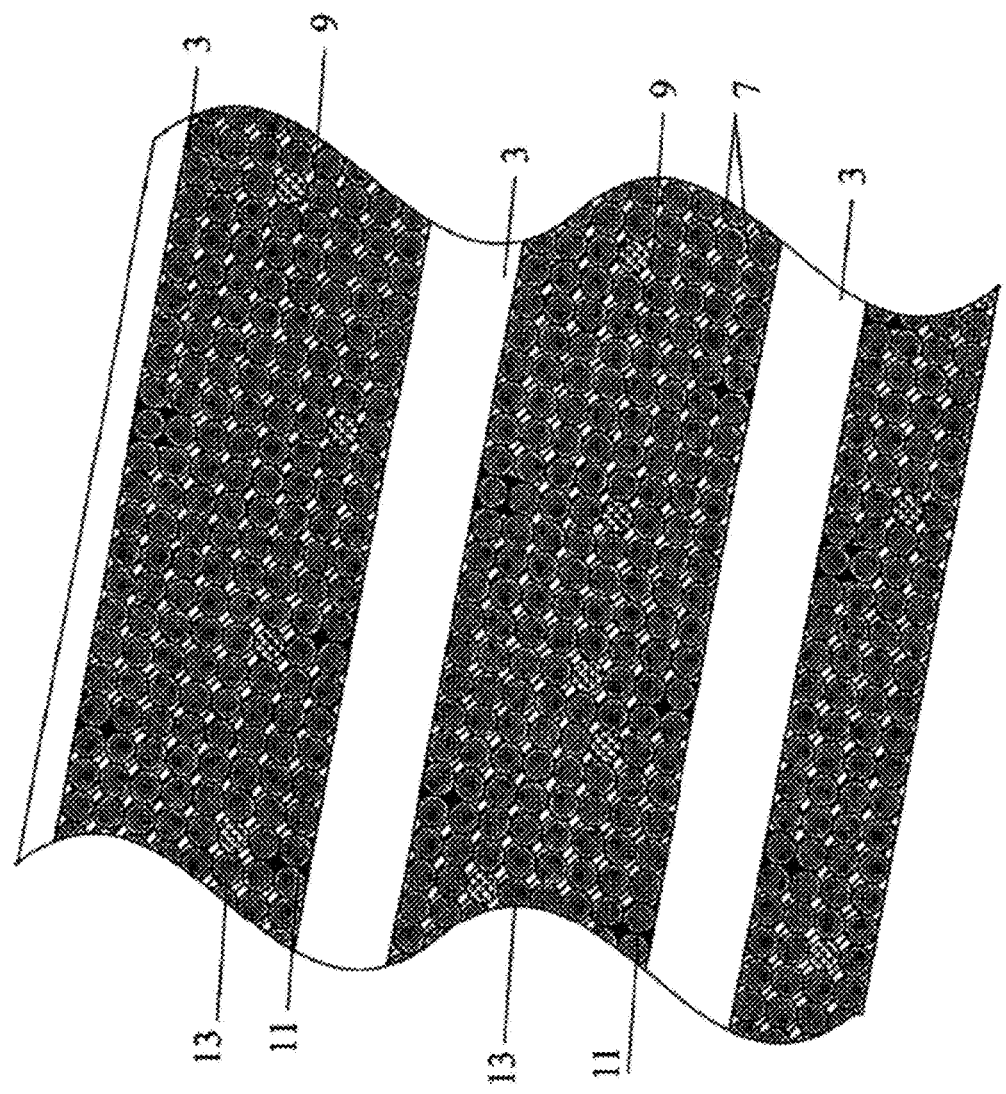
FIG. 8 hereof is a representation of a magnified section of the cross-sectional view of the monolith of FIG. 7 showing the detailed structure of the adsorbent layer along with a blocking agent occupying some of the mesopores and macropores.

For the monolith of FIG. 6 hereof the effective thickness of the adsorbent will be about 1.5 times the diameter of the feed channel. When the channel diameter is in a range from about 50 to about 250 microns it is preferred that the thickness of the adsorbent layer, in the case wherein the entire contactor is not comprised of the adsorbent, be in a range from about 25 to about 2,500 microns. For a 50 micron diameter channel, the preferred range of thickness for the adsorbent layer is from about 25 to about 300 microns, more preferred range from about 50 to about 250 microns. FIG. 7 is a cross-sectional view along the longitudinal axis showing feed channels 3 extending through the length of the monolith with the walls of the flow channels formed entirely from adsorbent 5 plus binder. A schematic diagram enlarging a small cross section of the feed channels 3 and adsorbent layer 5 of FIG. 7 is shown in FIG. 8 hereof. The adsorbent layer is comprised of a microporous adsorbent, or polymeric, particles 7; solid particles (thermal mass) 9; that act as heat sinks, a blocking agent 13 and open mesopores and micropores 11. As shown, the microporous adsorbent or polymeric particles 7 occupy about 60% of the volume of the adsorbent layer and the particles of thermal mass 9 occupy about 5% of the volume. With this composition, the voidage (flow channels) is about 55% of the volume occupied by the microporous adsorbent or polymeric particles. The volume of the microporous adsorbent 5 or polymeric particles 7 can range from about 25% of the volume of the adsorbent layer to about 98% of the volume of the adsorbent layer. In practice, the volume fraction of solid particles 9 used to control heat will range from about 0% to about 75%, preferably about 5% to about 75%, and more preferably from about 10% to about 60% of the volume of the adsorbent layer. A blocking agent 13 fills the desired amount of space or voids left between particles so that the volume fraction of open mesopores and macropores 11 in the adsorbent layer 5 is less than about 20%.

When the monolith is used in a gas separation process that relies on a kinetic separation (predominantly diffusion controlled) it is advantageous for the microporous adsorbent or polymeric particles 7 to be substantially the same size. It is preferred that the standard deviation of the volume of the individual microporous adsorbent or polymeric particles 7 be less than 100% of the average particle volume for kinetically controlled processes. In a more preferred embodiment the standard deviation of the volume of the individual microporous adsorbent or polymeric particles 7 is less than 50% of the average particle volume. The particle size distribution for zeolite adsorbents can be controlled by the method used to synthesize the particles. It is also possible to separate pre-synthesized microporous adsorbent particles by size using methods such as a gravitational settling column. It may also be advantageous to use uniformly sized microporous adsorbent or polymeric particles in equilibrium controlled separations.

There are several ways that monoliths can be formed directly from a structured microporous adsorbent. For example, when the microporous adsorbent is a zeolite, the monolith can be prepared by extruding an aqueous mixture containing effective amounts of a solid binder, zeolite and adsorbent, solid heat control particles, and polymer. The solid binder can be colloidal sized silica or alumina that is used to bind the zeolite and solid heat control particles together. The effective amount of solid binder will typically range from about 0.5 to about 50% of the volume of the zeolite and solid heat control particles used in the mixture. If desired, silica binder materials can be converted in a post processing step to zeolites using hydrothermal synthesis techniques and, as such, they are not always present in a finished monolith. A polymer is optionally added to the mixture for rheology control and to give green extrudate strength. The extruded monolith is cured by firing it in a kiln where the water evaporates and the polymer burns away, thereby resulting in a monolith of desired composition. After curing the monolith, the adsorbent layer 5 will have about 20 to about 40 vol. % mesopores and macropores. A predetermined amount of these pores can be filled with a blocking agent 13, as previously discussed, in a subsequent step such as by vacuum impregnation.

Another method by which a monolith can be formed directly from a microporous adsorbent is by extruding a polymer and microporous adsorbent mixture. Preferred microporous adsorbents for use in extrusion process are carbon molecular sieves and zeolites. Non-limiting examples of polymers suitable for the extrusion process include epoxies, thermoplastics, and curable polymers such as silicone rubbers that can be extruded without an added solvent. When these polymers are used in the extrusion process, the resulting product will preferably have a low volume fraction of mesopores and macropores in the adsorbent layer.

Figure 9:
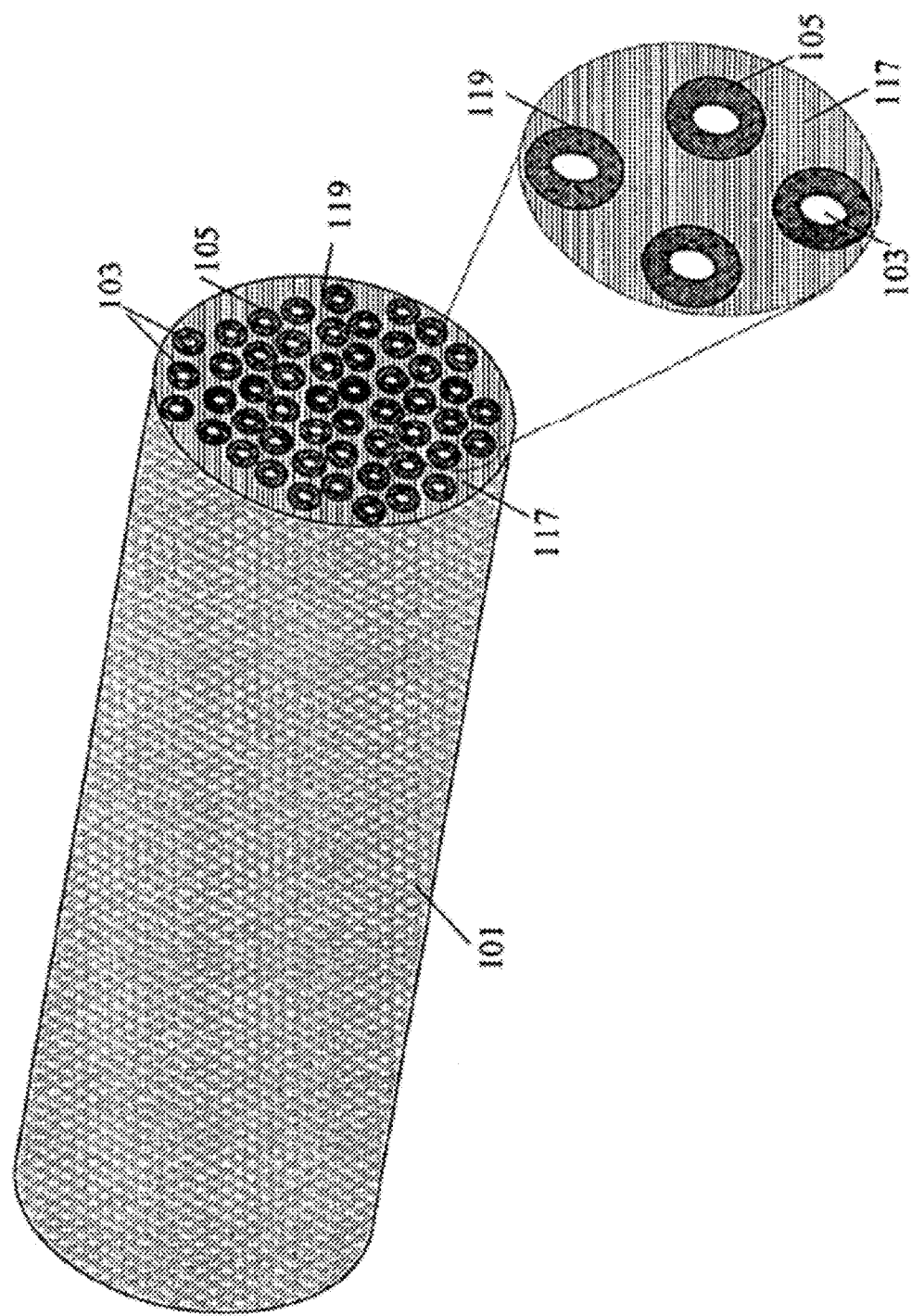
FIG. 9 hereof is another representation of an embodiment of a parallel channel contactor in the form of a coated monolith where the adsorbent layer is coated onto the channel wall.

FIG. 9 hereof is a representation of a parallel channel contactor 101 in the form of a coated monolith where an adsorbent layer is coated onto the walls of the flow channels of a preformed monolith. For the parallel channel contactors of FIG. 9, an extrusion process is used to form a monolith from a suitable non-adsorbent solid material, preferably a metal such as steel, a ceramic such as cordierite, or a carbon material. By the term "non-adsorbent solid material" we mean a solid material that is not to be used as the selective adsorbent for the parallel channel contactor. An effective amount and thickness of a ceramic or metallic glaze, or sol gel coating, 119 is preferably applied to effectively seal the channel walls of the monolith. Such glazes can be applied by slurry coating the channel walls, by any suitable conventional means, followed by firing the monolith in a kiln.

Another approach is to apply a sol gel to the channel walls followed by firing under conditions that densify the coating. It is also possible to use vacuum and pressure impregnation techniques to apply the glaze or sol gel to the channel walls. In such a case, the glaze or sol gel will penetrate into the pore structure of the monolith 117. In all cases, the glaze seals the wall of the channel such that gas flowing through the channel is not readily transmitted into the body of the monolith. An adsorbent layer 105 is then uniformly applied onto the sealed walls of the channels. The adsorbent layer 105 reduces the opening, or bore, of the channels, thus the flow channel 103 used in swing adsorption processes is the open channel left inside of the coating. These flow channels 103 can have channel gaps as previously defined. The adsorbent layer 105 can be applied as a coating, or layer, on the walls of the flow channels by any suitable method. Non-limiting examples of such methods include fluid phase coating techniques, such as slurry coating and slip coating. The coating solutions can include at least the microporous adsorbent or polymeric particles, a viscosifying agent such as polyvinyl alcohol, heat transfer (thermal mass) solids, and optionally a binder. The heat transfer solid may not be needed because the body of the monolith 101 can act to as its own heat transfer solid by storing and releasing heat in the different steps of the separation process cycle. In such a case, the heat diffuses through the adsorbent layer 105 and into the body of the monolith 101. If a viscosifying agent, such as polyvinyl alcohol, is used it is usually burns away when the coating is cured in a kiln. It can be advantageous to employ a binder such as colloidal silica or alumina to increase the mechanical strength of the fired coating. Mesopores or macropores will typically occupy from about 20 to about 40% of the volume of the cured coating. An effective amount of blocking agent is applied to complete the adsorbent layer for use. By effective amount of blocking agent we mean that amount needed to occupy enough of the mesopores and macropores such that the resulting coating contains less than about 20% of its pore volume in open mesopores and macropores.

If a hydrothermal film formation method is employed, the coating techniques used can be very similar to the way in which zeolite membranes are prepared. An example of a method for growing a zeolite layer is taught in U.S. Pat. No. 7,049,259, which is incorporated herein by reference. Zeolite layers grown by hydrothermal synthesis on supports often have cracks and grain boundaries that are mesopore and macropore in size. The volume of these pores is often less than about 10 volume % of the film thickness and there is often a characteristic distance, or gap, between cracks. Thus, as-grown films can often be used directly as an adsorbent layer without the need for a blocking agent.

Figure 10:
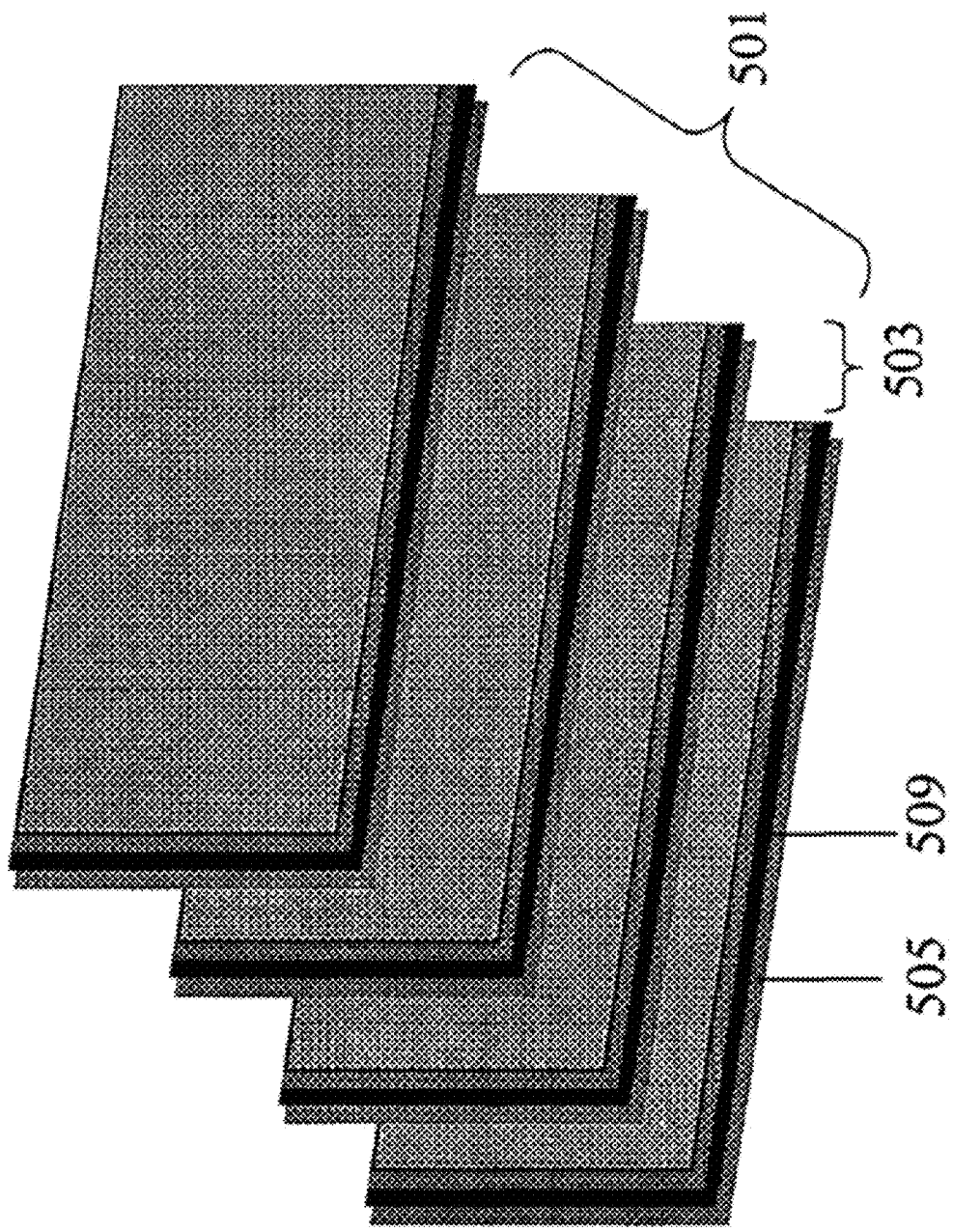
FIG. 10 hereof is a representation of an embodiment of a parallel contactor that is constructed from parallel laminate sheets.

FIG. 10 hereof is a representation of a parallel channel contactor of the present invention in which the parallel channels are formed from laminated sheets containing adsorbent material. Laminates, laminates of sheets, or laminates of corrugated sheets can be used in PSA RCPSA, PPSA or RCPPSA processes. Laminates of sheets are known in the art and are disclosed in U.S. patent applications US20060169142 A1 and U.S. Pat. No. 7,094,275 B2 which are incorporated herein by reference. When the adsorbent is coated onto a geometric structure or components of a geometric structure that are laminated together, the adsorbent can be applied using any suitable liquid phase coating techniques. Non-limiting examples of liquid phase coating techniques that can be used in the practice of the present invention include slurry coating, dip coating, slip coating, spin coating, hydrothermal film formation and hydrothermal growth. When the geometric structure is formed from a laminate, the laminate can be formed from any material to which the adsorbent of the present invention can be coated. The coating can be done before or after the material is laminated. In all these cases the adsorbent is coated onto a material that is used for the geometric shape of the contactor. Non-limiting examples of such materials include glass fibers, milled glass fiber, glass fiber cloth, fiber glass, fiber glass scrim, ceramic fibers, metallic woven wire mesh, expanded metal, embossed metal, surface-treated materials, including surface-treated metals, metal foil, metal mesh, carbon-fiber, cellulosic materials, polymeric materials, hollow fibers, metal foils, heat exchange surfaces, and combinations of these materials. Coated supports typically have two major opposing surfaces, and one or both of these surfaces can be coated with the adsorbent material. When the coated support is comprised of hollow fibers, the coating extends around the circumference of the fiber. Further support sheets may be individual, presized sheets, or they may be made of a continuous sheet of material. The thickness of the substrate, plus applied adsorbent or other materials (such as desiccant, catalyst, etc.), typically ranges from about 10 micrometers to about 2000 micrometers, more typically from about 150 micrometers to about 300 micrometers.

FIG. 10 hereof illustrates an exploded view of an embodiment of the present invention wherein a microporous adsorbent film 505 is on each of both faces of flat metal foils 509, which is preferably fabricated from a corrosion resistant metal such as stainless steel. The separate metal foils 509 with the adsorbent films 505 are fabricated to form a parallel channel contactor 501. Spacers of appropriate size may be placed between the metal foils during contactor fabrication so that the channel gap 503 is of a predetermined size. Preferably about half of the volume of the feed channels 503 are filled with a spacer that keeps the sheets substantially evenly spaced apart.

Metallic mesh supports can provide desirable thermal properties of high heat capacity and conductivity which "isothermalize" a PSA, RCPSA, PPSA or RCPPSA cycle to reduce temperature variations that degrade the process when conducted under more adiabatic conditions. Also, metal foils are manufactured with highly accurate thickness dimensional control. The metal foil may be composed of, without limitation, aluminum, steel, nickel, stainless steel or alloys thereof. Hence there is a need for a method to coat metal foils with a thin adsorbent layer of accurately controlled thickness, with necessary good adhesion. One method for doing this is by hydrothermal synthesis. Coating procedures used can be very similar to the way in which zeolite membranes are prepared as discussed above. Zeolite layers grown by hydrothermal synthesis on supports often have cracks which are mesopores and micropores. The volume of these pores is often less than about 10 volume % of the film thickness and there is often a characteristic distance between cracks. Another method of coating a metal foil is with thick film coating is slip casting, or doctor blading. An aqueous slurry of prefabricated zeolite particles, binder (for example colloidal silica or alumina), viscosifying agent such as a polymer like polyvinyl alcohol is cast for example onto a metal foil and fired to remove the polymer and cure the binder and zeolite. The product, after firing, is then a bound zeolite film on a metal foil typically containing about 30 to about 40 volume % voids. To make a suitable adsorbent layer, the voids are filled in a subsequent step by coating the bound zeolite film with a polymer or by introducing a liquid into the voids of the bound zeolite film. The final product, after filling the voids with a polymer or liquid, will be an adsorbent layer having the low mesoporosity and microporosity requirements of the present invention.

Another method for coating metal foils with prefabricated zeolite crystals, or microporous particles, is electrophoretic deposition (EPD). EPD is a technique for applying high quality coatings of uniform thickness to metal substrates. The method can be used to apply organic and inorganic particulate coatings on electrically conductive substrates. Slurry compositions containing prefabricated zeolites, or microporous particles, may be electrophoretically applied to a rigid support material, such as by using the method described in Bowie Keefer et al.'s prior Canadian patent application No. 2,306,311, entitled "Adsorbent Laminate Structure," which is incorporated herein by reference.

Some contactor geometric shapes will require that the adsorbent be applied to the channel surface in a layer using a colloidal binder material or that an entire geometric shape be comprised of the adsorbent plus colloidal binder and containing a plurality of parallel channels. When a colloidal binder is used, the selection of the colloidal material depends on the particular adsorbent used. Colloidal materials capable of functioning as a binder and/or which form a gel are preferred. Such colloidal materials include, without limitation, colloidal silica-based binders, colloidal alumina, colloidal zirconia, and mixtures of colloidal materials. "Colloidal silica" refers to a stable dispersion of discrete amorphous silicon dioxide particles having a particle size ranging from about 1 to about 100 nanometers. Suitable colloidal silica materials also can be surface modified, such as by surface modification with alumina. Another type of colloidal binder suitable for use herein include clay materials, such as palygorskite (also known as attapulgite), which are hydrated magnesium aluminum silicates. Also, inorganic binders may be inert; however, certain inorganic binders, such as clays, used with zeolite adsorbents may be converted in-situ from kaolin binders to zeolite so that the zeolite is self-bound with minimal inert material. In these bound structures, the voids between the colloidal particles form mesopores and the voids between the adsorbent particles form mesopores and/or macropores. A blocking agent can be applied to fill the majority of the mesoporosity and microporosity in these bound layers so that the adsorbent meets the open pore volume requirement of this invention. Organic binders used to bind activated carbon particulates in laminated structures may be pyrolyzed to form a useful carbonaceous adsorbent.

In some aspects, it would be valuable in the industry to enable the separation of certain contaminants from a natural gas feedstream. Some contaminants that are particularly of interest for removal are water ($H_2O$), nitrogen ($N_2$) and carbon dioxide ($CO_2$). The term "natural gas" or "natural gas feedstream" as used herein is meant to cover natural gas as extracted at the well head, natural gas which has been further processed, as well as natural gas for pipeline, industrial, commercial or residential use.

Of particular interest herein, is the use of the ITQ-55 material for removing contaminants from natural gas at wellheads (or after some amount of pre-processing) for further processing of the natural gas to meet the necessary specifications for putting the natural gas into a pipeline or for its intermediate or final industrial, commercial, or residential use. Of particular interest is the ability to remove one or more of these contaminants ($H_2O$, $N_2$, and/or $CO_2$) at the relatively high natural gas well processing pressure conditions. The removal of $H_2O$ from natural gas (i.e., in particular the methane and higher molecular weight hydrocarbon components of the natural gas) is important to the ability to further process the natural gas in processes where water is detrimental to the process (e.g., cryogenic separation of the hydrocarbons in the natural gas stream), as well as to meet certain specifications on the composition of the natural gas. The removal of $N_2$ from natural gas (i.e., in particular the methane and higher molecular weight hydrocarbon components of the natural gas) is important to remove this inert gas prior to further processing of the natural gas in processes which in turn substantially reduces overall processing facility capacity size requirements, as well as to meet certain specifications on the composition of the natural gas. The removal of $CO_2$ from natural gas (i.e., in particular the methane and higher molecular weight hydrocarbon components of the natural gas) is important to remove this inert gas prior to further processing of the natural gas in processes which reduces overall processing facility capacity size requirements, as well as to meet certain specifications on the composition of the natural gas.

It is of substantial benefit if the removal of these contaminants can be done at the relatively high pressures near the natural gas wellhead, as natural gas is usually produced at pressures ranging from 1,500 to 7,000 psi (10.3 MPa-48.3 MPa); and wherein the natural gas feedstream can be fed to the separations processes at over 300 psia (2.1 MPa), 500 psia (3.4 MPa), or even 1000 psia (6.9 MPa), such as up to about 2500 psia (about 17 Mpa) or more. There are few, if any, materials that can operate reliably and effectively to separate these contaminants from methane and other higher molecular weight hydrocarbons under PSA, PPSA, RCPSA, RCPPSA, or TSA (or combined cycle processes such as PSA/TSA, PPSA/TSA, RCPSA/TSA, and RCPPSA/TSA, wherein steps from each process are combined in the overall cycle) cycle conditions at these high pressure conditions. Some of the benefits of being to perform these separations at these high pressures include smaller equipment size (due to the smaller gas volume at high pressures) and the ability to use the product streams from these separations processes in further processing or pipeline transportation without the need for, or the reduced need for, equipment and energy required to repressurize the resulting separations product stream(s) for such further use.

In embodiments herein, the ITQ-55 material can be used in PSA, PPSA, RCPSA, RCPPSA, TSA or combined cycle conditions at natural gas feed pressures in the range of about 5 to about 5.000 psia (about 0.03 MPa to about 35 MPa), about 50 to about 3,000 psia (about 0.34 MPa to about 21 MPa), about 100 to about 2,000 psia (about 0.69 MPa to about 14 MPa), about 250 to about 1,500 psia (about 1.7 MPa to about 10 MPa), over 50 psia (0.34 MPa), over 250 psia (1.7 MPa), over 500 psia (3.4 MPa), or over 1000 psia (6.9 MPa). In embodiments, operating natural gas feed temperatures may be from about 0 to about 750° F. (about −18° C. to about 399° C.), about 100 to about 600° F. (about 38° C. to about 316° C.), or about 150 to about 500° F. (about 66° C. to about 260° C.).

Figure 17:
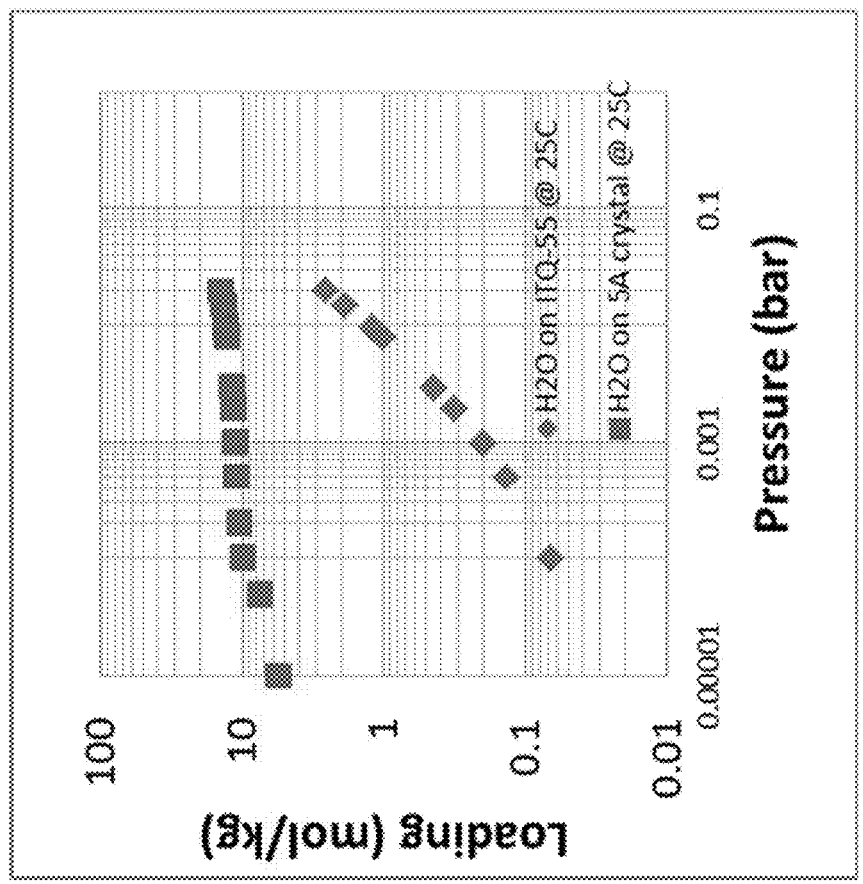
FIG. 17 shows the equilibrium loading of $H_2O$ for ITQ-55 in comparison with zeolite 5A.

As can be seen from FIG. 17, and as described elsewhere herein, the ITQ-55 material shows an exponentially increasing capacity for water at higher pressures, while other materials considered for this use (i.e., zeolite 5A) appear to have only very small increases in water capacity at higher pressures. As is discussed elsewhere herein, ITQ-55 has a very high adsorption affinity for each of these contaminants ($H_2O$, $N_2$, and $CO_2$) while at the same time exhibiting very low adsorption of methane ($CH_4$) or higher molecular weight hydrocarbons. The ITQ-55 material can be used in these associated swing processes in either an equilibrium or kinetic separations regime. In these processes, ITQ-55 in its substantially pure silica may be used, or the ITQ-55 utilized may possess a Si/Al ratio from about 10:1 to about 1000:1, or about 50:1 to about 500:1.

In some embodiments for processing a natural gas feedstream, the PSA, PPSA, RCPSA, RCPPSA, TSA or combined cycle conditions described herein may be operated with regimes wherein the Selectivity (as defined prior as $U_A/U_B$; where $U_A > U_B$) is greater than about 5, is greater than about 10, greater than about 50, or even greater than about 100, and A is $H_2O$ and B is methane and higher molecular weight hydrocarbons. In other embodiments for processing a natural gas feedstream, the PSA, PPSA, RCPSA, RCPPSA, TSA or combined cycle conditions described herein may be operated with regimes wherein the Selectivity (as defined prior as $U_A/U_B$; where $U_A > U_B$) is greater than about 5, is greater than about 10, greater than about 50, or even greater than about 100, and A is $N_2$ and B is methane and higher molecular weight hydrocarbons. In still other embodiments for processing a natural gas feedstream, the PSA, PPSA, RCPSA, RCPPSA, TSA or combined cycle conditions described herein may be operated with regimes wherein the Selectivity (as defined prior as $U_A/U_B$; where $U_A > U_B$) is greater than about 5, is greater than about 10, greater than about 50, or even greater than about 100, and A is $CO_2$ and B is methane and higher molecular weight hydrocarbons.

Membrane Separations

In some aspects, the zeolite ITQ-55 can be used as part of a membrane. An example of a membrane can be a layer comprising a supported inorganic layer comprising contiguous particles of a crystalline molecular sieve. Another example of a membrane can be a self-supported layer of zeolite crystal particles. The particles having a mean particle size within the range of from 20 nm to 1 µm. In one type of aspect, the mean particle size can optionally be within the range of from 20 to 500 nm, preferably it is within the range of from 20 to 300 nm and most preferably within the range of from 20 to 200 nm. Alternatively, the mean particle size can advantageously be such that at least 5% of the unit cells of the crystal are at the crystal surface. Optionally, the particles can have a mean particle size within the range of from 20 to 200 nm.

In such an aspect, the layer can comprises molecular sieve particles optionally coated with skin of a different material; these are identifiable as individual particles (although they may be intergrown as indicated below) by electron microscopy. The layer, at least after activation, is mechanically cohesive and rigid. Within the interstices between the particles in this rigid layer, there may exist a plethora of non-molecular sieve pores, which may be open, or partially open, to permit passage of material through or within the layer, or may be completely sealed, permitting passage through the layer only through the pores in the particles. Advantageously, the particle size distribution is such that 95% of the particles have a size within ±33% of the mean, preferably 95% are within ±15% of the mean, preferably +10% of the mean and most preferably 95% are within ±7.5% of the mean.

It will be understood that the particle size of the molecular sieve material forming the layer may vary continuously or stepwise with distance from the support. In such a case, the requirement for uniformity is met if the particle size distribution is within the defined limit at one given distance from the support, although advantageously the particle size distribution will be within the defined limit at each given distance from the support. The use of molecular sieve crystals of small particle size and preferably of homogeneous size distribution facilitates the manufacture of a three-dimensional structure which may if desired be thin but which is still of controlled thickness.

In some aspects, the particles of ITQ-55 can be contiguous, i.e., substantially every particle is in contact with one or more of its neighbors as evidenced by electron microscopy preferably high resolution microscopy, although not necessarily in contact with all its closest neighbors. Such contact may be such in some embodiments that neighboring crystal particles are intergrown, provided they retain their identity as individual crystalline particles. Advantageously, the resulting three dimensional structure is grain-supported, rather than matrix-supported, in the embodiments where the layer does not consist essentially of the crystalline molecular sieve particles. In a preferred embodiment, the particles in the layer are closely packed.

A layer may optionally be constructed to contain passageways between the particles that provide a non-molecular sieve pore structure through or into the layer. Such a layer may consist essentially of the particles or may contain another component, which may be loosely termed a matrix which, while surrounding the particles, does not so completely or closely do so that all pathways round the particles are closed. Alternatively, the layer may be constructed so that a matrix present completely closes such pathways, with the result that the only path through or into the layer is through the particles themselves. It will be understood that references herein to the support of a layer include both continuous and discontinuous supports.

References to particle size are throughout this specification to the longest dimension of the particle and particle sizes are as measured by direct imaging with electron microscopy. Particle size distribution may be determined by inspection of scanning or transmission electron micrograph images preferably on lattice images, and analyzing an appropriately sized population of particles for particle size.

A supported layer according to the invention may be manufactured in a number of different ways. One option can be making a layer by deposition on a support from a colloidal zeolite suspension obtainable by preparing an aqueous synthesis mixture comprising a source of silica and an organic structure directing agent in a proportion sufficient to effect substantially complete dissolution of the silica source in the mixture at the boiling temperature of the mixture, and crystallization from the synthesis mixture. The synthesis mixture will contain, in addition, a source of the other component or components, if any, in the zeolite. In other aspects, one or more of the techniques described above for formation of an adsorbent structure can also be suitable for formation of a membrane structure.

The thickness of the molecular sieve layer can be, for example, within the range of 0.1 to 20 m, or 0.1 to 15 m, or from 0.1 to 2 µm. Advantageously, the thickness of the layer and the particle size of the molecular sieve are such that the layer thickness is at least twice the particle size, resulting in a layer several particles thick rather than a monolayer of particles. Advantageously, the layer is substantially free of pinholes, i.e., substantially free from apertures of greatest dimension greater than 0.1 µm. Advantageously, at most 0.1% and preferably at most 0.0001% of the surface area is occupied by such apertures.

The layer support may be either non-porous or, preferably, porous, and may be continuous or particulate. As examples of non-porous supports there may be mentioned glass, fused quartz, and silica, silicon, dense ceramic, for example, clay, and metals. As examples of porous supports, there may be mentioned porous glass, porous carbon, porous ceramics, sintered porous metals, e.g., steel or nickel (which have pore sizes typically within the range of 0.2 to 15 µm), and, especially, an inorganic oxide. e.g., alpha-alumina, titania, an alumina/zirconia mixture, or Cordierite. At the surface in contact with the layer, the support may have pores of dimensions up to 50 times the layer thickness, but preferably the pore dimensions are comparable to the layer thickness.

Still another option for forming the membrane layer can be to have a hybrid or composite layer. An example of a hybrid membrane layer can be particles of zeolite ITQ-55 mixed with polymer(s) and spun as hollow fibers. Optionally, such fibers can be thermally converted to carbonaceous materials to form a layer composed of ITQ-55 and carbon composite fibers. As an example, hollow fiber membranes can be produced through a hollow fiber spinning process. One or more polymer solutions can be extruded with bore fluid through an annular die into an aqueous quench bath. Optionally, two or more polymer solutions can be co-extruded to form a composite fiber. At least one of the polymer solutions can also include ITQ-55 crystal particles, so that the ITQ-55 is incorporated into the hollow fiber structure. When the nascent fiber enters an aqueous quench bath, solvents diffuse from fibers into the quench bath while water from the quench bath diffuses into the fibers, which causes phase separation to occur. Open porous substructures can be formed during this phase separation process. A simple subsequent standard process to prepare hollow fiber modules, as is known in the industry, can then be used.

The layer may, and for many uses advantageously does, consist essentially of the molecular sieve material, or it may be a composite of the molecular sieve material and intercalating material which is also inorganic. The intercalating material may be the material of the support. If the layer is a composite it may, as indicated above, contain macropores and/or micropores, bounded by molecular sieve portions, by portions of intercalating material, or by both molecular sieve and intercalating material. The material may be applied to the support simultaneously with or after deposition of the molecular sieve, and may be applied, for example, by a sol-gel process followed by thermal curing. Suitable materials include, for example, inorganic oxides, e.g., silica, alumina, and titania. The intercalating material is advantageously present in sufficiently low a proportion of the total material of the layer that the molecular sieve crystals remain contiguous.

In another example of a process for the manufacture of a layer comprising a crystalline molecular sieve on a porous support, the layer can be formed by pre-treating the porous support to form at a surface thereof a barrier layer, and applying to the support a reaction mixture comprising a colloidal suspension of molecular sieve crystals, having a mean particle size of at most 100 nm and advantageously a particle size distribution such that at least 95% of the particles have a size within t 15%, preferably ±10%, more preferably within ±7.5%, of the mean, colloidal silica and optionally an organic structure directing agent, to form a supported molecular sieve layer, and if desired or required activating the resulting layer. Activation removes the template and can be achieved by calcination, ozone treatment, plasma treatment or chemical extraction such as acid extraction. The invention also provides a supported layer formed by the process.

The barrier layer functions to prevent the water in the aqueous reaction mixture from preferentially entering the pores of the support to an extent such that the silica and zeolite particles form a thick gel layer on the support. The barrier layer may be temporary or permanent. As a temporary layer, there may be mentioned an impregnating fluid that is capable of being retained in the pores during application of the reaction mixture, and readily removed after such application and any subsequent treatment.

Spin coating can be still another advantageous technique for applying the reaction mixture to the support according to this and other aspects of the invention. The impregnating fluid should accordingly be one that will be retained in the pores during spinning if that technique is used; accordingly the rate of rotation, pore size, and physical properties of the fluid need to be taken into account in choosing the fluid. The fluid should also be compatible with the reaction mixture, for example if the reaction mixture is polar, the barrier fluid should also be polar. As the reaction mixture is advantageously an aqueous reaction mixture, water is advantageously used as the barrier layer. To improve penetration, the fluid barrier may be applied at reduced pressure or elevated temperature. If spin-coating is used, the support treated with the barrier fluid is advantageously spun for a time and at a rate that will remove excess surface fluid, but not remove fluid from the pores. Premature evaporation of fluid from the outermost pores during treatment may be prevented by providing an atmosphere saturated with the liquid vapor.

During spin-coating, the viscosity of the reaction mixture and the spin rate can control coating thickness. The mixture is advantageously first contacted with the stationary support, then after a short contact time the support is spun at the desired rate. After spinning, the silica is advantageously aged by retaining the supported layer in a high humidity environment, and subsequently dried, advantageously first at room temperature and then in an oven.

As still another option, there is provided a process for the manufacture of a layer comprising a crystalline molecular sieve on a porous support which comprises applying to the support by dip-coating a colloidal suspension of molecular sieve crystals, having a mean particle size of at most 100 nm and advantageously a particle size distribution such that at least 95% of the particles have a size within ±15%, preferably ±10%, more preferably ±7.5%, of the mean, drying the resulting gel on the support and if desired or required activating the resulting layer. Still another option can include synthesizing molecular sieve crystals in situ on a support.

Storage Applications

In various aspects, an adsorbent structure as described above can also be used for storage of fluids. The initial adsorption of a fluid or fluid component into an adsorbent structure can be performed in any convenient manner, such as according to the adsorption processes described above. Optionally, the adsorption of fluids for storage can be performed using an input gas substantially composed of a single component, as opposed to also performing a separation during adsorption.

In some aspects, after a fluid is adsorbed in an adsorbent structure, the adsorbent structure can be maintained at a temperature and/or pressure similar to the conditions used during the adsorption. In other aspects, at least one of the temperature and/or the pressure can be modified to assist with maintaining the fluid in the adsorbent structure. For example, after adsorbing a fluid at a first temperature, the temperature of the adsorbent structure can be reduced to assist with maintaining the fluid within the adsorbent structure.

The conditions for maintaining an adsorbed fluid within the adsorbent structure can depend in part on the nature of the adsorbed component. For example, hydrogen can be readily adsorbed by ITQ-55, but hydrogen can likely also desorb from ITQ-55 at a wide range of temperatures. In order to maintain a desired stored amount of hydrogen within an adsorbent structure, an exterior pressure of hydrogen may be needed, so that the hydrogen outside of the adsorbent structure is in equilibrium with the hydrogen inside of the adsorbent structure. This situation can be in contrast to storage of methane, ethylene, methanol, ethane, or another hydrocarbon/organic compound in an adsorbent structure. Hydrocarbons and organic compounds can have a limited ability to enter into and/or diffuse within the pore structure of ITQ-55 at lower temperatures and/or pressures. As a result, an amount of hydrocarbon and/or organic compound can be stored within an adsorbent structure based on ITQ-55 without having a corresponding equilibrium amount of the stored component outside of the adsorbent structure.

During an initial adsorption step, a fluid component can be adsorbed into the adsorbent structure. The conditions during adsorption can include, for example, a) a temperature of at least about 325 K, or at least about 375 K, or at least about 425 K, or at least about 475 K; b) a pressure of at least about 100 bar (10 MPaa), or at least about 300 bar (30 MPaa), or at least about 500 bar (50 MPaa), or at least about 700 bar (70 MPaa); or c) a combination thereof. Without being bound by any particular theory, the elevated temperature and/or pressure can allow for introduction of an elevated loading of an organic component into the adsorbent structure.

After loading of the adsorbent structure, the temperature and/or pressure can be reduced. In aspects where loading of the adsorbent structure is performed at an elevated pressure, the pressure can be reduced to about 100 bar (10 MPaa) or less, or about 10 bar (1 MPaa) or less, or about 2 bar (0.2 MPaa) or less, or about 1 bar (0.1 MPaa) or less. In aspects where loading of the adsorbent structure is performed at an elevated temperature, the temperature can be reduced to about 325 K or less, or about 300 K or less, or about 275 K or less, or about 250 K or less, or about 225 K or less, or about 200 K or less. In aspects where both the temperature and pressure are elevated during loading, the temperature can optionally be reduced first, and then the pressure can be reduced. After reducing the temperature and/or pressure, some desorption of the adsorbed component can occur. However, based on the reduced temperature and/or pressure conditions, a portion of the component can remain kinetically trapped within the adsorbent structure. This can allow the adsorbent structure to retain an amount of the fluid component within the adsorbent structure, even though the atmosphere outside of the adsorbent may no longer contain the adsorbed component. The loading retained within the adsorbent can correspond to a percentage of the loading that was achieved during adsorption, such as at least about 10 wt % of the loading during adsorption, or at least about 20 wt %, or at least about 30 wt %, or at least about 40 wt %, or at least about 50 wt %, or at least about 60 wt %. The adsorbent structure can then optionally be transported under the reduced temperature and/or pressure conditions.

After storage for a desired amount of time, the temperature can be increased to allow the adsorbed component to exit from the adsorbent structure. This can allow the adsorbed component, corresponding to a fuel and/or potential reactant, to be stored and optionally transported under less severe conditions. In other words, the temperature and/or pressure required for storage of the adsorbed component in the adsorbent structure can be reduced relative to the conditions required for storing the adsorbed component in the absence of the adsorbent structure. The amount of storage time can be any convenient amount of time, such as at least a day, or at least a month, and up to a year or more.

Catalysis Process and Method of Use

In addition to separations, zeolite ITQ-55 can also be suitable for use as a catalyst for a variety of reactions. In some aspects, ITQ-55 can be suitable for catalysis of reactions that can generally be catalyzed by zeolites having an 8-member ring as the largest ring size. For example, the selective catalytic reduction of nitrogen oxides, optionally in the presence of ammonia, is a reaction that can be catalyzed using 8-member ring zeolites.

Other examples of suitable catalytic uses of zeolite ITQ-55 can potentially include, but are not limited to, (a) hydrocracking of heavy petroleum residual feedstocks, cyclic stocks and other hydrocrackate charge stocks, normally in the presence of a hydrogenation component is selected from Groups 6 and 8 to 10 of the Periodic Table of Elements; (b) dewaxing, including isomerization dewaxing, to selectively remove straight chain paraffins from hydrocarbon feedstocks typically boiling above 177° C., including raffinates and lubricating oil basestocks; (c) catalytic cracking of hydrocarbon feedstocks, such as naphthas, gas oils and residual oils, normally in the presence of a large pore cracking catalyst, such as zeolite Y; (d) oligomerization of straight and branched chain olefins having from about 2 to 21, preferably 2 to 5 carbon atoms, to produce medium to heavy olefins which are useful for both fuels, i.e., gasoline or a gasoline blending stock, and chemicals; (e) isomerization of olefins, particularly olefins having 4 to 6 carbon atoms, and especially normal butene to produce iso-olefins; (f) upgrading of lower alkanes, such as methane, to higher hydrocarbons, such as ethylene and benzene; (g) disproportionation of alkylaromatic hydrocarbons, such as toluene, to produce dialkylaromatic hydrocarbons, such as xylenes; (h) alkylation of aromatic hydrocarbons, such as benzene, with olefins, such as ethylene and propylene, to produce ethylbenzene and cumene; (i) isomerization of dialkylaromatic hydrocarbons, such as xylenes, (j) catalytic reduction of nitrogen oxides, (k) synthesis of monoalkylamines and dialkylamines, (l) conversion of methanol to dimethyl ether, (m) conversion of methanol (and/or other oxygenates) to olefins, and (n) conversion of methanol (and/or other oxygenates) to aromatics.

For at least some of the above reaction types, effective catalysis of the reaction by zeolite ITQ-55 can involve at least partial entry of one or more reactants into the pore structure of the zeolite. The pore structure of zeolite ITQ-55 includes 8-member ring channels. The 8-member ring channels include a minimum pore channel size in the pore network of 5.9 Angstroms x 2.1 Angstroms at ambient temperature. This minimum pore channel size can limit the types of compounds that can effectively enter and/or pass through the pore network. However, the 8-member ring that provides the minimum size is also believed to have flexibility. This flexibility can allow the 8-member ring to deform, such as due to thermal fluctuations and/or due to fluctuations induced at elevated pressures, which can lead to a potential temporary increase in the size of the pore channel. Without being bound by any particular theory, it is believed that the flexibility of the 8-member ring defining the size of the pore channel can allow for additional tuning of catalysis of various reactions based on temperature and/or pressure.

Additionally or alternately, the particle size of ITQ-55 crystals used in an adsorbent structure or membrane structure can have an impact on the ability of the adsorbent structure or membrane structure to perform catalysis. As one example, the particle size of the ITQ-55 crystals can have an influence on the amount of "dead space" that is present at the surface and/or within the interior of an adsorbent structure or membrane structure. Mathematically, the packing density of a collection of hard spheres of similar size is dependent on the radius of the spheres. For a collection of hard spheres, the larger the average radius, the larger the size of the spaces or gaps between the hard spheres. Without being bound by any particular theory, it is believed that for a collection of ITQ-55 crystals of similar size, the size of the voids or dead spaces created after close packing of crystals can be related to the average particle size. Having a smaller particle size can reduce such dead space, thus providing an increased pore surface area for accepting fluid components for catalysis.

Additionally or alternately, the composition of ITQ-55 crystals used can have an impact on the catalytic properties of a catalyst. In some aspects, ITQ-55 can be synthesized to have a framework structure composed of primarily silicon and oxygen. In other aspects, a portion of the framework atoms in the ITQ-55 structure can be replaced with other elements. For example, a portion of the silicon in the framework structure can be replaced with atoms from a different group in the periodic table, such as Al, P, and/or B. In an aspect, a portion of the silicon in the framework structure can be replaced with Al. As another example, a portion of the silicon in the framework can be replaced with atoms from a different row of the periodic table, such as Ge or P. Such composition variations can modify the size of the pores within the crystal structure and/or modify the affinity of the ITQ-55 relative to one or more potential reactants, which can influence the ability to catalyze a reaction. Additionally or alternately, such composition variations can also alter the properties of the ITQ-55 crystals, such as the acidity of the crystals, which can also influence catalytic activity.

When used as a catalyst, the ITQ-55 crystals can be incorporated into a catalyst by any convenient method. In some aspects, extruded catalyst particles can be a convenient catalyst form. Such extruded catalyst particles can include the zeolite crystals as well as an optional binder. Optionally, catalytic metals can be added to such catalyst particles, such as by impregnation. For catalyst particles that include an optional binder, the optional binder can be present in any convenient amount, such as from about 10 wt % to about 90 wt %, more typically from about 30 wt % to about 70 wt %. Suitable binders can include, but are not limited to, metal oxides such as silica, alumina, silica-alumina, zirconia, titania, and combinations thereof. Suitable catalytic metals can include, but are not limited to, transition metals. Examples of suitable transition metals include Group VI metals (Mo, W), Group VIII metals (Co, Ni, Pt, Pd, Fe, Ir), and combinations thereof. Such catalytic metals can be present in an amount of about 0.1 wt % to about 40 wt % relative to the weight of the catalyst particles. Additionally or alternately, in some aspects, catalyst particles (for example, supported catalyst particles) that include ITQ-55 crystals can further include one or more additional zeolites, such as molecular sieves having the MFI framework structure (e.g., ZSM-5), the FAU framework structure (e.g., zeolite Y), or a molecular sieve based on any other convenient framework structure.

In other aspects, a monolith or other large structure containing and/or composed of the zeolite crystals may be used. For example, any of the adsorbent and/or membrane structures described above can be suitable for use in some catalysis applications. Optionally, such structures can also include other catalytic metals, such as other catalytic metals impregnated on the surface of the structure.

As a specific example, zeolite ITQ-55 can be useful in the catalytic conversion of oxygenates to one or more olefins, particularly ethylene and propylene. As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In an oxygenate conversion process, a feedstock comprising an organic oxygenate, optionally, with one or more diluents, is contacted in the vapor phase in a reaction zone with a catalyst comprising the molecular sieve of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

It is noted that both methanol and dimethyl ether can have a kinetic diameter that is at least similar to methane. At temperatures near 25° C. and pressures near 0.1 MPaa, methanol and/or dimethyl ether can have a limited ability to enter the pore structure of zeolite ITQ-55. However, as temperature and/or pressure is increased, methanol and dimethyl ether can have an increasing ability to enter the pore structure of ITQ-55, thus allowing for increasing ability to catalyze the oxygenate to olefin reaction. Still further increases in temperature and/or pressure may allow for conversion of other oxygenates, such as ethanol. As a result, variations in temperature and/or pressure during oxygenate to olefin conversion can allow for tuning of the conversion reaction.

As an example, an initial loading of methanol or dimethyl ether can be introduced into a catalyst structure and/or catalyst particles comprising ITQ-55 at a first pressure. At the first pressure, the pressure of methanol and/or dimethyl ether can be sufficient to load the catalyst structure and/or catalyst particles. The pressure can then be reduced while maintaining a temperature where the methanol and/or dimethyl ether has a reduced or minimal amount of diffusion within the ITQ-55 pore structure. This can result in an oxygenate being confined within a constrained pore structure that may allow for selective production of ethylene at increased yield. Optionally, methane can be used in place of methanol and/or dimethyl ether, along with a suitable oxidant such as water or molecular oxygen.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example, from about 250° C. to about 800° C., including from about 250° C. to about 750° C., conveniently from about 300° C. to about 650° C., typically from about 350° C. to about 600° C., and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPaa. Conveniently, the pressure is in the range of from about 7 kPa to about 5 MPaa, such as in the range of from about 50 kPa to about 1 MPaa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate, however, light olefins such as ethylene still may form.

The process can be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock can be used in the oxygenate conversion process. WHSV is defined as weight of feed (excluding diluent) per hour per weight of a total reaction volume of molecular sieve catalyst (excluding inerts and/or fillers). The VWHSV generally should be in the range of from about 0.01 $hr^{-1}$ to about 500 $hr^{-1}$, such as in the range of from about 0.5 $hr^{-1}$ to about 300 $hr^{-1}$, for example, in the range of from about 0.1 $hr^{-1}$ to about 200 $hr^{-1}$.

A practical embodiment of a reactor system for the oxygenate conversion process is a circulating fluid-bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

Because the catalyst in such an oxygenate to olefin process must be regenerated frequently, the reactor should allow easy removal of a portion of the catalyst to a regenerator, where the catalyst is subjected to a regeneration medium, such as a gas comprising oxygen, for example, air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

As another example, catalysts that are effective for conversion of methanol (and/or other oxygenates) to olefins are often also effective for conversion of methanol and/or other oxygenates to aromatic compounds. Reaction conditions for formation of aromatics from methanol are often similar to reaction conditions for formation of olefins, with aromatics formation sometimes being favored by conditions that tend toward higher severity. Thus, in some aspects, conditions that can favor aromatics formation can include lower WHSV values, higher temperatures, and/or higher partial pressures of reactants. Aromatic products can generally include $C_6$ to $C_{11}$ aromatics, with $C_6$, $C_7$, and/or $C_8$ aromatics often being preferred. For example, preferred products can include benzene ($C_6$), toluene ($C_7$), and/or xylene ($C_8$).

This invention is illustrated by means of the following examples that do not seek to be restrictive thereof.

EXAMPLES

Example 1. Preparation of the $N^2,N^2,N^2,N^5,N^5,N^5$, 3a,6a-octamethyloctahydropentalene-2,5-diammonium dihydroxide To a recently prepared and thoroughly mixed solution of 5.6 g $NaHCO_3$ in 360.0 mL of $H_2O$ (pH=8) is added 48.2 mL (526.3 mmol) of dimethyl 1,3-acetonedicarboxylate followed by 23.0 mL (263.2 mmol) of 2,3-butanodione. The mixture remains under continuous stirring for 72 hr. After this period the abundant precipitate obtained is filtered under vacuum and cooled in a bath of ice, being acidified to pH=5 with HCl (5%). The raw precipitate is extracted three times with $CHCl_3$, washing the set of organic phases with brine and drying them on MgSO4. The mixture is filtered through folded filter and the filtrate obtained concentrated under vacuum and used in the following stage without additional purification.

The resultant solid is suspended in a mixture of 300.00 mL of HCl (1M) and 30.0 mL of glacial acetic acid and thereafter heated under reflux for 24 hr. The resulting mixture is cooled first to room temperature and then in an ice bath, extracting thereafter five time with $CH_2Cl_2$, drying the set of organic phases over $MgSO_4$. The rough precipitate obtained is filtered through folded filter and concentrated under vacuum obtaining 32.7 g (75%) of the desired diketone, 3a,6a-dimethyltetrahydropentalene-2,5(1H,3H)-dione.

This diketone is transformed into the corresponding diamine by means of the method that is described below. 350.0 mL of a solution 1.0 M of dimethylamine in methanol is cooled in an ice bath and onto it is dripped a solution of HCl 5 N in MeOH until obtaining pH=7-8. Then 16.7 g is added (100.7 mmol) of the previously prepared diketone dissolved in the minimum possible quantity of MeOH, followed by 10.2 g (161.2 mmol) of $NaBH_3CN$. The temperature is allowed to rise to room temperature and remains under continuous stirring for 72 hr.

The possible excess of $NaBH_3CN$ is neutralized by adding HCl 5 N in MeOH until reaching pH=2, displacing the HCN formed with a stream of $N_2$ until a saturated solution in KOH. The mixture is partially concentrated under vacuum and the rough resultant is basified with a solution of KOH (25%) until reaching pH=12 and it is saturated with NaCl. The rough resultant obtained is extracted three times with $CH_2Cl_2$, drying the set of organic phases on $MgSO_4$. It is concentrated under vacuum obtaining 21.4 g (95%) of the desired diamine, $N^2,N^2,N^5,N^5$,3a,6a hexamethyloctahydropentalene-2,5-diamine.

Subsequently, the diamine is transformed into the quaternary diammonium ketone. For that, 21.6 g of the previously obtained diamine is dissolved in 100.0 mL of MeOH and to it is added slowly, by means of a compensated pressure funnel, 45.0 mL (722.8 mmol) of $CH_3I$ diluted in 40.0 mL of MeOH. Almost immediately a yellowish precipitate appears. The mixture remains under continuous stirring for 72 hr and then 45.0 ml is added (722.8 mmol) of $CH_3I$ remaining under continuous stirring until completing one week. The precipitate obtained is filtered under vacuum washing with abundant diethyl ether, providing 37.1 g of the quaternary ammonium salt desired in iodide form, $N^2,N^2,N^2,N^5,N^5,N^5$,3a,6a-octamethyloctahydropentalene-2,5-diammonium diiodide.

The filtrate is concentrated under vacuum and the viscous solid obtained is washed with abundant acetone, a new precipitate appears that after filtering and drying under vacuum provides another 2.0 g of the ammonium salt (80%).

The iodide of the cation is exchanged by hydroxide using an ionic exchange resin in accordance with the following method: 20 g (44 mmol) of iodide of the cation ($RI_2$) is dissolved in water. To the solution obtained is added 89 g of Dowex SBR resin and it remains under stirring until the following day. Subsequently, it is filtered, it is washed with distilled water and a solution of $N^2,N^2,N^2,N^5,N^5,N^5$,3a,6a dihydroxide is obtained-octamethyloctahydropentalene-2,5-diammonium (R(OH)2) that is titrated with HCl (aq.), using phenolphthalein as indicator, an efficiency being obtained in the exchange greater than 92%.

The final solution contains 0.47 equivalent of hydroxide per 1000 g of solution.

Example 2. Zeolite Preparation ITQ-55

6 g is added of an aqueous solution of colloidal silica at 40% (Ludox ACE-40) to 42.5 g of a solution of 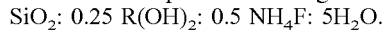 $N^2.N^2,N^2,N^5,N^5,N^5$,3a,6a-octamethyloctahydropentalene 2,5-diammonium dihydroxide-$(R(OH)_2)$ that contains 0.47 equivalent of hydroxide in 1000 g. The mixture is left evaporating under stirring until complete elimination of the surplus water until reaching the final composition that is indicated. Finally, a solution of 0.74 g of ammonium fluoride is added in 2.5 g of water. The composition of the gel is:

$SiO_2$: 0.25 $R(OH)_2$: 0.5 $NH_4F$: $5H_2O$.

The mixture obtained is introduced in an autoclave provided with an internal sleeve of polytetrafluorethylene and is warmed at 150° C. over 10 days in an electrical furnace provided with a rotation system. The X-ray diffractogram of the solid obtained on filtering, washing with distilled water and drying at 100° C. is shown in FIG. 1 and presents the listing of the most characteristic peaks that appears in the Table III. The calcining at 800° C. in air for 3 hours allows eliminating the occluded organic species. The X-ray diffraction pattern of the calcined zeolite ITQ-55 is shown in FIG. 2 and presents the most characteristic peaks that appears in Table IV and indicates that the material is stable during this process.

Example 3. Zeolite Preparation ITQ-55

8 g of tetraethylorthosilicate (TEOS) is added to 40.8 g of a solution of $N^2,N^2,N^2,N^5,N^5,N^5$,3a,6a-octamethyloctahydropentalene-2,5-diammonium dihydroxide (R(OH)2) that contains 0.47 equivalent of hydroxide in 1000 g. The mixture is left evaporating under stirring until complete elimination of the ethanol coming from the hydrolysis of the TEOS plus the quantity of water necessary until reaching the final composition that is indicated. Finally, 0.77 g of a solution of hydrofluoric acid is added (50% of HF by weight). The composition of the gel is:

$SiO_2$: 0.25 $R(OH)_2$: 0.5 HF: $5H_2O$.

The mixture obtained is introduced into a autoclave provided with an internal sleeve of polytetrafluoroethylene and is warmed at 15 over 10 days in an electrical furnace provided with a rotation system. The solid obtained on filtering, washing with distilled water and drying at 100° C. is ITQ-55.

Example 4. Zeolite Preparation ITQ-55

6 g is added from a aqueous solution of colloidal silica at 40% (Ludox ACE-40) 42.5 g of a solution of $N^2,N^2,N^2,N^5,N^5,N^5$,3a,6a-octamethyloctahydropentalene-2,5-diammonium (R(OH)2) dihydroxide that contains 0.47 equivalent of hydroxide in 1000 g. Thereafter 0.14 g of aluminum hydroxide is added (57% $Al_2O_3$) and the mixture is left evaporating under stirring until complete elimination of the surplus water until reaching the final composition that is indicated. Finally, a solution of 0.74 g of ammonium fluoride is added in 2.5 g of water. The composition of the gel is:

$SiO_2$: 0.02 $Al_2O_3$: 0.25 $R(OH)_2$: 0.5 $NH_4F$: $5H_2O$.

Figure 3:
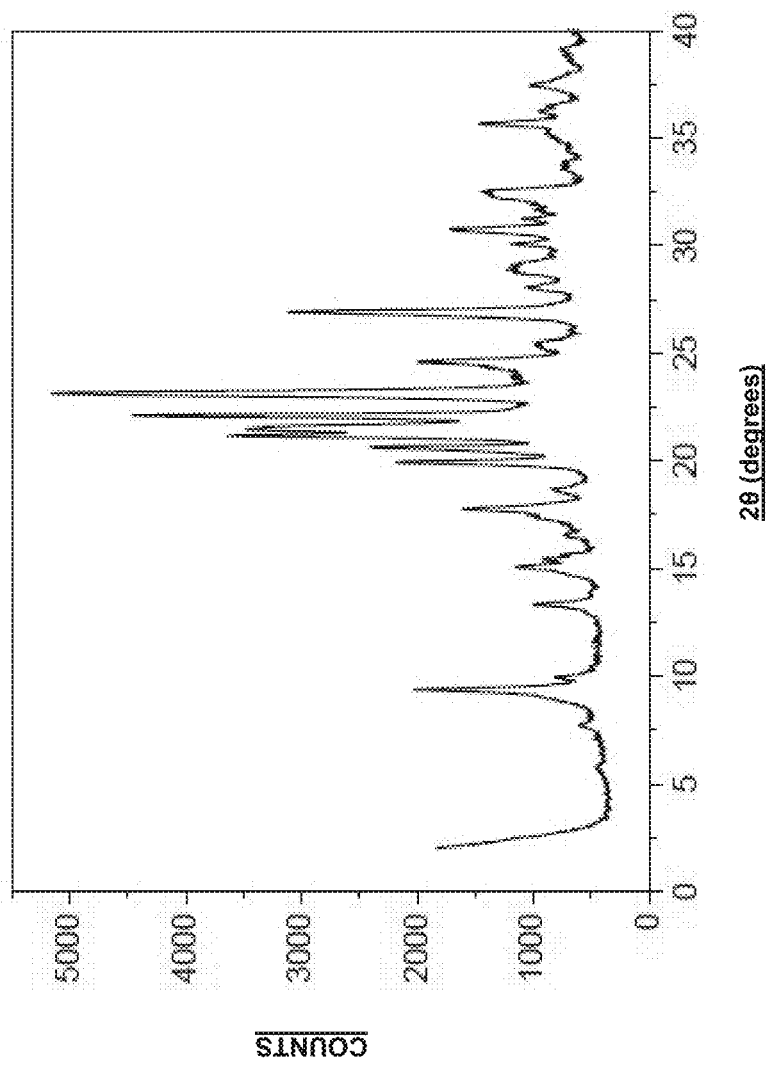
FIG. 3 represents the X-ray diffraction pattern of the most characteristic peaks of the ITQ-55 material that contains Al and Si in its composition, as is synthesized, obtained according to example 4.

The mixture obtained is introduced in an autoclave provided of an internal sleeve of polytetrafluoroethylene and is warmed at 150° C. over 14 days in an electrical furnace provided with a rotation system. The solid obtained on filtering, washing with distilled water and drying at 100° C. presents the diffractogram of X-rays that is shown in FIG. 3 and indicates that it is zeolite ITQ-55.

Example 5. Zeolite Preparation ITQ-55

To 0.087 g of Ti tetraethoxide (IV) (TEOTi) is added 8 g of tetraethylorthosilicate (TEOS). Next 40.8 g of a solution of $N^2,N^2,N^2,N^5,N^5,N^5$,3a,6a-octamethyloctahydropentalene-2,5-diammonium dihydroxide $(R(OH)_2)$ is added that contains 0.47 equivalent of hydroxide in 1000 g. The mixture is left evaporating under stirring until complete elimination of the ethanol coming from the hydrolysis of TEOS and TEOTi plus the quantity of water necessary until reaching the final composition that is indicated. Finally, 0.77 g of a solution of hydrofluoric acid is added (50% of HF by weight). The composition of the gel is:

$SiO_2$: 0.01 $TiO_2$: 0.25 $R(OH)_2$: 0.5 HF: $5H_2O$.

The mixture obtained is introduced in a autoclave provided with an internal sleeve of polytetrafluoroethylene and is warmed at 150° C. over 14 days in an electrical furnace provided with a rotation system. The solid obtained on filtering, washing with distilled water and drying at 100° C. is ITQ-55.

Example 6. Zeolite Preparation ITQ-55

6 g is added from a aqueous solution of colloidal silica at 40% (Ludox ACE-40) 42.5 g of a solution of $N^2,N^2,N^2,N^5,N^5,N^5$,3a,6a-octamethyloctahydropentalene-2,5-diammonium dihydroxide $(R(OH)_2)$ that contains 0.47 equivalent of hydroxide in 1000 g. Next 0.1 g of $H_3BO_3$ is added and the mixture is left evaporating under stirring until complete elimination of the surplus water until reaching the final composition that is indicated. Finally, a solution of 0.74 g of ammonium fluoride is added in 2.5 g of water. The composition of the gel is:

$SiO_2$: 0.02 $B_2O_3$: 0.25 R(OH) 2: 0.5 $NH_4F$: $5H_2O$.

The mixture obtained is introduced into a autoclave provided with an internal sleeve of polytetrafluoroethylene and is warmed at 150° C. over 14 days in an electrical furnace provided with a rotation system. The solid obtained on filtering, washing with distilled water and drying at 100° C. is zeolite ITQ-55.

Example 7. Zeolite Preparation ITQ-55

To 8 g of tetraethylorthosilicate (TEOS) is added 36.6 g of a solution of $N^2,N^2,N^2,N^5,N^5,N^5$,3a,6a-octamethyloctahydropentalene-2,5-diammonium dihydroxide $(R(OH)_2)$ that contains 0.53 equivalent of hydroxide in 1000 g. Next 0.0476 g of $H_3BO_3$ is added. The mixture is left evaporating under stirring until complete elimination of the ethanol coming from the hydrolysis of the TEOS plus the quantity of water necessary until reaching the final composition that is indicated. The composition of the gel is:

$SiO_2$: 0.01 $B_2O_3$: 0.25 $R(OH)_2$: 10 $H_2O$.

The mixture obtained is introduced in an autoclave provided of an internal sleeve of polytetrafluoroethylene and is warmed to 150° C. over 14 days in an electrical furnace provided with a rotation system. The solid obtained on filtering, washing with distilled water and drying at 100° C. is ITQ-55.

Example 8. Zeolite Preparation ITQ-55

To 8 g of tetraethylorthosilicate (TEOS) is added 36.3 g of a solution of $N^2,N^2,N^2,N^5,N^5,N^5$,3a,6a-octamethyloctahydropentalene-2,5-diammonium dihydroxide (R(OH)2) that contains 0.532 equivalent of hydroxide in 1000 g. Next 0.805 g of $GeO_2$ is added. The mixture is left evaporating under stirring until complete elimination of the ethanol coming from the hydrolysis of the TEOS plus the quantity of water necessary until reaching the final composition that is indicated. The composition of the gel is:

$SiO_2$: 0.2 $GeO_2$: 0.25 $R(OH)_2$: 10 $H_2O$.

The mixture obtained is introduced in a autoclave provided with an internal sleeve of polytetrafluoroethylene and is warmed at 150° C. over 14 days in an electrical furnace provided with a rotation system. The solid obtained on filtering, washing with distilled water and drying at 100° C. is ITQ-55.

Example 9. Adsorption of $CO_2$ at 30° C. in the ITQ-55 Material of Example 2

The measurement of the adsorption capacity of $CO_2$ of the ITQ-55 material, prepared according to the example 2, at 30° C. and 9 bar corresponds to 2.96 mmoles/g. Likewise, the value obtained after carrying out 20 adsorption/desorption cycles is of 2.95 mmoles/g, which demonstrates that the material ITQ-55 conserves its adsorption capacity after a high number of cycles.

Example 10. Adsorption of $CO_2$ at 60° C. in the ITQ-55 Material of Example 2

The measurement of the $CO_2$ adsorption capacity of the ITQ-55 material, prepared according to the example 2, at 60° C. and 9 bar corresponds to 2.35 mmoles/g.

Example 11. Methane Adsorption at 60° C. in the ITQ-55 Material of Example 2

The measurement of the methane adsorption capacity of the ITQ-55 material, prepared according to the example 2, at 60° C. and 9 bar corresponds to 0.22 mmoles/g, after equilibrating for 24 hours at this temperature and pressure.

Example 12. Methane Adsorption at 30° C. in the ITQ-55 Material of Example 2

The measurement of the methane adsorption capacity of the ITQ-55 material, prepared according to the example 2, at 30° C. and 9 bar corresponds to 0.18 mmoles/g after equilibrating for 24 hours at this temperature and pressure. The lowest adsorption capacity under these conditions regarding the one observed in the example 5 indicates the drop in diffusion capacity of the methane through the zeolite ITQ-55 pores.

Example 13. Determination of the Selectivity in the Separation of $CO_2$ and Methane in the ITQ-55 Material of Example 2

Figure 4:
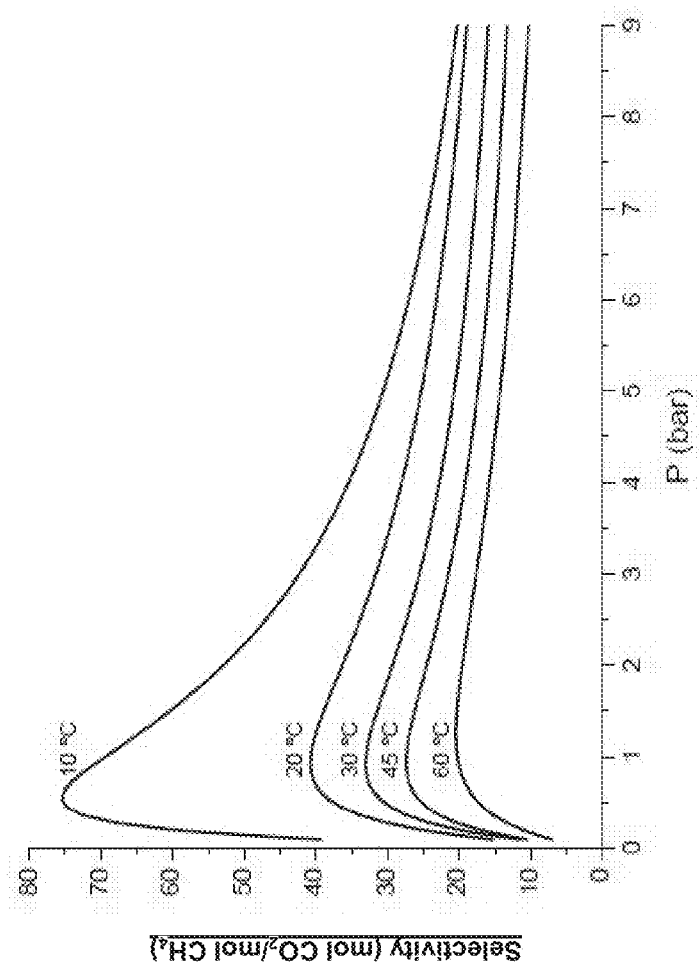
FIG. 4 represents the adsorption selectivity of $CO_2$ over that of methane in the ITQ-55 material in its calcined form, obtained according to example 2. The selectivity is expressed as the ratio of the adsorption capacity obtained starting from the isotherms of the pure gases.

The selectivity in methane and $CO_2$ separation has been considered through the ratio of the adsorption values of the isotherms of the pure gases of $CO_2$ and methane at identical pressure and temperature. It is considered that the selectivity in the separation process will be better insofar as the ratio between these values is greater. In the FIG. 4 the variation of this ratio is shown with the gas pressure at different temperatures.

Example 14. Ethane Adsorption at 30° C. in the ITQ-55 Material of Example 2

The measurement of the adsorption capacity of ethane of the ITQ-55 material, prepared according to the example 2, at 30° C. and 9 bar corresponds to 0.14 mmoles/g after equilibrating for 24 hours at this temperature and pressure.

Example 15. Ethylene Adsorption at 30° C. in the ITQ-55 Material of Example 2

The measurement of the ethylene adsorption capacity of the ITQ-55 material, prepared according to the example 2, at 30° C. and 9 bar corresponds to 0.75 mmoles/g after equilibrating for 24 hours at this temperature and pressure.

Process Example 1. Modeling of Zeolite Structure Fluctuations

In order to further investigate the pore structure of ITQ-55, molecular dynamics simulations of the ITQ-55 structure were performed on a unit cell, with density functional theory being used to determine the interactions between the atoms in the unit cell. A repeating cell boundary condition was used to effectively provide an "infinite" lattice. The molecular dynamics simulations were performed in the NPT ensemble to allow for volume fluctuations of the unit cell. Using density functional theory, an optimized unit cell structure in Angstroms was calculated of 22.58 (a); 13.51 (b); and 14.74 (c). This is comparable to the unit cell structure determined by X-ray diffraction, which was 22.39 (a); 13.34 (b); 14.5 (c). With regard to the size of the smallest pore window, the minimum size window determined by density functional theory for an optimized structure was 2.37 Angstroms. The smallest pore window determined from the X-ray diffraction data was 2.07 Angstroms (minimum). It is noted that either of these minimum dimensions is substantially smaller than the size of several molecules (such as $N_2$ and $CO_2$) that are observed as being adsorbed within the ITQ-55 pore network.

Figure 11:
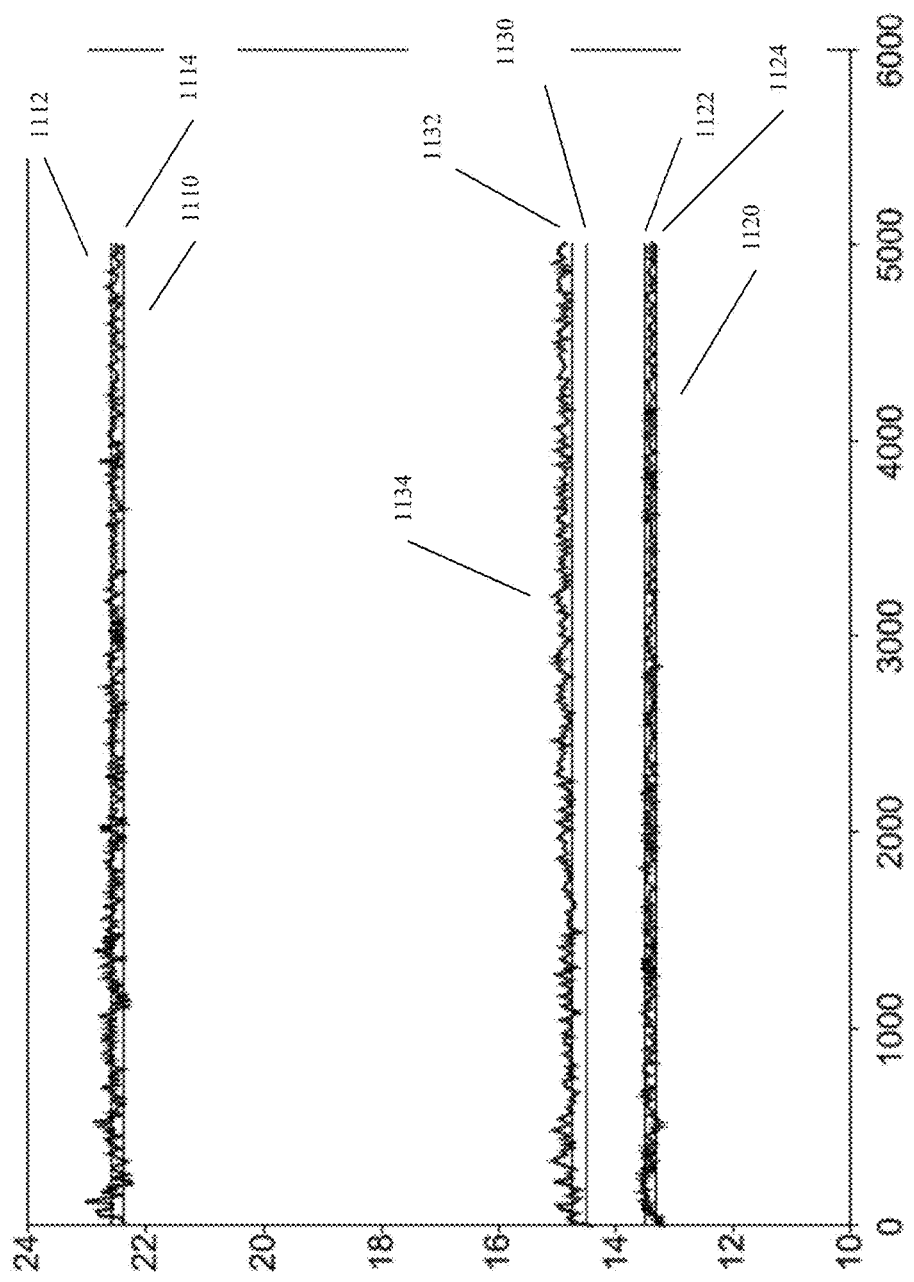
FIG. 11 shows the size of the unit cell for ITQ-55 determined by measured values and determined by simulation.

FIG. 11 shows how the size of the unit cell fluctuated during a molecular dynamics simulation where density functional theory was used for interaction potentials. In FIG. 11, lines 1110, 1120, and 1130 show the a, b, and c parameters (in Angstroms) respectively of the unit cell as determined from X-ray diffraction data. Lines 1112, 1122, and 1132 show the a, b, and c parameters respectively of the unit cell for the optimized structure as determined by density functional theory. Lines 1114, 1124, and 1134 show the a, b, and c parameters respectively of the unit cell as it fluctuates during an NPT ensemble molecular dynamics situation at a temperature of 300 K. As shown in FIG. 11, the "c" parameter of the unit cell showed the largest variation in size between the optimized DFT structure and the size variations calculated at 300 K.

Figure 12:
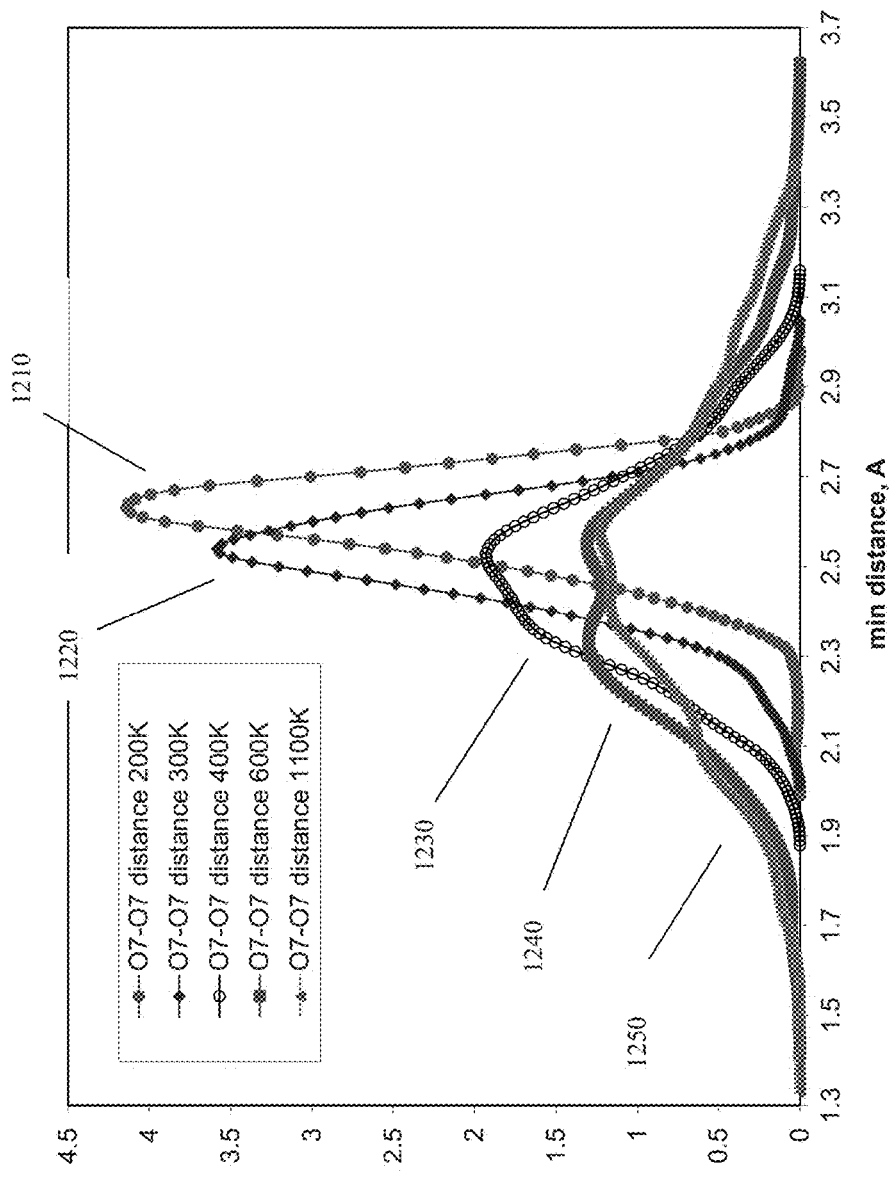
FIG. 12 shows additional results from molecular dynamics simulations related to the minimum aperture (or pore) size in the unit cell for ITQ-55.

FIG. 12 shows additional results from molecular dynamics simulations related to the minimum aperture (or pore) size in the unit cell. FIG. 12 shows changes in the distance between oxygen atoms on opposite sides of the smallest 8-member ring in the unit cell structure during molecular dynamics simulations at various temperatures. The simulation temperatures correspond to 200 K (1210), 300 K (1220), 400 K (1230), 600 K (1240), and 1100 K (1250). It is noted that the total amount of time simulated to generate the results in FIG. 12 corresponds to about 6 picoseconds. In spite of the short amount of time, the size of the minimum pore distance can vary substantially, as shown in FIG. 12. In particular, at the higher temperatures the largest minimum pore distance calculated by the simulations approaches 3.6 Angstroms, which corresponds to the size of the largest molecules (such as $N_2$) that are believed to be able to enter the ITQ-55 pore network. Without being bound by any particular theory, the simulation results at the higher temperatures may tend to show the ability of the ITQ-55 minimum size pore channel to expand, so that some larger molecules can enter, while excluding other molecules beyond a cutoff size. It is also noted that as the temperature decreases, the average size of the minimum distance appears to increase (as shown by the location of the peak maximum), but the amount of fluctuation around the average size decreases (narrower distribution).

Process Example 2. Adsorption Characteristics

Figure 13:
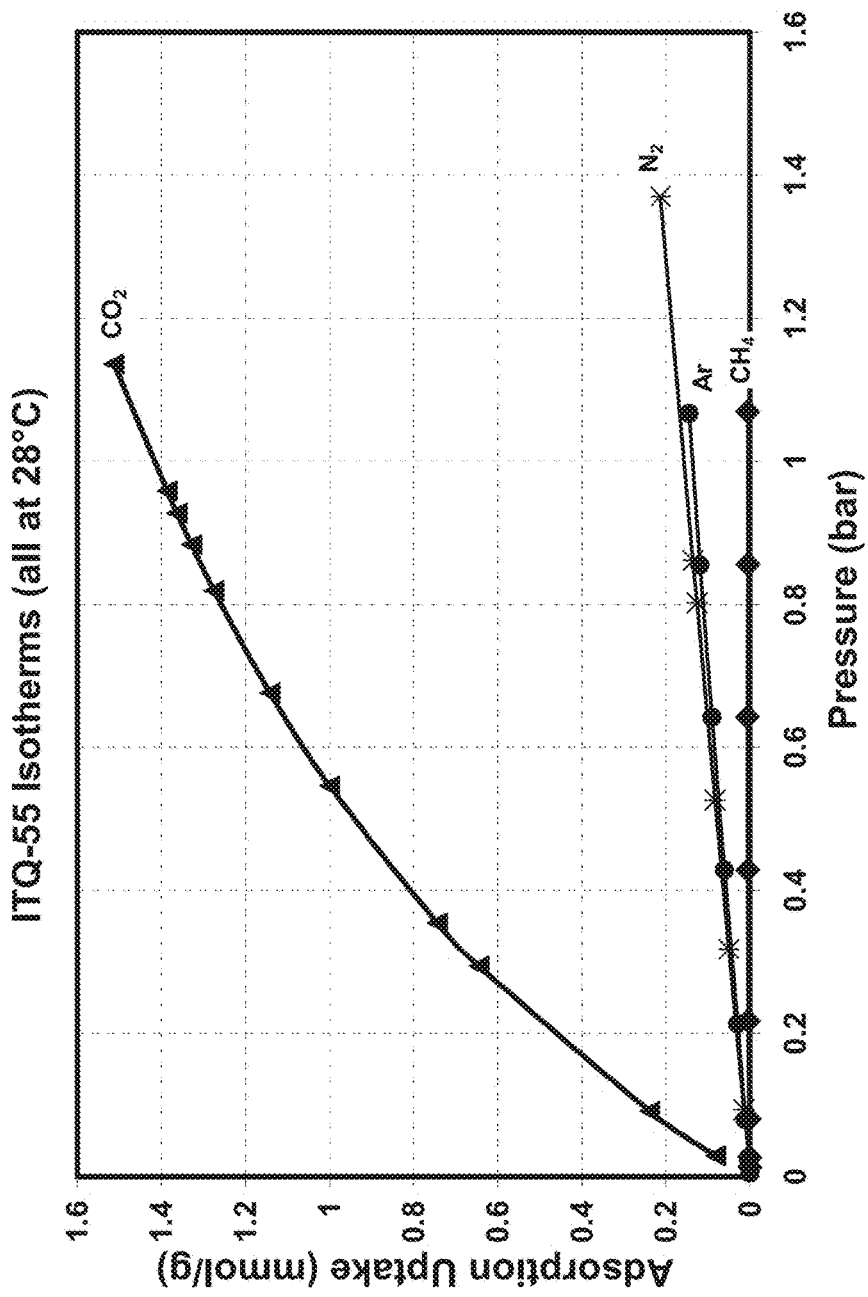
FIG. 13 shows adsorption isotherms at 28° C. for ITQ-55 crystals at low pressures.

FIG. 13 shows adsorption isotherms at 28° C. for ITQ-55 crystals at pressures near ambient. In FIG. 13, the amount of an adsorbed component in mmol per gram of ITQ-55 is shown relative to pressure. As shown in FIG. 13, $CO_2$ is readily adsorbed by ITQ-55. $N_2$ and Ar are also adsorbed, although in smaller amounts. By contrast, substantially no adsorption of methane is observed at 28° C. The isotherms in FIG. 13 appear to show that ITQ-55 can be suitable for separation of $CO_2$, $N_2$, or Ar from larger molecules such as methane. Additionally, the isotherms in FIG. 13 suggest that separations of $CO_2$ from $N_2$ may also be feasible.

Figure 14:
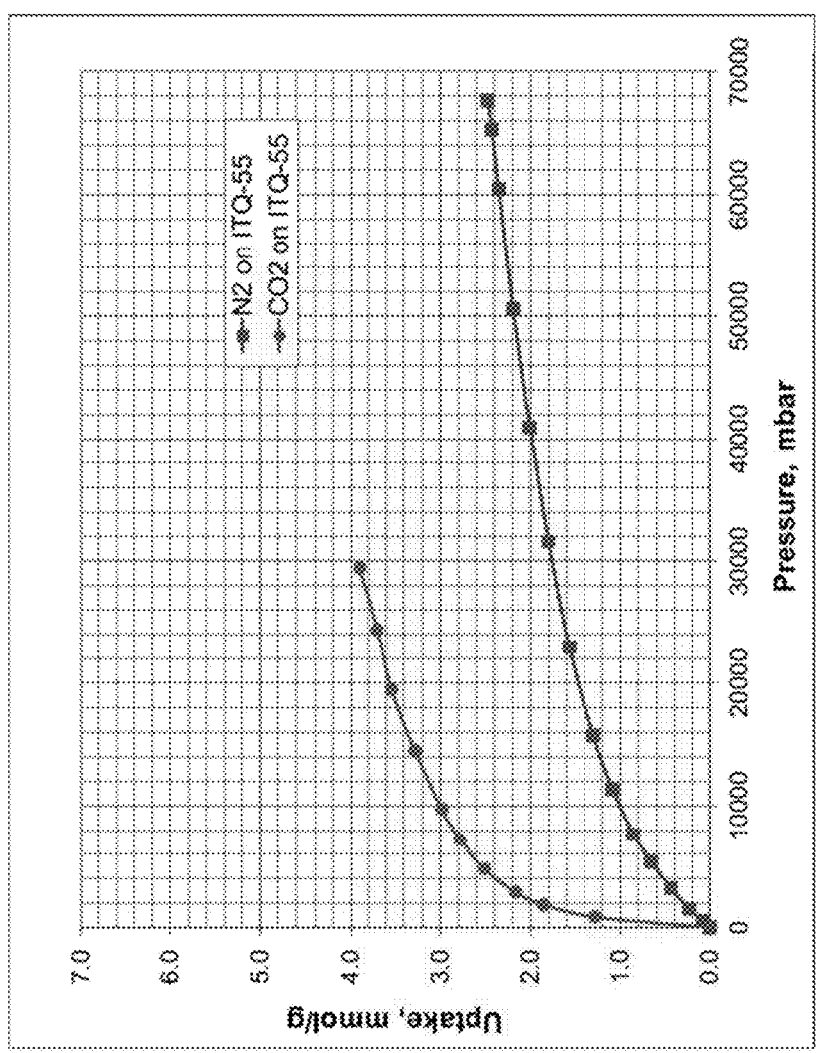
FIG. 14 shows adsorption isotherms for $CO_2$ and $N_2$ for an expanded range of pressures at 30° C.

FIG. 14 shows adsorption isotherms for $CO_2$ and $N_2$ for an expanded range of pressures at 30° C. As shown in FIG. 14, ITQ-55 appears to have a substantial capacity for $CO_2$ and $N_2$ adsorption as pressure increases. The data in FIG. 14 suggests that equilibrium separations involving $CO_2$ and $N_2$ may be limited in selectivity.

Figure 15:
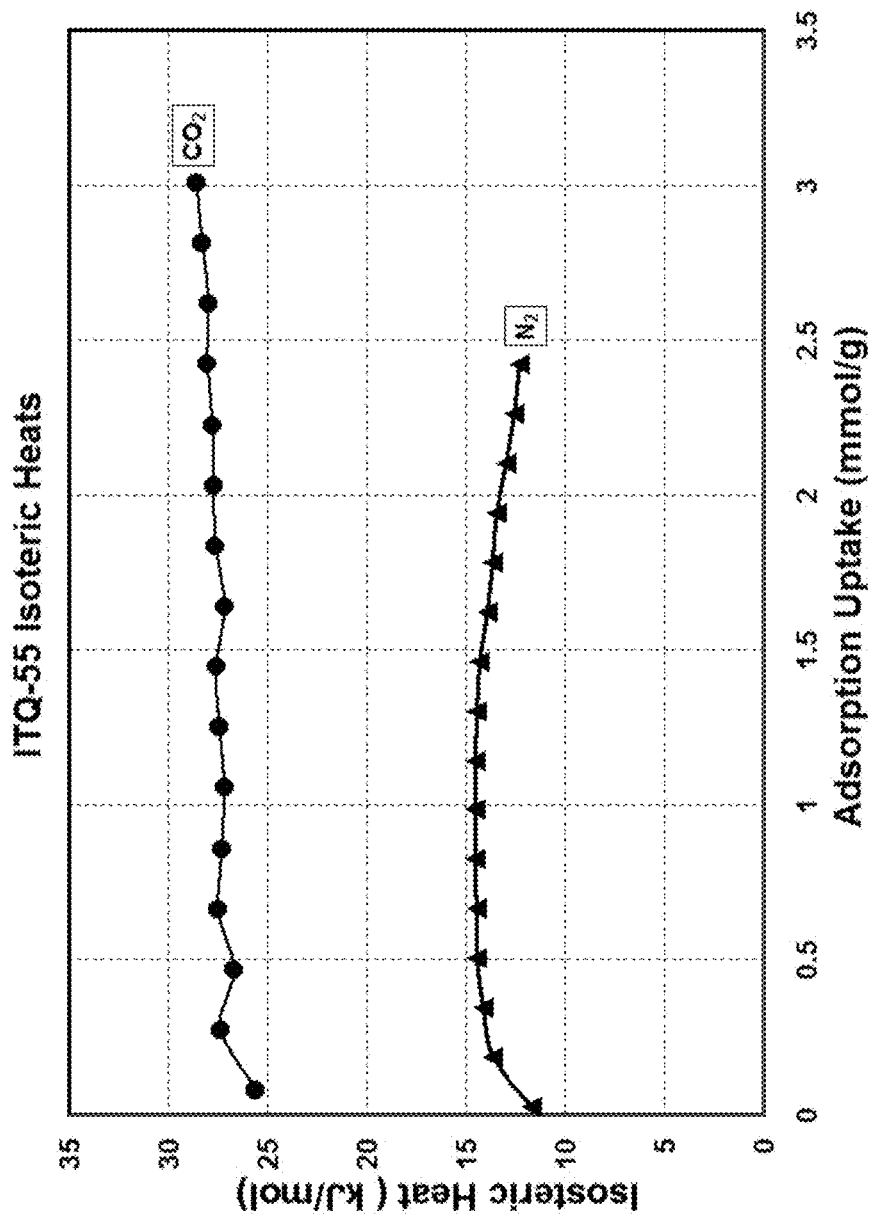
FIG. 15 shows isosteric heats of adsorption for $CO_2$ and $N_2$.

FIG. 15 shows the isosteric heats of adsorption for $CO_2$ and $N_2$. As shown in FIG. 15, the heat of adsorption for $CO_2$ appears to be about twice the value of the heat of adsorption for $N_2$, with the heat of adsorption being mostly independent of the amount of prior uptake.

Figure 16:
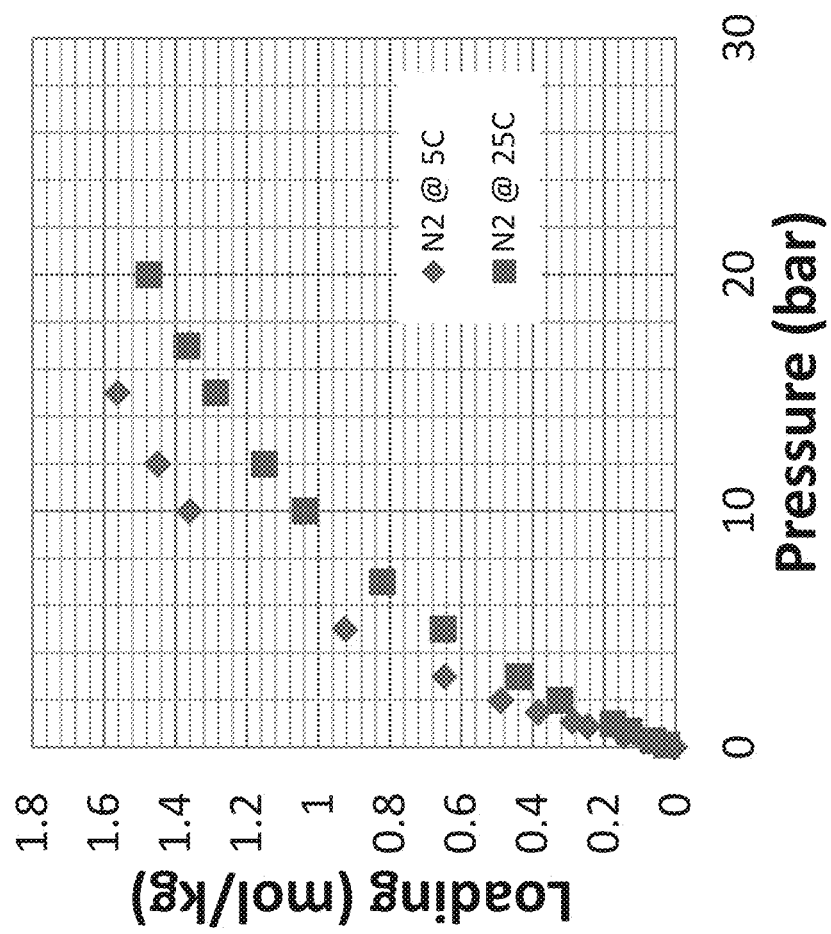
FIG. 16 shows the equilibrium loading of $N_2$ in mol per kg of ITQ-55 at 5° C. and 25° C.

FIG. 16 shows the equilibrium loading of $N_2$ in mol per kg of ITQ-55 at 5° C. and 25° C. As shown in FIG. 16, ITQ-55 appears to have an increased adsorption capacity for $N_2$ as temperature is decreased. Based on the minimal adsorption of methane and larger hydrocarbons by ITQ-55, FIG. 16 suggests that ITQ-55 can be suitable for performing selective separations of $N_2$ from methane (or larger compounds) at temperatures near ambient or below ambient.

FIG. 17 shows the equilibrium loading of $H_2O$ for ITQ-55 in comparison with zeolite 5A, a conventional zeolite used for separations. As shown in FIG. 17, ITQ-55 has a lower capacity for uptake of water in comparison with conventional zeolites. This can be beneficial for reducing or minimizing water adsorption during separation processes involving two other components where water is a trace component in a gas stream.

Figure 18:
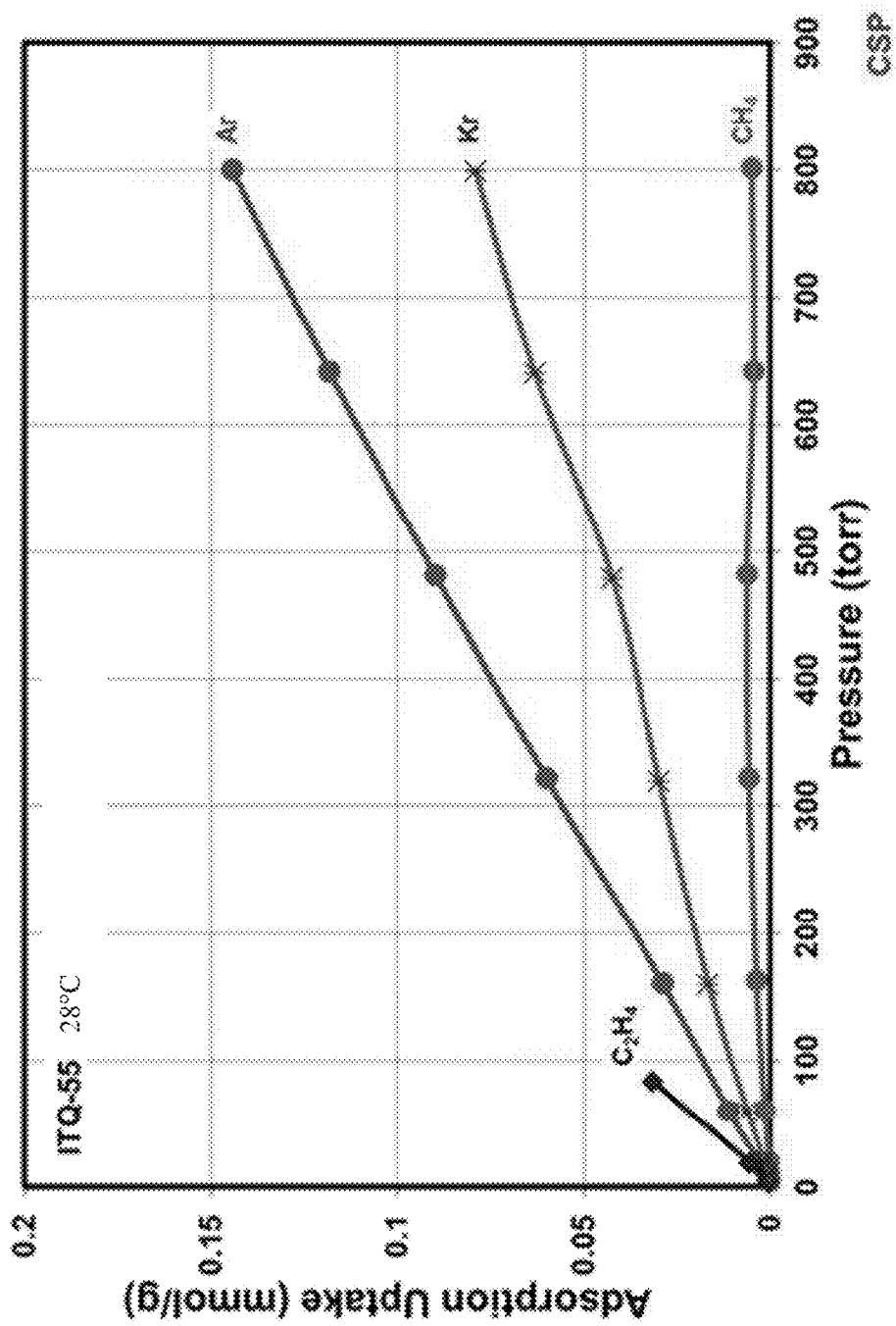
FIG. 18 shows adsorption isotherms at 28° C. for $C_2H_4$, Ar, Kr, and $CH_4$.

FIG. 18 shows adsorption isotherms at 28° C. for $C_2H_4$, Ar, Kr, and $CH_4$. Similar to FIG. 13, minimal or even no adsorption of $CH_4$ is observed. This is in contrast to ethylene, which is adsorbed sufficiently to suggest that ITQ-55 can be suitable for separations of ethylene from methane. Ar and Kr also show sufficient adsorption to be separable from methane and larger hydrocarbons.

Figure 19:
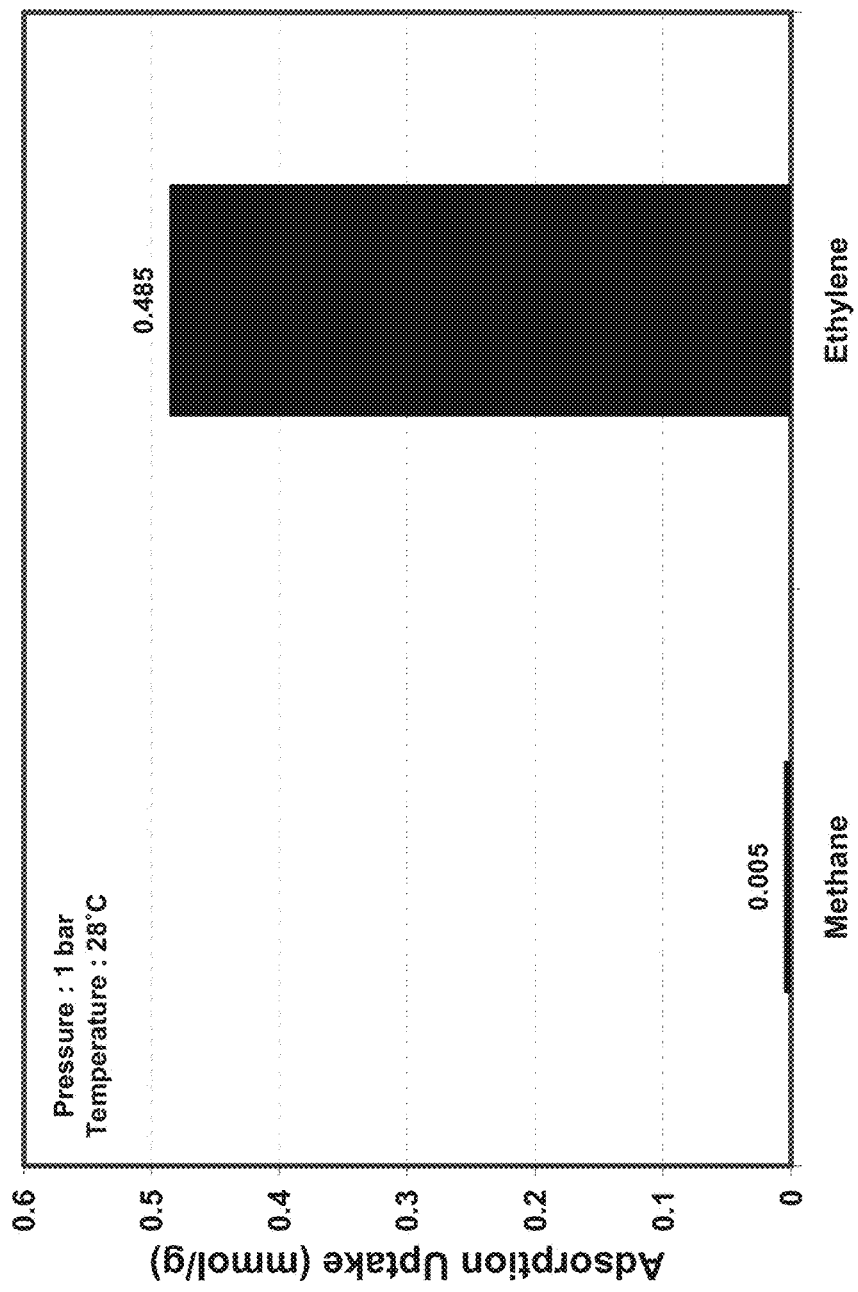
FIG. 19 shows a comparison of equilibrium adsorption of methane and ethylene at 1 bara (101 kPa) and 28° C.

FIG. 19 shows a comparison of equilibrium adsorption of methane and ethylene at 1 bara (101 kPa) and 28° C. As shown in FIG. 19, ITQ-55 has a substantial selectivity for adsorption of ethylene with respect to methane.

Figure 20:
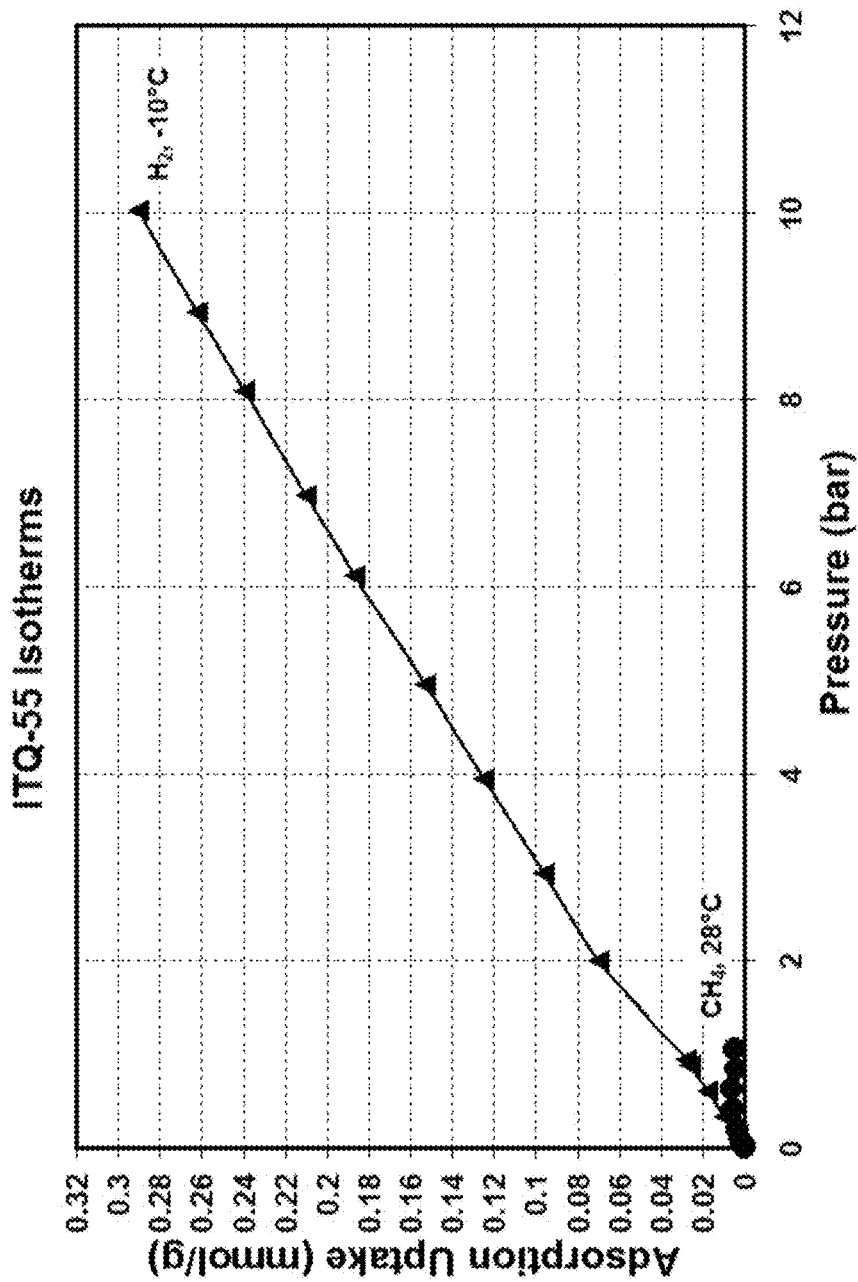
FIG. 20 shows adsorption isotherms for $H_2$ at up to 10 bar (about 1 MPaa) at −10° C. and $CH_4$ at 28° C.

FIG. 20 shows adsorption isotherms for $H_2$ at up to 10 bar (about 1 MPaa) at −10° C. and $CH_4$ at 28° C. Similar to other comparisons, $H_2$ is adsorbed in substantially greater amounts than $CH_4$. The data in FIG. 20 suggests that ITQ-55 can be suitable for kinetic separations of $H_2$ from $CH_4$.

Figure 21:
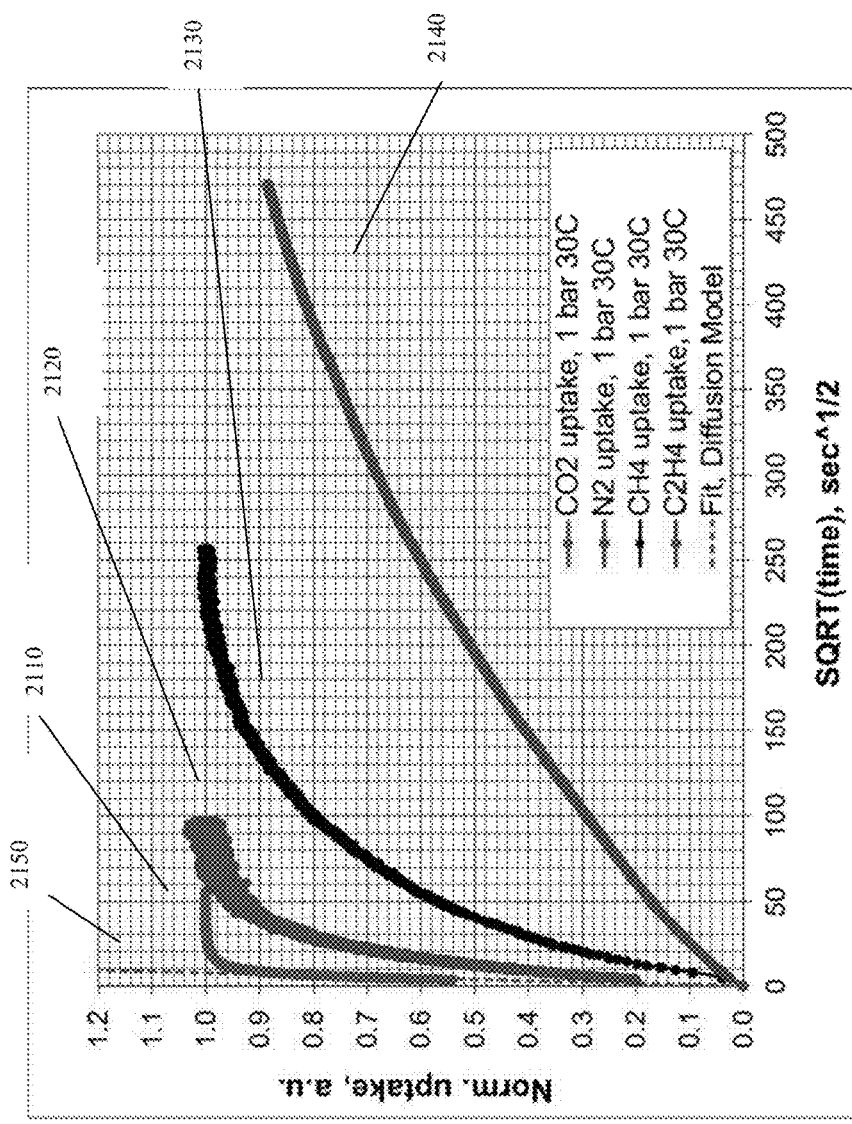
FIG. 21 shows adsorption as a function of the square root of time at 1 bar (101 kPa) and 30° C. for $CO_2$, $N_2$, $CH_4$, and $C_2H_4$.

Although ITQ-55 provides only minimal adsorption of $CH_4$, from a kinetic standpoint any adsorption of $CH_4$ that does occur appears to be faster than adsorption of ethylene. FIG. 21 shows adsorption as a function of the square root of time at 1 bar (101 kPa) and 30° C. for $CO_2$ (2110), $N_2$ (2120), $CH_4$ (2130), and $C_2H_4$ (2140). FIG. 21 also shows a curve fit based on a diffusion model (2150) for $CO_2$ adsorption. The x-axis is selected based on the typical relationship of diffusion to the square root of time. The y-axis is normalized relative to the amount of adsorption to allow for ease of comparison of diffusion rates. As shown in FIG. 21, $N_2$ and $CO_2$ are adsorbed more rapidly than $CH_4$, but ethylene is actually adsorbed more slowly.

Table 101 shows diffusivity values calculated based on the measured adsorption values in FIG. 21. The diffusivity values in Table 101 were calculated for an ITQ-55 crystal size of 60 jpm. Based on the diffusivity values, Table 101 also shows kinetic selectivities. As shown in Table 101, ITQ-55 shows an unexpectedly high kinetic selectivity for $CO_2$ relative to $CH_4$.

TABLE 101

Figure 23B:
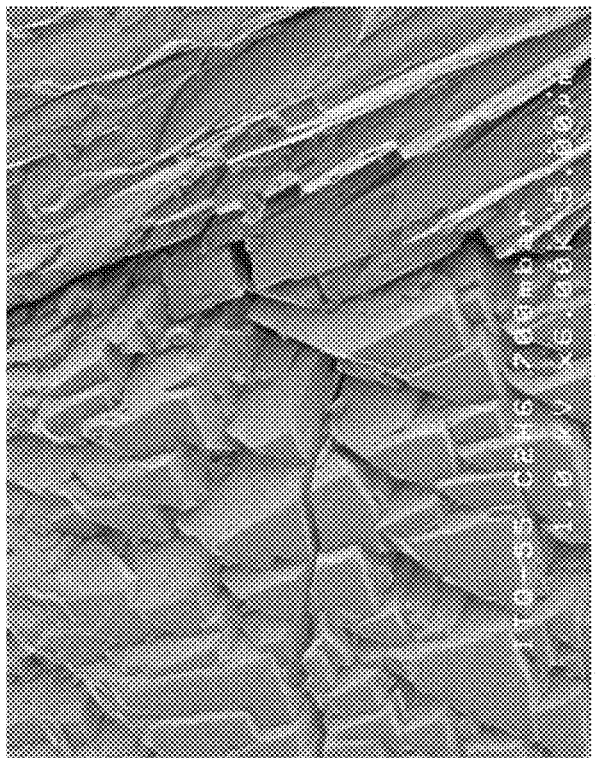
FIGS. 23A and 23B show scanning electron microscopy (SEM) images of ITQ-55 crystals.
Figure 23A:
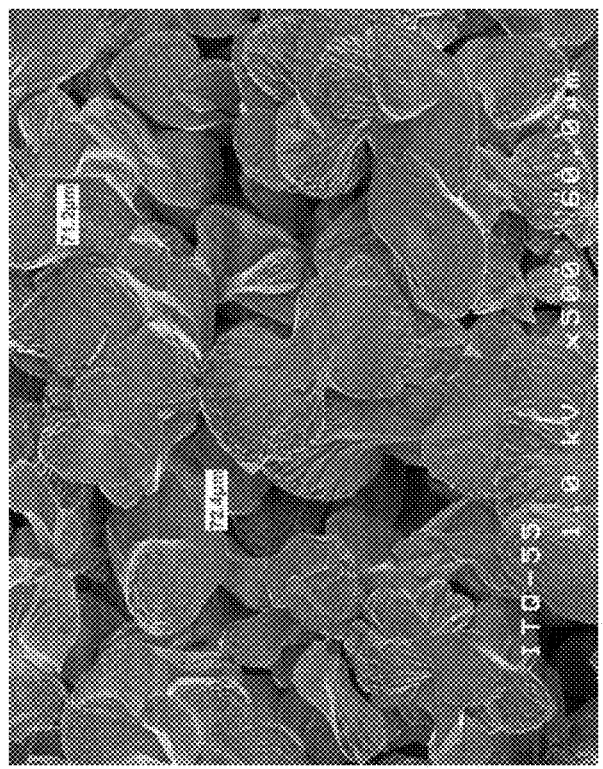

Diffusion time constants $D/R^2$ [1/s] of $N_2$, $CO_2$, $CH_4$, $C_2H_4$ and $C_2H_6$ in 60 μm crystals of ITQ-55 shown in FIG. 23A and 23B measured at 30° C., and ideal kinetic selectivities.

| $N_2$ | $CO_2$ | $CH_4$ | $C_2H_4$ | $C_2H_6$ | $CO_2/CH_4$ kinetic selectivity | $N_2/CH_4$ kinetic selectivity | $C_2H_4/C_2H_6$ kinetic selectivity |
|---|---|---|---|---|---|---|---|
| $2.4 \times 10^{-4}$ | $3.3 \times 10^{-3}$ | $<1.0 \times 10^{-5}$ | $3.0 \times 10^{-7}$ | $<6.6 \times 10^{-9}$ | >300 | >20 | >40 |

Figure 22:
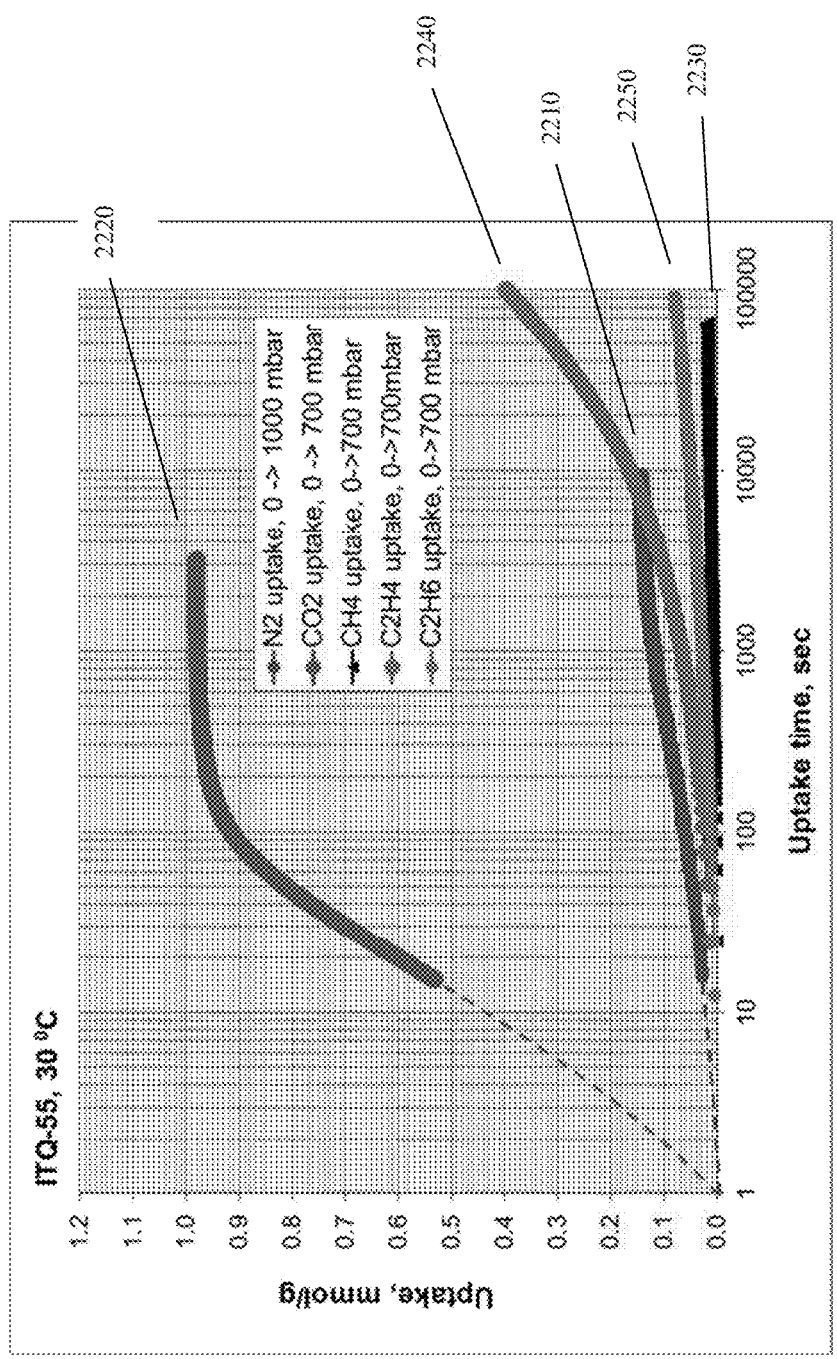
FIG. 22 shows additional data related to uptake as a function of time for $N_2$, $CO_2$, $CH_4$, $C_2H_6$, and $C_2H_4$.

FIG. 22 shows additional data related to uptake as a function of time for $N_2$ (2210), $CO_2$ (2220), $CH_4$ (2230), $C_2H_6$ (2240), and $C_2H_4$ (2250). The data in FIG. 22 corresponds to uptake at 700 mbar (70 kPa), with the exception of $N_2$ which is at 1000 mbar (101 kPa). As shown in FIG. 22, little or no uptake of $CH_4$ and $C_2H_6$ occurs. Both $C_2H_4$ and $N_2$ show slow uptake over time, with a more substantial loading of $C_2H_4$ being achieved at long time periods. Adsorption of $CO_2$ is more rapid than the adsorption of either $C_2H_4$ or $N_2$, suggesting the ability to perform kinetic separations for $CO_2$ relative to these components.

Equilibrium adsorption selectivities were also calculated. Table 102 shows uptake values calculated based on the measured adsorption values in FIG. 22. It is noted that $CH_4$ and $C_2H_6$ both show very low adsorption on ITQ-55. Based on the uptake values, Table 102 also shows adsorption selectivities. As shown in Table 102, ITQ-55 shows an unexpectedly high adsorption selectivity for $CO_2$ relative to $CH_4$.

TABLE 102

Uptake capacity of $N_2$, $CO_2$, $CH_4$, $C_2H_4$ and $C_2H_6$ on ITQ-55 measured at 30° C. and ideal adsorption selectivities.

| $N_2$ uptake, mmol/g (pressure) | $CO_2$ uptake, mmol/g (pressure) | $CH_4$ uptake*, mmol/g (pressure) | $C_2H_4$ uptake, mmol/g (pressure) | $C_2H_6$ uptake*, mmol/g (pressure) | $CO_2/CH_4$ adsorption selectivity | $N_2/CH_4$ adsorption selectivity | $C_2H_4/C_2H_6$ adsorption selectivity |
|---|---|---|---|---|---|---|---|
| 0.16 (970 mbar) | 0.94 (536 mbar) | 0.015 (600 mbar) | 0.40 (570 mbar) | 0.08 (595 mbar) | 62.7 | 10.7 | 5.0 |

Figure 28:
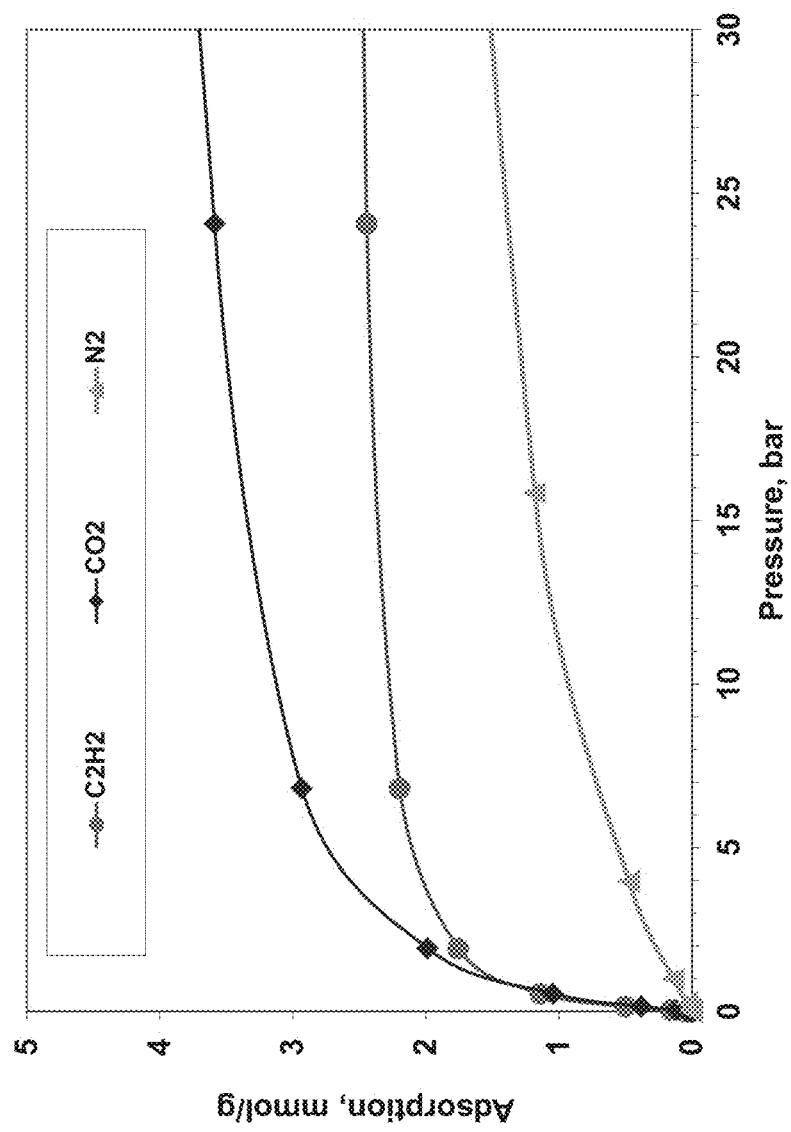
FIG. 28 shows calculated adsorption isotherms for acetylene on ITQ-55.

FIG. 28 shows calculated adsorption isotherms for acetylene on ITQ-55. Acetylene is believed to have a kinetic diameter similar to $CO_2$ and is therefore expected to be able to enter/diffuse into the pore structure of ITQ-55. In order to investigate the adsorption of acetylene, Grand Canonical Monte Carlo simulations were performed for adsorption of acetylene on an ITQ-55 crystal surface. As a comparison, simulations were also performed for adsorption of $CO_2$ and $N_2$ in order to calculate adsorption isotherms. As shown in FIG. 28, acetylene ($C_2H_2$) is predicted to be adsorbed in larger amounts than $N_2$, but in lower amounts relative to $CO_2$, for the low pressure range of about 0 bar to about 30 bar (3 MPaa).

Process Example 3. Additional SEM Characterization

FIGS. 23A and 23B show scanning electron microscopy (SEM) images of ITQ-55 crystals. The images show large layered crystals with a size of about 50 μm to about 70 μm.

Process Example 4. Diffusion Characteristics

Figure 24:
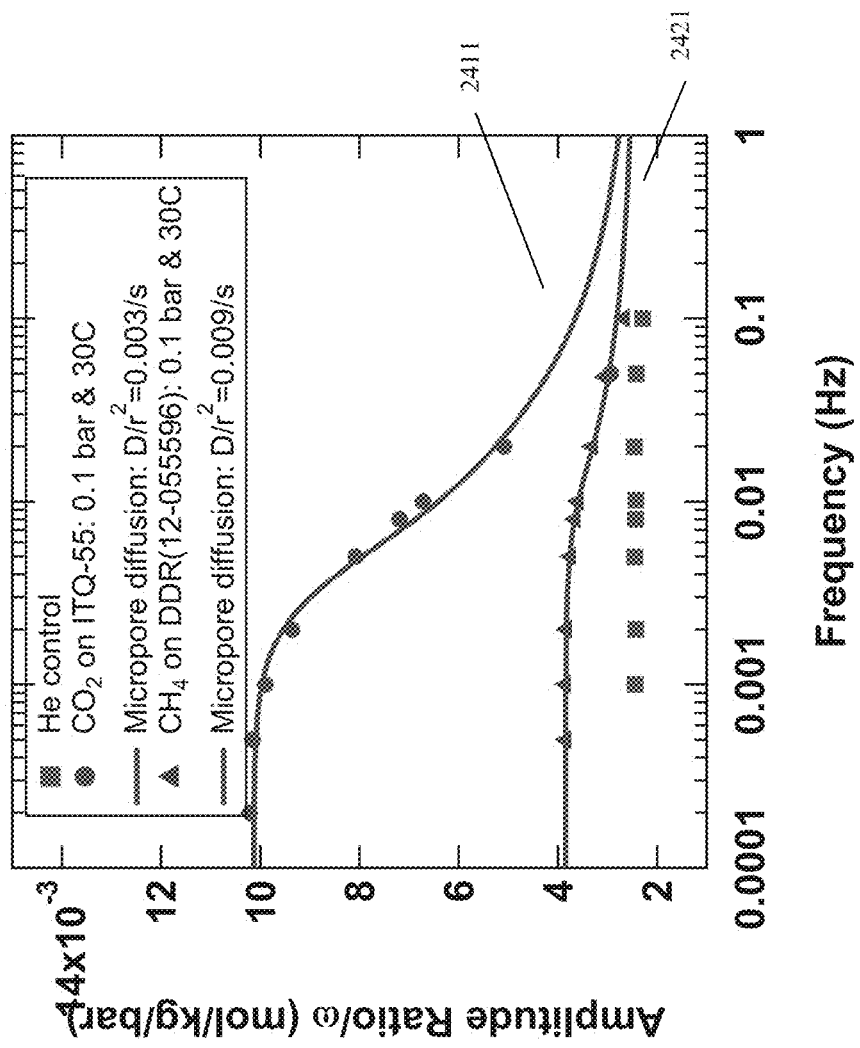
FIGS. 24 and 25 show kinetic studies with frequency response for $CH_4$ and $CO_2$ (FIG. 24) and $N_2$ (FIG. 25) on an ITQ-55 sample.
Figure 25:
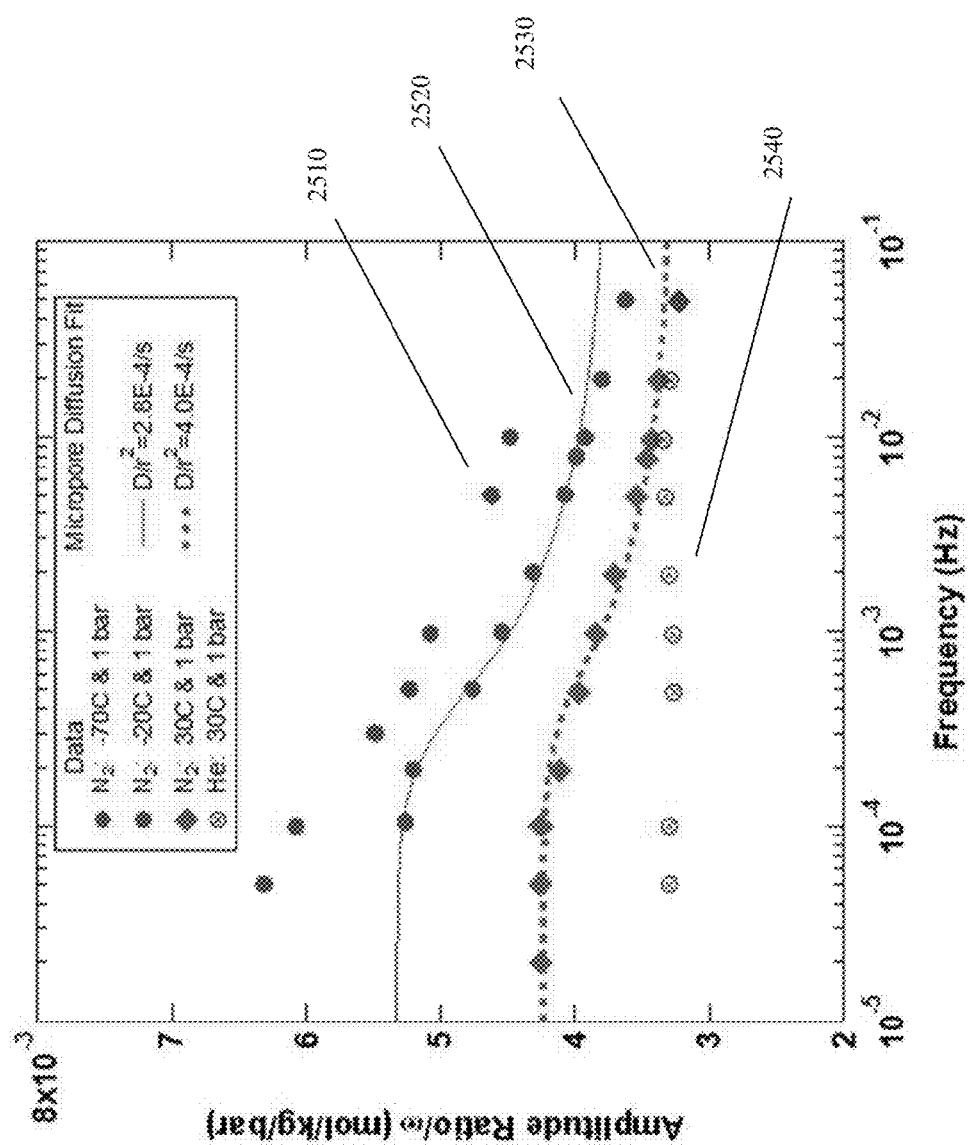

FIGS. 24 and 25 show kinetic studies with frequency response for $CH_4$ and $CO_2$ (FIG. 24) and $N_2$ (FIG. 25) on an ITQ-55 sample. FIG. 24 corresponds to $CH_4$ and $CO_2$ at 30° C. and a pressure of 0.1 bar (10 kPa). In FIG. 24, the line fit to the $CH_4$ data corresponds to line 2411, while the line fit for the $CO_2$ data corresponds to line 2421. The results show that $CH_4$ on ITQ-55 behaves like He with no visual adsorption apparent for the frequency ranges studied. The $CO_2$ diffusion time constant in 60 μm crystals of the ITQ-55 sample shown in FIGS. 23A and 23B is 0.003/s.

FIG. 25 corresponds to $N_2$ adsorption at three temperatures of −70° C. (2510), −20° C. (2520), 30° C. (2530) and same pressure of 1 bar (101 kPa). For comparison, He adsorption at 30° C. and 1 bar is also shown (2540). At low frequencies, the frequency response curves approach plateau to reflect equilibrium status and isotherm slope can be quantified by the difference between plateau of $N_2$ and Helium experiments. The results shows $N_2$ adsorbs more at −70° C. but with slower diffusivities. $N_2$ has ~3 times more capacity at −70° C. compared to 30° C. The $N_2$ diffusion time constant in 60 μm crystals of the ITQ-55 sample shown in FIGS. 23A and 23B is 0.0004/s at 30° C. and slows down to 0.00028/s at −20° C. Comparing diffusivity of $N_2$ and $CO_2$ at similar conditions (30° C.), the kinetic selectivity is about 8. Also, larger kinetic selectivity is for separation of $N_2$ and $CH_4/CO_2$.

Figure 27:
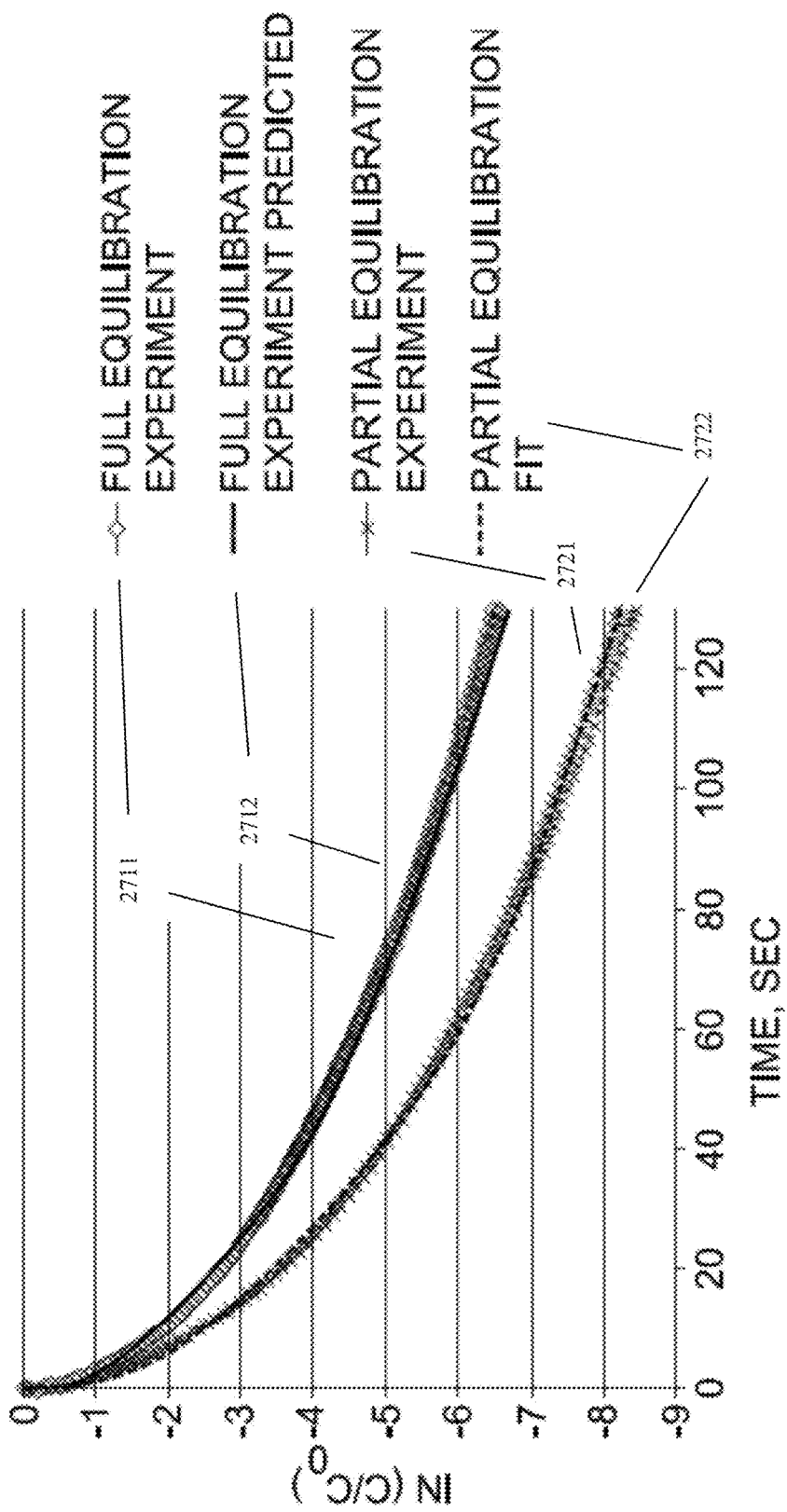
FIG. 27 shows ZLC results for $CO_2$ in ITQ-55.

FIG. 27 shows ZLC results for $CO_2$ in ITQ-55. The ZLC experiments were performed in a small chromatographic column using 10% $CO_2$ in helium. The experimental data with a partial loading experiment 2721 was fitted with a ZLC model 2722, and the full equilibration experiment 2711 was predicted with the model 2712 using the same parameters. The diffusion rate in 60 μm crystals of the ITQ-55 sample shown in FIGS. 23A and 23B has been quantified as 0.003 $sec^{-1}$.

Figure 26:
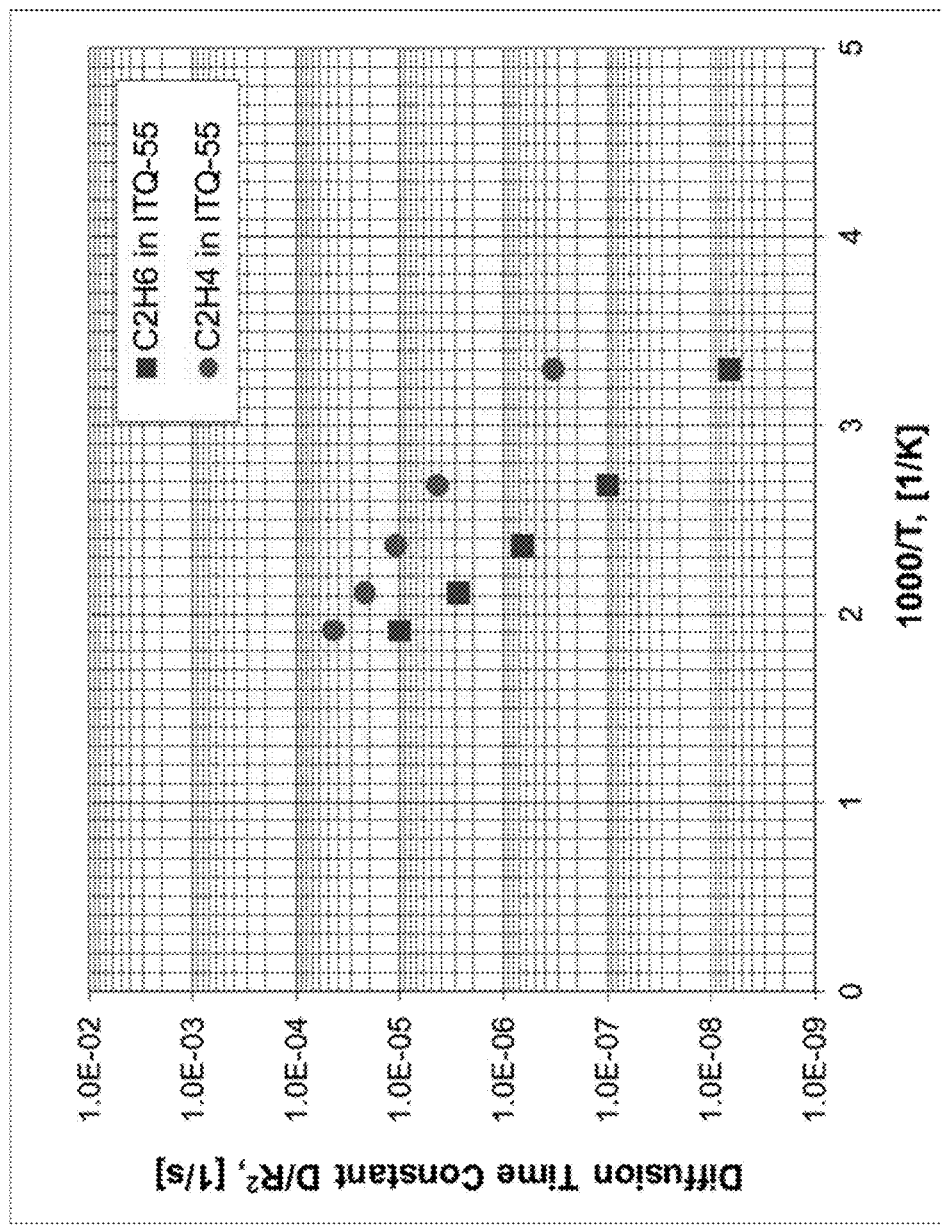
FIG. 26 shows the temperature dependence of diffusion time constants for ethane and ethylene.

In FIG. 26, the temperature dependence of diffusion time constants for ethane and ethylene was estimated from single-gas uptake experiments conducted on a HIDEN IMI volumetric gas sorption apparatus available from Hiden Isochema. Zeolite ITQ-55 was first activated at 300° C. under dynamic vacuum for 4 hours to remove moisture and previously adsorbed species, then cooled down to a selected temperature. Target gas was introduced into the sample cell at 1.1 bar. Gradual pressure drop in the sample cell was accounted for as gas adsorption on the zeolite. The measured gas uptake curve was used to estimate the diffusion time constant. Although equilibrium loading was not reached at the conditions shown in FIG. 26, simulated values were used to determine the equilibrium loading. The procedure was repeated at the next temperature and/or for the next adsorbate gas. As shown in FIG. 26, the temperature dependence of diffusion time constant shows higher activation energy of diffusion for ethane relative to ethylene. At temperatures near 25° C., ethylene appears to have a higher kinetic selectivity of about 50. As temperature increases, FIG. 26 shows that the kinetic selectivity for ethylene relative to ethane decreases.

Prophetic Example 1. Separation of $N_2$ from Methane, Natural Gas, and Other Hydrocarbons The following is a prophetic example. Natural gas deposits can often include nitrogen as part of the total gas composition. Additionally, during extraction of natural gas, nitrogen can be introduced into a well to assist with extraction. This process can sometimes be referred to as "nitrogen flooding". As a result, natural gas can often include nitrogen as a "contaminant". Nitrogen is generally not harmful to many natural gas uses, but nitrogen can act as a diluent, reducing the fuel value of a natural gas feed. Thus, it can be beneficial to reduce or minimize the nitrogen content of a natural gas feed. It is noted that natural gas can typically contain a substantial portion of methane, along with a variety of other small (C2-C4) hydrocarbons. Thus, the techniques described herein for separation of nitrogen from natural gas can also be suitable more generally for separation of nitrogen from methane, ethane, and other organic compounds containing three or more heavy atoms. These techniques can also be suitable for separation of nitrogen from ethylene and/or acetylene, although the selectivities may be different than the selectivities for alkanes or alcohols.

Nitrogen can be separated from natural gas (or other streams containing alkanes/organic compounds) using an adsorbent and/or membrane that includes zeolite ITQ-55. Adsorption can be performed using any convenient type of process, such as a swing adsorption process. For separation by adsorption, a natural gas (or other stream containing alkanes/organic compounds) that also contains nitrogen can be exposed to an adsorbent structure. The surface of the adsorbent structure can be composed of and/or include zeolite ITQ-55 in a manner so that fluids that enter the adsorbent structure can enter by passing through pores of the ITQ-55. Depending on the adsorbent structure, defects in the ITQ-55 crystal structure and/or defects between crystals can allow some fluids to enter the adsorbent structure without passing through the ITQ-55. Due to such defects, less than 100% of the fluids entering the adsorbent structure may pass through the ITQ-55 crystals, such as at least about 90 vol %, or at least about 95%, or at least about 98%.

Similarly, for separation by permeation through a membrane, a natural gas (or other stream containing alkanes/organic compounds) that also contains nitrogen can be exposed to a membrane structure. The surface of the membrane structure can be composed of and/or include zeolite ITQ-55 in a manner so that fluids that enter the membrane structure can enter by passing through pores of the ITQ-55. Depending on the adsorbent structure, defects in the ITQ-55 crystal structure and/or defects between crystals can allow some fluids to enter the membrane structure without passing through the ITQ-55. Due to such defects, less than 100% of the fluids entering the membrane structure may pass through the ITQ-55 crystals, such as at least about 90 vol %, or at least about 95%, or at least about 98%.

During a separation process, a fluid comprising natural gas (or other hydrocarbon or organic components) and nitrogen can be exposed to an adsorbent or membrane structure. Based on the kinetic diameter and/or the affinity of nitrogen for the ITQ-55, the nitrogen can preferentially enter the adsorbent or membrane structure relative to methane or other organic compounds. This can allow for selectivity for nitrogen over methane or another organic compound, either for adsorption or for separation via membrane, of at least about 5, or at least about 10, or at least about 20, or at least about 30.

Optionally, the adsorption separation or membrane can be performed at a temperature below 300 K, such as 275 K or less, or 250 K or less, or 225 K or less, or 200 K or less. This can enhance the selectivity of the ITQ-55 for performing the separation, as well as potentially increasing the capacity of an adsorbent structure for holding nitrogen. Optionally, performing a separation at low temperature can also benefit from allowing water to be condensed out of a fluid prior to the fluid being exposed to the adsorbent or membrane structure. Optionally, a low temperature separation can be performed at any convenient pressure, such as a pressure of 1000 bar (100 MPaa) or less. It is noted that at these separation conditions, the fluid being separated can optionally correspond to a liquid.

As another option, the separation can be performed at a temperature of about 270 K to about 375 K and at a pressure of about 700 bar (70 MPaa) or less, or about 500 bar (50 MPaa) or less, or about 300 bar (30 MPaa) or less, or about 100 bar (10 MPaa) or less. Under these conditions, entry of methane or other organic compounds can be reduced, minimized, or possibly eliminated. The minimized entry of methane or other organic compounds into the adsorbent structure or membrane structure can facilitate performing a separation with high selectivity.

As still another option, the separation can be performed at a temperature greater than about 270 K, or greater than about 325 K, or greater than about 375 K, such as up to about 600 K or more. Additionally or alternately, the separation can be performed at a pressure greater than about 100 bar (10 MPaa), or greater than about 300 bar (30 MPaa), or greater than about 500 bar (50 MPaa), or greater than about 700 bar (70 MPaa), such as up to about 1500 bar (150 MPaa) or more. Additionally or alternately, the separation can be performed at any combination of a temperature and pressure range cited in this paragraph. Under these conditions, some methane or other organic compound may be able to enter an adsorbent structure or membrane structure, but the separation can be performed with a selectivity as described above.

Prophetic Example 2. Separation of $CO_2$ from Methane, Natural Gas, and Other Hydrocarbons The following is a prophetic example. Natural gas deposits can often include $CO_2$ as part of the total gas composition. $CO_2$ is generally not harmful to many natural gas uses, but $CO_2$ can act as a diluent, reducing the fuel value of a natural gas feed. Additionally, for some natural gas sources, $CO_2$ may be present due to injection of $CO_2$ into a hydrocarbon reservoir as part of an enhanced oil recovery process. Thus, it can be beneficial to reduce or minimize the $CO_2$ content of a natural gas feed. It is noted that natural gas can typically contain a substantial portion of methane, along with a variety of other small (C2-C4) hydrocarbons. Thus, the techniques described herein for separation of $CO_2$ from natural gas can also be suitable more generally for separation of nitrogen from methane, ethane, and other organic compounds containing three or more heavy atoms. These techniques can also be suitable for separation of $CO_2$ from ethylene and/or acetylene, although the selectivities may be different than the selectivities for alkanes or alcohols.

$CO_2$ can be separated from natural gas (or other streams containing alkanes/organic compounds) using an adsorbent and/or membrane that includes zeolite ITQ-55. Adsorption can be performed using any convenient type of process, such as a swing adsorption process. For separation by adsorption, a natural gas (or other stream containing alkanes/organic compounds) that also contains $CO_2$ can be exposed to an adsorbent structure. The surface of the adsorbent structure can be composed of and/or include zeolite ITQ-55 in a manner so that fluids that enter the adsorbent structure can enter by passing through pores of the ITQ-55. Depending on the adsorbent structure, defects in the ITQ-55 crystal structure and/or defects between crystals can allow some fluids to enter the adsorbent structure without passing through the ITQ-55. Due to such defects, less than 100% of the fluids entering the adsorbent structure may pass through the ITQ-55 crystals, such as at least about 90 vol %, or at least about 95%, or at least about 98%.

Similarly, for separation by permeation through a membrane, a natural gas (or other stream containing alkanes/organic compounds) that also contains $CO_2$ can be exposed to a membrane structure. The surface of the membrane structure can be composed of and/or include zeolite ITQ-55 in a manner so that fluids that enter the membrane structure can enter by passing through pores of the ITQ-55. Depending on the adsorbent structure, defects in the ITQ-55 crystal structure and/or defects between crystals can allow some fluids to enter the membrane structure without passing through the ITQ-55. Due to such defects, less than 100% of the fluids entering the membrane structure may pass through the ITQ-55 crystals, such as at least about 90 vol %, or at least about 95%, or at least about 98%.

During a separation process, a fluid comprising natural gas (or other hydrocarbon or organic components) and $CO_2$ can be exposed to an adsorbent or membrane structure. Based on the kinetic diameter and/or the affinity of nitrogen for the ITQ-55, the $CO_2$ can preferentially enter the adsorbent or membrane structure relative to methane or other organic compounds. This can allow for selectivity for $CO_2$ over methane or another organic compound, either for adsorption or for separation via membrane, of at least about 5, or at least about 10, or at least about 20, or at least about 30.

Optionally, the adsorption separation or membrane can be performed at a temperature below 300 K, such as 275 K or less, or 250 K or less, or 225 K or less, or 200 K or less. This can enhance the selectivity of the ITQ-55 for performing the separation, as well as potentially increasing the capacity of an adsorbent structure for holding $CO_2$. Optionally, performing a separation at low temperature can also benefit from allowing water to be condensed out of a fluid prior to the fluid being exposed to the adsorbent or membrane structure. Optionally, a low temperature separation can be performed at any convenient pressure, such as a pressure of 1000 bar (100 MPaa) or less. It is noted that at these separation conditions, the fluid being separated can optionally correspond to a liquid.

As another option, the separation can be performed at a temperature of about 270 K to about 375 K and at a pressure of about 700 bar (70 MPaa) or less, or about 500 bar (50 MPaa) or less, or about 300 bar (30 MPaa) or less, or about 100 bar (10 MPaa) or less. Under these conditions, entry of methane or other organic compounds can be reduced, minimized, or possibly eliminated. The minimized entry of methane or other organic compounds into the adsorbent structure or membrane structure can facilitate performing a separation with high selectivity.

As still another option, the separation can be performed at a temperature greater than about 270 K, or greater than about 325 K, or greater than about 375 K, such as up to about 600 K or more. Additionally or alternately, the separation can be performed at a pressure greater than about 100 bar (10 MPaa), or greater than about 300 bar (30 MPaa), or greater than about 500 bar (50 MPaa), or greater than about 700 bar (70 MPaa), such as up to about 1500 bar (150 MPaa) or more. Additionally or alternately, the separation can be performed at any combination of a temperature and pressure range cited in this paragraph. Under these conditions, some methane or other organic compound may be able to enter an adsorbent structure or membrane structure, but the separation can be performed with a selectivity as described above.

Prophetic Example 3. Syngas Separations

The following is a prophetic example. Syngas typically refers to a gas mixture containing a combination of $H_2$, CO, $CO_2$, and $H_2O$. Optionally, syngas can sometimes refer to at least two of $H_2$, CO, $CO_2$, and $H_2O$, or at least three of $H_2$, CO, $CO_2$, and $H_2O$. Optionally, a syngas stream can also contain one or more other components, such as $N_2$, $CH_4$, $O_2$, and/or other small hydrocarbons. For at least some uses of syngas, it can be beneficial to reduce or minimize the content of components other than $H_2$, CO, $CO_2$, and $H_2O$. Additionally or alternately, in some aspects it can be beneficial to separate one or more syngas components from the remaining portion of a syngas stream. For example, it can be desirable to separate hydrogen from syngas for use as a fuel, or to separate $CO_2$ from syngas so that the $CO_2$ can be used and/or sequestered.

Hydrogen can be separated from syngas (and optionally from other components present in a syngas stream such as $N_2$ or $CH_4$) using an adsorbent and/or membrane that includes zeolite ITQ-55. Adsorption can be performed using any convenient type of process, such as a swing adsorption process. For separation by adsorption, a syngas stream can be exposed to an adsorbent structure. The surface of the adsorbent structure can be composed of and/or include zeolite ITQ-55 in a manner so that fluids that enter the adsorbent structure can enter by passing through pores of the ITQ-55. Depending on the adsorbent structure, defects in the ITQ-55 crystal structure and/or defects between crystals can allow some fluids to enter the adsorbent structure without passing through the ITQ-55. Due to such defects, less than 100% of the fluids entering the adsorbent structure may pass through the ITQ-55 crystals, such as at least about 90 vol %, or at least about 95%, or at least about 98%.

Similarly, for separation of hydrogen by permeation through a membrane, a syngas stream can be exposed to a membrane structure. The surface of the membrane structure can be composed of and/or include zeolite ITQ-55 in a manner so that fluids that enter the membrane structure can enter by passing through pores of the ITQ-55. Depending on the adsorbent structure, defects in the ITQ-55 crystal structure and/or defects between crystals can allow some fluids to enter the membrane structure without passing through the ITQ-55. Due to such defects, less than 100% of the fluids entering the membrane structure may pass through the ITQ-55 crystals, such as at least about 90 vol %, or at least about 95%, or at least about 98%.

During a separation process, a fluid comprising syngas can be exposed to an adsorbent or membrane structure. Based on the kinetic diameter and/or the affinity of hydrogen for the ITQ-55, the hydrogen can preferentially enter the adsorbent or membrane structure relative to other components of a syngas. This can allow for selectivity for hydrogen over other syngas components, either for adsorption or for separation via membrane, of at least about 5, or at least about 10, or at least about 20, or at least about 30.

Another option can be to separate $CO_2$ from syngas using an adsorbent and/or membrane that includes zeolite ITQ-55. Relative to other syngas components, $CO_2$ can be a component that is preferentially not adsorbed, so that the product with an increase in $CO_2$ concentration can be the portion of the stream that is not adsorbed. Adsorption can be performed using any convenient type of process, such as a swing adsorption process. For separation by adsorption, a syngas stream can be exposed to an adsorbent structure. The surface of the adsorbent structure can be composed of and/or include zeolite ITQ-55 in a manner so that fluids that enter the adsorbent structure can enter by passing through pores of the ITQ-55. Depending on the adsorbent structure, defects in the ITQ-55 crystal structure and/or defects between crystals can allow some fluids to enter the adsorbent structure without passing through the ITQ-55. Due to such defects, less than 100% of the fluids entering the adsorbent structure may pass through the ITQ-55 crystals, such as at least about 90 vol %, or at least about 95%, or at least about 98%.

Similarly, for separation of $CO_2$ using a membrane, a syngas stream can be exposed to a membrane structure. Because other syngas components can tend to preferentially enter a membrane composed of ITQ-55, the stream enriched in $CO_2$ can correspond to the retentate of the membrane separation. The surface of the membrane structure can be composed of and/or include zeolite ITQ-55 in a manner so that fluids that enter the membrane structure can enter by passing through pores of the ITQ-55. Depending on the adsorbent structure, defects in the ITQ-55 crystal structure and/or defects between crystals can allow some fluids to enter the membrane structure without passing through the ITQ-55. Due to such defects, less than 100% of the fluids entering the membrane structure may pass through the ITQ-55 crystals, such as at least about 90 vol %, or at least about 95%, or at least about 98%.

During a separation process, a fluid comprising syngas can be exposed to an adsorbent or membrane structure. Based on the kinetic diameter and/or the affinity of $CO_2$ for the ITQ-55 relative to other syngas components, the $CO_2$ can preferentially not enter the adsorbent or membrane structure relative to other components of a syngas. This can allow for selectivity for $CO_2$ over other syngas components, either for adsorption or for separation via membrane, of at least about 5, or at least about 10, or at least about 20, or at least about 30. It is noted that a syngas stream that additional contains other non-syngas components, such as $N_2$ or $CH_4$, may benefit from two separation steps. A first step can separate $CO_2$, $N_2$, and $CH_4$ from the remaining syngas components as the non-adsorbed or retentate stream. A second separation can then take advantage of the increased affinity of $CO_2$ for ITQ-55 relative to $N_2$ and/or $CH_4$ to form an enriched adsorbed stream or permeate stream.

Optionally, the adsorption separation or membrane can be performed at a temperature below 300 K, such as 275 K or less, or 250 K or less, or 225 K or less, or 200 K or less. This can enhance the selectivity of the ITQ-55 for performing the separation, as well as potentially increasing the capacity of an adsorbent structure for holding hydrogen and/or $CO_2$. Optionally, performing a separation at low temperature can also benefit from allowing water to be condensed out of a fluid prior to the fluid being exposed to the adsorbent or membrane structure. Optionally, a low temperature separation can be performed at any convenient pressure, such as a pressure of 1000 bar (100 MPaa) or less. It is noted that at these separation conditions, the fluid being separated can optionally correspond to a liquid.

As another option, the separation can be performed at a temperature of about 270 K to about 375 K and at a pressure of about 700 bar (70 MPaa) or less, or about 500 bar (50 MPaa) or less, or about 300 bar (30 MPaa) or less, or about 100 bar (10 MPaa) or less. Under these conditions, entry of methane or other organic compounds can be reduced, minimized, or possibly eliminated. The minimized entry of methane or other organic compounds into the adsorbent structure or membrane structure can facilitate performing a separation with high selectivity.

As still another option, the separation can be performed at a temperature greater than about 270 K, or greater than about 325 K, or greater than about 375 K, such as up to about 600 K or more. Additionally or alternatively, the separation can be performed at a pressure greater than about 100 bar (10 MPaa), or greater than about 300 bar (30 MPaa), or greater than about 500 bar (50 MPaa), or greater than about 700 bar (70 MPaa), such as up to about 1500 bar (150 MPaa) or more. Additionally or alternatively, the separation can be performed at any combination of a temperature and pressure range cited in this paragraph. Under these conditions, some methane or other organic compound may be able to enter an adsorbent structure or membrane structure, but the separation can be performed with a selectivity as described above.

Prophetic Example 4. Separation of O from $N_2$

The following is a prophetic example. A commercially important type of separation is separation of $O_2$ from $N_2$. While air can be used as a feed for some reactions, in many situations it can be desirable to have a stream either enriched or depleted in oxygen relative to air. In addition to separating oxygen from nitrogen with a starting stream of air, such separations can generally be performed on other streams containing both oxygen and nitrogen.

Nitrogen can be separated from oxygen using an adsorbent and/or membrane that includes zeolite ITQ-55. Adsorption can be performed using any convenient type of process, such as a swing adsorption process. For separation by adsorption, a stream that contains nitrogen and oxygen can be exposed to an adsorbent structure. Oxygen can generally have a smaller kinetic diameter and/or higher affinity for ITQ-55, so it is believed that oxygen can preferentially enter the pore structure of zeolite ITQ-55. The surface of the adsorbent structure can be composed of and/or include zeolite ITQ-55 in a manner so that fluids that enter the adsorbent structure can enter by passing through pores of the ITQ-55. Depending on the adsorbent structure, defects in the ITQ-55 crystal structure and/or defects between crystals can allow some fluids to enter the adsorbent structure without passing through the ITQ-55. Due to such defects, less than 100% of the fluids entering the adsorbent structure may pass through the ITQ-55 crystals, such as at least about 90 vol %, or at least about 95%, or at least about 98%.

Similarly, for separation by permeation through a membrane, a stream that contains nitrogen and oxygen can be exposed to a membrane structure. The surface of the membrane structure can be composed of and/or include zeolite ITQ-55 in a manner so that fluids that enter the membrane structure can enter by passing through pores of the ITQ-55. Depending on the membrane structure, defects in the ITQ-55 crystal structure and/or defects between crystals can allow some fluids to enter the membrane structure without passing through the ITQ-55. Due to such defects, less than 100% of the fluids entering the membrane structure may pass through the ITQ-55 crystals, such as at least about 90 vol %, or at least about 95%, or at least about 98%.

During a separation process, a fluid comprising oxygen and nitrogen can be exposed to an adsorbent or membrane structure. Based on the relative kinetic diameters and/or the relative affinities of oxygen and nitrogen for the ITQ-55, it is believed that the oxygen can preferentially enter the adsorbent or membrane structure relative to nitrogen. This can allow for selectivity for either oxygen or nitrogen (depending on the product stream that corresponds to a desired output), either for adsorption or for separation via membrane, of at least about 5, or at least about 10, or at least about 20, or at least about 30.

Optionally, the adsorption separation or membrane can be performed at a temperature below 300 K, such as 275 K or less, or 250 K or less, or 225 K or less, or 200 K or less. This can enhance the selectivity of the ITQ-55 for performing the separation, as well as potentially increasing the capacity of an adsorbent structure for holding nitrogen. Optionally, performing a separation at low temperature can also benefit from allowing water to be condensed out of a fluid prior to the fluid being exposed to the adsorbent or membrane structure. Optionally, a low temperature separation can be performed at any convenient pressure, such as a pressure of 1000 bar (100 MPaa) or less. It is noted that at these separation conditions, the fluid being separated can optionally correspond to a liquid.

As another option, the separation can be performed at a temperature of about 270 K to about 375 K and at a pressure of about 700 bar (70 MPaa) or less, or about 500 bar (50 MPaa) or less, or about 300 bar (30 MPaa) or less, or about 100 bar (10 MPaa) or less. Under these conditions, entry of methane or other organic compounds can be reduced, minimized, or possibly eliminated. The minimized entry of methane or other organic compounds into the adsorbent structure or membrane structure can facilitate performing a separation with high selectivity.

As still another option, the separation can be performed at a temperature greater than about 270 K, or greater than about 325 K, or greater than about 375 K, such as up to about 600 K or more. Additionally or alternatively, the separation can be performed at a pressure greater than about 100 bar (10 MPaa), or greater than about 300 bar (30 MPaa), or greater than about 500 bar (50 MPaa), or greater than about 700 bar (70 MPaa), such as up to about 1500 bar (150 MPaa) or more. Additionally or alternatively, the separation can be performed at any combination of a temperature and pressure range cited in this paragraph. Under these conditions, some methane or other organic compound may be able to enter an adsorbent structure or membrane structure, but the separation can be performed with a selectivity as described above.

Prophetic Example 5. Storage of Hydrocarbons and/or Small Organic Compounds

The following is a prophetic example. Although a storage process for hydrocarbons can be initiated using a stream containing multiple components, for clarity in description this prophetic example is based on performing storage based on a single component stream.

In some aspects, storage of a hydrocarbon in an adsorbent structure comprising ITQ-55 can be performed by initially adsorbing the ITQ-55 at an elevated temperature and/or pressure. Suitable compounds for storage can include, but are not limited to, methane, ethane, ethylene, formaldehyde, methanol, dimethyl ether, and combinations thereof.

During an initial adsorption step, a fluid component can be adsorbed into the adsorbent structure. The conditions during adsorption can include, for example, a) a temperature of at least about 325 K, or at least about 375 K, or at least about 425 K, or at least about 475 K; b) a pressure of at least about 100 bar (10 MPaa), or at least about 300 bar (30 MPaa), or at least about 500 bar (50 MPaa), or at least about 700 bar (70 MPaa); or c) a combination thereof. Without being bound by any particular theory, the elevated temperature and/or pressure can allow for introduction of an elevated loading of an organic component into the adsorbent structure.

After loading of the adsorbent structure, the temperature and/or pressure can be reduced. In aspects where loading of the adsorbent structure is performed at an elevated pressure, the pressure can be reduced to about 100 bar (10 MPaa) or less, or about 10 bar (1 MPaa) or less, or about 2 bar (0.2 MPaa) or less, or about 1 bar (0.1 MPaa) or less. In aspects where loading of the adsorbent structure is performed at an elevated temperature, the temperature can be reduced to about 325 K or less, or about 300 K or less, or about 275 K or less, or about 250 K or less, or about 225 K or less, or about 200 K or less. In aspects where both the temperature and pressure are elevated during loading, the temperature can optionally be reduced first, and then the pressure can be reduced. After reducing the temperature and/or pressure, some desorption of the adsorbed component can occur. However, based on the reduced temperature and/or pressure conditions, a portion of the component can remain kinetically trapped within the adsorbent structure. This can allow the adsorbent structure to retain an amount of the fluid component within the adsorbent structure, even though the atmosphere outside of the adsorbent may no longer contain the adsorbed component. The loading retained within the adsorbent can correspond to a percentage of the loading that was achieved during adsorption, such as at least about 10 wt % of the loading during adsorption, or at least about 20 wt %, or at least about 30 wt %, or at least about 40 wt %, or at least about 50 wt %, or at least about 60 wt %. The adsorbent structure can then optionally be transported under the reduced temperature and/or pressure conditions.

After storage for a desired amount of time, the temperature can be increased to allow the adsorbed component to exit from the adsorbent structure. This can allow the adsorbed component, corresponding to a fuel and/or potential reactant, to be stored and optionally transported under less severe conditions. In other words, the temperature and/or pressure required for storage of the adsorbed component in the adsorbent structure can be reduced relative to the conditions required for storing the adsorbed component in the absence of the adsorbent structure.

ADDITIONAL SEPARATION EMBODIMENTS

Embodiment 1

A method for separating fluids, comprising: exposing an input fluid stream comprising a first fluid component and a second fluid component to an adsorbent comprising zeolite ITQ-55 to form a rejection product fluid stream, a molar ratio of the first fluid component to the second fluid component in the rejection product fluid stream being less than a molar ratio of the first fluid component to the second fluid component in the input fluid stream; collecting the rejection product fluid stream; forming an adsorbed product fluid stream, a molar ratio of the first fluid component to the second fluid component in the adsorbed product stream being greater than the molar ratio of the first fluid component to the second fluid component in the input fluid stream; and collecting the adsorbed product stream, wherein the zeolite ITQ-55 has a framework of tetrahedral (T) atoms connected by bridging atoms, wherein the tetrahedral atom is defined by connecting the nearest T atoms in the manner described in the following Table:

| ITQ-55 tetrahedral atom interconnections | |
|---|---|
| T atom | Connected to: |
| T1 | T6, T7, T55, T73 |
| T2 | T3, T5, T9, T56 |
| T3 | T2, T7, T21, T27 |
| T4 | T8, T9, T58, T73 |
| T5 | T2, T8, T52, T59 |
| T6 | T1, T8, T53, T60 |
| T7 | T1, T3, T50, T61 |
| T8 | T4, T5, T6, T51 |
| T9 | T2, T4, T21, T63 |
| T10 | T15, T16, T64, T74 |
| T11 | T12, T14, T18, T65 |
| T12 | T11, T16, T30, T36 |
| T13 | T17, T18, T67, T74 |
| T14 | T11, T17, T43, T68 |
| T15 | T10, T17, T44, T69 |
| T16 | T10, T12, T41, T70 |
| T17 | T13, T14, T15, T42 |
| T18 | T11, T13, T30, T72 |
| T19 | T24, T25, T37, T73 |
| T20 | T21, T23, T27, T38 |
| T21 | T3, T9, T20, T25 |
| T22 | T26, T27, T40, T73 |
| T23 | T20, T26, T41, T70 |
| T24 | T19, T26, T42, T71 |
| T25 | T19, T21, T43, T68 |
| T26 | T22, T23, T24, T69 |
| T27 | T3, T20, T22, T45 |
| T28 | T33, T34, T46, T74 |
| T29 | T30, T32, T36, T47 |
| T30 | T12, T18, T29, T34 |
| T31 | T35, T36, T49, T74 |
| T32 | T29, T35, T50, T61 |
| T33 | T28, T35, T51, T62 |
| T34 | T28, T30, T52, T59 |
| T35 | T31, T32, T33, T60 |
| T36 | T12, T29, T31, T54 |
| T37 | T19, T42, T43, T75 |
| T38 | T20, T39, T41, T45 |
| T39 | T38, T43, T57, T63 |
| T40 | T22, T44, T45, T75 |
| T41 | T16, T23, T38, T44 |
| T42 | T17, T24, T37, T44 |
| T43 | T14, T25, T37, T39 |
| T44 | T15, T40, T41, T42 |
| T45 | T27, T38, T40, T57 |
| T46 | T28, T51, T52, T76 |
| T47 | T29, T48, T50, T54 |
| T48 | T47, T52, T66, T72 |
| T49 | T31, T53, T54, T76 |
| T50 | T7, T32, T47, T53 |
| T51 | T8, T33, T46, T53 |
| T52 | T5, T34, T46, T48 |
| T53 | T6, T49, T50, T51 |
| T54 | T36, T47, T49, T66 |
| T55 | T1, T60, T61, T75 |
| T56 | T2, T57, T59, T63 |
| T57 | T39, T45, T56, T61 |
| T58 | T4, T62, T63, T75 |
| T59 | T5, T34, T56, T62 |
| T60 | T6, T35, T55, T62 |
| T61 | T7, T32, T55, T57 |
| T62 | T33, T58, T59, T60 |
| T63 | T9, T39, T56, T58 |
| T64 | T10, T69, T70, T76 |
| T65 | T11, T66, T68, T72 |
| T66 | T48, T54, T65, T70 |
| T67 | T13, T71, T72, T76 |

-continued

ITQ-55 tetrahedral atom interconnections

| T atom | Connected to: |
|---|---|
| T68 | T14, T25, T65, T71 |
| T69 | T15, T26, T64, T71 |
| T70 | T16, T23, T64, T66 |
| T71 | T24, T67, T68, T69 |
| T72 | T18, T48, T65, T67 |
| T73 | T1, T4, T19, T22 |
| T74 | T10, T13, T28, T31 |
| T75 | T37, T40, T55, T58 |
| T76 | T46, T49, T64, T67. |

Embodiment 2

A method for separating fluids, comprising: exposing an input fluid stream comprising a first fluid component and a second fluid component to an adsorbent comprising zeolite ITQ-55 to form a rejection product fluid stream, a molar ratio of the first fluid component to the second fluid component in the rejection product fluid stream being less than a molar ratio of the first fluid component to the second fluid component in the input fluid stream; collecting the rejection product fluid stream; forming an adsorbed product fluid stream, a molar ratio of the first fluid component to the second fluid component in the adsorbed product stream being greater than the molar ratio of the first fluid component to the second fluid component in the input fluid stream; and collecting the adsorbed product stream, wherein the zeolite ITQ-55, as synthesized, has an X-ray diffraction pattern with, at least, the angle values 2θ (degrees) and relative intensities ($I/I_0$):

| 2θ (degrees) ± 0.5 | Intensity ($I/I_0$) |
|---|---|
| 5.8 | w |
| 7.7 | w |
| 8.9 | w |
| 9.3 | mf |
| 9.9 | w |
| 10.1 | w |
| 13.2 | m |
| 13.4 | w |
| 14.7 | w |
| 15.1 | m |
| 15.4 | w |
| 15.5 | w |
| 17.4 | m |
| 17.7 | m |
| 19.9 | m |
| 20.6 | m |
| 21.2 | f |
| 21.6 | f |
| 22.0 | f |
| 23.1 | mf |
| 24.4 | m |
| 27.0 | m | where $I_0$ is the intensity from the most intense pick to which is assigned a value of 100
w is a weak relative intensity between 0 and 20%,
m is an average relative intensity between 20 and 40%,
f is a strong relative intensity between 40 and 60%,
and mf is a very strong relative intensity between 60 and 100%.

Embodiment 3

The method of any of the above embodiments, wherein the zeolite ITQ-55 has, in calcined state and in absence of defects in its crystalline matrix manifested by the presence of silanols, an empiric formula

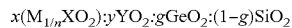

in which
M is selected between $H^+$, at least one inorganic cation of charge +n, and a mixture of both,
X is at least one chemical element of oxidation state +3,
Y is at least one chemical element with oxidation state +4 different from Si,
x takes a value between 0 and 0.2, both included,
y takes a value between 0 and 0.1, both included,
g takes a value between 0 and 0.5, both included.

Embodiment 4

The method of Embodiment 3, wherein x takes a value of essentially zero, y takes a value of essentially zero, and g takes a value of essentially zero.

Embodiment 5

The method of Embodiment 3, wherein a) x takes a value of greater than zero, b) y takes a value of greater than zero, c) g takes a value of greater than zero, or d) a combination thereof.

Embodiment 6

The method of any of the above embodiments, wherein forming an adsorbed product fluid stream comprises modifying at least one of the temperature or the pressure of the adsorbent.

Embodiment 7

The method of any of the above embodiments, wherein forming an adsorbed product fluid stream comprises exposing a fluid stream comprising a third component to the adsorbent comprising zeolite ITQ-55, at least a portion of the third component being adsorbed by the adsorbent comprising zeolite ITQ-55.

Embodiment 8

The method of any of the above embodiments, wherein exposing the input fluid stream to an adsorbent comprises exposing the input fluid stream to an adsorbent in a swing adsorption vessel.

Embodiment 9

The method of Embodiment 8, wherein exposing the input fluid stream to an adsorbent comprises exposing the input fluid stream to the adsorbent under pressure swing adsorption conditions, temperature swing adsorption conditions, rapid cycle pressure swing adsorption conditions, or a combination thereof.

Embodiment 10

The method of any of the above embodiments, wherein the input fluid stream is exposed to the adsorbent at effective conditions for performing a kinetic separation of the first component from the second component, at effective conditions for performing an equilibrium separation of the first component from the second component, or a combination thereof.

Embodiment 11

The method of any of the above embodiments, wherein the adsorbent has less than about 20% of open pore volume in pores having diameters greater than about 20 Angstroms and less than about 1 micron.

Embodiment 12

A method for separating fluids, comprising: exposing an input fluid stream comprising a first fluid component and a second fluid component to a membrane comprising particles of crystalline zeolite ITQ-55 to form a permeate product fluid stream and a rejection product fluid stream, a molar ratio of the first fluid component to the second fluid component in the permeate product fluid stream being greater than a ratio of the first fluid component to the second fluid component in the input fluid stream, a molar ratio of the first fluid component to the second fluid component in the rejection product fluid stream being less than a ratio of the first fluid component to the second fluid component in the input fluid stream, wherein the tetrahedral atom is defined by connecting the nearest T atoms in the manner described in the following Table:

| ITQ-55 tetrahedral atom interconnections | |
|---|---|
| T atom | Connected to: |
| T1 | T6, T7, T55, T73 |
| T2 | T3, T5, T9, T56 |
| T3 | T2, T7, T21, T27 |
| T4 | T8, T9, T58, T73 |
| T5 | T2, T8, T52, T59 |
| T6 | T1, T8, T53, T60 |
| T7 | T1, T3, T50, T61 |
| T8 | T4, T5, T6, T51 |
| T9 | T2, T4, T21, T63 |
| T10 | T15, T16, T64, T74 |
| T11 | T12, T14, T18, T65 |
| T12 | T11, T16, T30, T36 |
| T13 | T17, T18, T67, T74 |
| T14 | T11, T17, T43, T68 |
| T15 | T10, T17, T44, T69 |
| T16 | T10, T12, T41, T70 |
| T17 | T13, T14, T15, T42 |
| T18 | T11, T13, T30, T72 |
| T19 | T24, T25, T37, T73 |
| T20 | T21, T23, T27, T38 |
| T21 | T3, T9, T20, T25 |
| T22 | T26, T27, T40, T73 |
| T23 | T20, T26, T41, T70 |
| T24 | T19, T26, T42, T71 |
| T25 | T19, T21, T43, T68 |
| T26 | T22, T23, T24, T69 |
| T27 | T3, T20, T22, T45 |
| T28 | T33, T34, T46, T74 |
| T29 | T30, T32, T36, T47 |
| T30 | T12, T18, T29, T34 |
| T31 | T35, T36, T49, T74 |
| T32 | T29, T35, T50, T61 |
| T33 | T28, T35, T51, T62 |
| T34 | T28, T30, T52, T59 |
| T35 | T31, T32, T33, T60 |
| T36 | T12, T29, T31, T54 |
| T37 | T19, T42, T43, T75 |
| T38 | T20, T39, T41, T45 |
| T39 | T38, T43, T57, T63 |
| T40 | T22, T44, T45, T75 |
| T41 | T16, T23, T38, T44 |
| T42 | T17, T24, T37, T44 |
| T43 | T14, T25, T37, T39 |
| T44 | T15, T40, T41, T42 |
| T45 | T27, T38, T40, T57 |
| T46 | T28, T51, T52, T76 |
| T47 | T29, T48, T50, T54 |
| T48 | T47, T52, T66, T72 |
| T49 | T31, T53, T54, T76 |
| T50 | T7, T32, T47, T53 |
| T51 | T8, T33, T46, T53 |
| T52 | T5, T34, T46, T48 |
| T53 | T6, T49, T50, T51 |
| T54 | T36, T47, T49, T66 |
| T55 | T1, T60, T61, T75 |
| T56 | T2, T57, T59, T63 |
| T57 | T39, T45, T56, T61 |
| T58 | T4, T62, T63, T75 |
| T59 | T5, T34, T56, T62 |
| T60 | T6, T35, T55, T62 |
| T61 | T7, T32, T55, T57 |
| T62 | T33, T58, T59, T60 |
| T63 | T9, T39, T56, T58 |
| T64 | T10, T69, T70, T76 |
| T65 | T11, T66, T68, T72 |
| T66 | T48, T54, T65, T70 |
| T67 | T13, T71, T72, T76 |
| T68 | T14, T25, T65, T71 |
| T69 | T15, T26, T64, T71 |
| T70 | T16, T23, T64, T66 |
| T71 | T24, T67, T68, T69 |
| T72 | T18, T48, T65, T67 |
| T73 | T1, T4, T19, T22 |
| T74 | T10, T13, T28, T31 |
| T75 | T37, T40, T55, T58 |
| T76 | T46, T49, T64, T67. |

Embodiment 13

A method for separating fluids, comprising: exposing an input fluid stream comprising a first fluid component and a second fluid component to a membrane comprising particles of crystalline zeolite ITQ-55 to form a permeate product fluid stream and a rejection product fluid stream, a molar ratio of the first fluid component to the second fluid component in the permeate product fluid stream being greater than a ratio of the first fluid component to the second fluid component in the input fluid stream, a molar ratio of the first fluid component to the second fluid component in the rejection product fluid stream being less than a ratio of the first fluid component to the second fluid component in the input fluid stream, wherein the zeolite ITQ-55, as synthesized, has an X-ray diffraction pattern with, at least, the angle values $2\theta$ (degrees) and relative intensities $(I/I_0)$:

| $2\theta$ (degrees) ± 0.5 | Intensity $(I/I_0)$ |
|---|---|
| 5.8 | w |
| 7.7 | w |
| 8.9 | w |
| 9.3 | mf |
| 9.9 | w |
| 10.1 | w |
| 13.2 | m |
| 13.4 | w |
| 14.7 | w |
| 15.1 | m |
| 15.4 | w |
| 15.5 | w |
| 17.4 | m |
| 17.7 | m |
| 19.9 | m |
| 20.6 | m |
| 21.2 | f |

-continued

| 2θ (degrees) ± 0.5 | Intensity (I/I$_0$) |
|---|---|
| 21.6 | f |
| 22.0 | f |
| 23.1 | mf |
| 24.4 | m |
| 27.0 | m | where I$_0$ is the intensity from the most intense pick to which is assigned a value of 100
w is a weak relative intensity between 0 and 20%,
m is an average relative intensity between 20 and 40%,
f is a strong relative intensity between 40 and 60%,
and mf is a very strong relative intensity between 60 and 100%.

Embodiment 14

The method of any of Embodiments 12 or 13, wherein the zeolite ITQ-55 has, in calcined state and in absence of defects in its crystalline matrix manifested by the presence of silanols, an empiric formula $$x(M_{1/n}XO_2):yYO_2:gGeO_2:(1-g)SiO_2$$

in which
M is selected between H$^+$, at least one inorganic cation of charge +n, and a mixture of both,
X is at least one chemical element of oxidation state +3,
Y is at least one chemical element with oxidation state +4 different from Si,
x takes a value between 0 and 0.2, both included,
y takes a value between 0 and 0.1, both included,
g takes a value between 0 and 0.5, both included.

Embodiment 15

The method of Embodiment 14, wherein x takes a value of essentially zero, y takes a value of essentially zero, and g takes a value of essentially zero.

Embodiment 16

The method of Embodiment 14, wherein a) x takes a value of greater than zero, b) y takes a value of greater than zero, c) g takes a value of greater than zero, or d) a combination thereof.

Embodiment 17

The method of any of Embodiments 12 to 16, wherein the membrane comprises particles of crystalline zeolite ITQ-55 having a mean particle size of about 20 nm to about 1 micron.

Embodiment 18

The method of any of Embodiments 12 to 17, wherein the particles of crystalline zeolite ITQ-55 comprise a contiguous layer of particles.

Embodiment 19 the method of any of embodiments 12 to 18, wherein the particles of crystalline zeolite ITQ-55 comprise a layer of particles of crystalline zeolite ITQ-55 on a support.

Embodiment 20

The method of Embodiment 19, wherein the support comprises glass, fused quartz, silica, silicon, clay, metal, porous glass, sintered porous metal, titania, cordierite, or a combination thereof.

Embodiment 21

The method of any of Embodiments 19 or 20, wherein the supported layer of particles of crystalline zeolite ITQ-55 comprises particles of crystalline zeolite ITQ-55 in a particulate matrix, a pore structure being defined by the interstices between the particles, between the crystals, and between the particles and the crystals.

Embodiment 22

The method of any of Embodiments 12 to 21, wherein the membrane comprises at least one of a hybrid layer and a composite layer.

Embodiment 23

The method of any of Embodiments 12 to 22, further comprising exposing a permeate side of the membrane to a sweep stream.

Embodiment 24

The method of any of the above embodiments, wherein the second fluid component is methane, ethane, methanol, dimethyl ether, an organic compound containing 3 or more heavy atoms, or a combination thereof.

Embodiment 25

The method of Embodiment 24, wherein the first fluid component is CO, CO$_2$, H$_2$, H$_2$O, or a combination thereof.

Embodiment 26

The method of Embodiment 25, wherein the first fluid component is CO$_2$ and the second fluid component is CH$_4$.

Embodiment 27

The method of Embodiment 26, wherein the input fluid stream comprises natural gas.

Embodiment 28

The method of Embodiment 24, wherein the first fluid component is ethylene, acetylene, formaldehyde, or a combination thereof.

Embodiment 29

The method of Embodiment 24, wherein the first fluid component is H$_2$S, NH$_3$, or a combination thereof.

Embodiment 30

The method of Embodiment 24, wherein the first fluid component is SO$_2$, N$_2$O, NO, NO$_2$, a sulfur oxide, or a combination thereof, the input fluid optionally comprising a flue gas.

Embodiment 31

The method of Embodiment 24, wherein the first fluid component is $N_2$, the input fluid stream optionally comprising a natural gas stream.

Embodiment 32

The method of Embodiment 31, wherein the input fluid stream is exposed to the adsorbent at a temperature of about 223 K to about 523 K, optionally at least about 270 K.

Embodiment 33

The method of Embodiment 24, wherein the first fluid component is a noble gas, a molecular halogen, a halogen hydride, or a combination thereof.

Embodiment 34

The method of any of the above embodiments, wherein the first fluid component is methane, ethylene, ethane, methanol, dimethyl ether, or a combination thereof.

Embodiment 35

The method of any of the above embodiments, wherein the second fluid component is nitrogen, the first fluid component being hydrogen, a noble gas, oxygen, a nitrogen oxide, $CO_2$, CO, a molecular halogen, a halogen hydride, or a combination thereof.

Embodiment 36

The method of Embodiment 35, wherein the first fluid component is $CO_2$.

Embodiment 37

The method of Embodiment 36, wherein the input fluid stream comprises a flue gas.

Embodiment 38

The method of Embodiment 35, wherein the first fluid component is $O_2$.

Embodiment 39

The method of Embodiment 26, wherein the input fluid stream comprises air.

Embodiment 40

The method of Embodiment 35, wherein the molecular halogen or the halogen halide comprise F, Cl, Br, or a combination thereof as the halogen.

Embodiment 41

The method of any of the above embodiments, wherein the first fluid component is $CO_2$ and the second fluid component comprises one or more hydrocarbons.

Embodiment 42

The method of Embodiment 29, wherein the one or more hydrocarbons are methane, ethane, ethylene, or a combination thereof.

Embodiment 43

The method of any of the above embodiments, wherein the first fluid component is ethylene and the second fluid component is ethane, methane, or a combination thereof.

Embodiment 44

The method of any of the above embodiments, wherein the first fluid component is a nitrogen oxide and the second fluid component is a sulfur oxide.

Embodiment 45

The method of any of the above embodiments, wherein the first fluid component is $H_2$ and the second fluid component is a nitrogen oxide, a sulfur oxide, a hydrocarbon, a carbon oxide, or a combination thereof, the input fluid stream optionally comprising syngas.

Embodiment 46

The method of any of the above embodiments, wherein the first fluid component is $H_2$ and the second fluid component is $H_2S$, $NH_3$, or a combination thereof.

Embodiment 47

The method of any of the above embodiments, wherein the first fluid component is $H_2O$ and the second fluid component is $H_2$.

Embodiment 48

The method of any of the above embodiments, wherein the first fluid component is He, Ne, Ar. Kr, and the second fluid component is $N_2$, $H_2O$, CO, $CO_2$, a hydrocarbon, or a combination thereof.

Embodiment 49

The method of any of the above embodiments, wherein the first fluid component is methanol, dimethyl ether, or a combination thereof.

Embodiment 50

The method of any of the above embodiments, wherein the second fluid component is methanol, dimethyl ether, or a combination thereof.

Embodiment 51

The method of any of the above embodiments, wherein the first fluid component is acetylene and the second fluid component is ethylene, methane, ethane, or a combination thereof.

Embodiment 52

The method of Embodiments 8 or 9, wherein the input fluid stream comprises natural gas.

Embodiment 53

The method of Embodiment 52, wherein the input fluid stream is exposed to the adsorbent comprising zeolite ITQ-55 at a pressure of about 5 psia (about 0.03 MPa) to about 5000 psia (about 35 MPa), optionally at least about 250 psia (about 1.7 MPa), or at least about 500 psia (about 3.4 MPa), or at least about 1000 psia (about 6.9 MPa).

Embodiment 54

The method of any of Embodiments 52 to 53, wherein the input fluid stream is exposed to the adsorbent at a temperature of about −18° C. to about 399° C., or about 316° C. or less, or about 260° C. or less.

Embodiment 55

The method of any of Embodiments 52 to 54, wherein the first fluid component is $N_2$, $H_2O$, $CO_2$, or a combination thereof.

Embodiment 56

The method of any of Embodiments 52 to 54, wherein the first fluid component is at least one of $N_2$ and $H_2O$.

Embodiment 57

The method of any of Embodiments 52 to 54, wherein the first fluid component is $N_2$.

Embodiment 58

The method of any of Embodiments 52 to 54, wherein the first fluid component is $H_2O$.

Embodiment 59

The method of any of Embodiments 52 to 58, wherein the second fluid component is $CH_4$, a hydrocarbon having a higher molecular weight than $CH_4$, or a combination thereof.

ADDITIONAL STORAGE EMBODIMENTS

Embodiment 1

A method for adsorbing and storing fluids, comprising: exposing an input fluid stream comprising a first fluid component to an adsorbent comprising zeolite ITQ-55 at a first pressure and a first temperature; maintaining the adsorbent at a second pressure and a second temperature for a storage period of time; forming an adsorbed product fluid stream comprising the first fluid component; and collecting the adsorbed product stream, wherein the tetrahedral atom is defined by connecting the nearest T atoms in the manner described in the following Table:

| ITQ-55 tetrahedral atom interconnections | |
|---|---|
| T atom | Connected to: |
| T1 | T6, T7, T55, T73 |
| T2 | T3, T5, T9, T56 |
| T3 | T2, T7, T21, T27 |
| T4 | T8, T9, T58, T73 |
| T5 | T2, T8, T52, T59 |
| T6 | T1, T8, T53, T60 |
| T7 | T1, T3, T50, T61 |
| T8 | T4, T5, T6, T51 |
| T9 | T2, T4, T21, T63 |
| T10 | T15, T16, T64, T74 |
| T11 | T12, T14, T18, T65 |
| T12 | T11, T16, T30, T36 |
| T13 | T17, T18, T67, T74 |
| T14 | T11, T17, T43, T68 |
| T15 | T10, T17, T44, T69 |
| T16 | T10, T12, T41, T70 |
| T17 | T13, T14, T15, T42 |
| T18 | T11, T13, T30, T72 |
| T19 | T24, T25, T37, T73 |
| T20 | T21, T23, T27, T38 |
| T21 | T3, T9, T20, T25 |
| T22 | T26, T27, T40, T73 |
| T23 | T20, T26, T41, T70 |
| T24 | T19, T26, T42, T71 |
| T25 | T19, T21, T43, T68 |
| T26 | T22, T23, T24, T69 |
| T27 | T3, T20, T22, T45 |
| T28 | T33, T34, T46, T74 |
| T29 | T30, T32, T36, T47 |
| T30 | T12, T18, T29, T34 |
| T31 | T35, T36, T49, T74 |
| T32 | T29, T35, T50, T61 |
| T33 | T28, T35, T51, T62 |
| T34 | T28, T30, T52, T59 |
| T35 | T31, T32, T33, T60 |
| T36 | T12, T29, T31, T54 |
| T37 | T19, T42, T43, T75 |
| T38 | T20, T39, T41, T45 |
| T39 | T38, T43, T57, T63 |
| T40 | T22, T44, T45, T75 |
| T41 | T16, T23, T38, T44 |
| T42 | T17, T24, T37, T44 |
| T43 | T14, T25, T37, T39 |
| T44 | T15, T40, T41, T42 |
| T45 | T27, T38, T40, T57 |
| T46 | T28, T51, T52, T76 |
| T47 | T29, T48, T50, T54 |
| T48 | T47, T52, T66, T72 |
| T49 | T31, T53, T54, T76 |
| T50 | T7, T32, T47, T53 |
| T51 | T8, T33, T46, T53 |
| T52 | T5, T34, T46, T48 |
| T53 | T6, T49, T50, T51 |
| T54 | T36, T47, T49, T66 |
| T55 | T1, T60, T61, T75 |
| T56 | T2, T57, T59, T63 |
| T57 | T39, T45, T56, T61 |
| T58 | T4, T62, T63, T75 |
| T59 | T5, T34, T56, T62 |
| T60 | T6, T35, T55, T62 |
| T61 | T7, T32, T55, T57 |
| T62 | T33, T58, T59, T60 |
| T63 | T9, T39, T56, T58 |
| T64 | T10, T69, T70, T76 |
| T65 | T11, T66, T68, T72 |
| T66 | T48, T54, T65, T70 |
| T67 | T13, T71, T72, T76 |
| T68 | T14, T25, T65, T71 |
| T69 | T15, T26, T64, T71 |
| T70 | T16, T23, T64, T66 |
| T71 | T24, T67, T68, T69 |
| T72 | T18, T48, T65, T67 |
| T73 | T1, T4, T19, T22 |
| T74 | T10, T13, T28, T31 |
| T75 | T37, T40, T55, T58 |
| T76 | T46, T49, T64, T67. |

Embodiment 2

A method for adsorbing and storing fluids, comprising: exposing an input fluid stream comprising a first fluid component to an adsorbent comprising zeolite ITQ-55 at a first pressure and a first temperature; maintaining the adsorbent at a second pressure and a second temperature for a storage period of time; forming an adsorbed product fluid stream comprising the first fluid component; and collecting the adsorbed product stream, wherein the zeolite ITQ-55, as synthesized, has an X-ray diffraction pattern with, at least, the angle values 2θ (degrees) and relative intensities ($I/I_0$):

| 2θ (degrees) ± 0.5 | Intensity ($I/I_0$) |
|---|---|
| 5.8 | w |
| 7.7 | w |
| 8.9 | w |
| 9.3 | mf |
| 9.9 | w |
| 10.1 | w |
| 13.2 | m |
| 13.4 | w |
| 14.7 | w |
| 15.1 | m |
| 15.4 | w |
| 15.5 | w |
| 17.4 | m |
| 17.7 | m |
| 19.9 | m |
| 20.6 | m |
| 21.2 | f |
| 21.6 | f |
| 22.0 | f |
| 23.1 | mf |
| 24.4 | m |
| 27.0 | m | where $I_0$ is the intensity from the most intense pick to which is assigned a value of 100
w is a weak relative intensity between 0 and 20%,
m is an average relative intensity between 20 and 40%,
f is a strong relative intensity between 40 and 60%,
and mf is a very strong relative intensity between 60 and 100%.

Embodiment 3

The method of any of the above embodiments, wherein the zeolite ITQ-55 has, in calcined state and in absence of defects in its crystalline matrix manifested by the presence of silanols, an empiric formula $$x(M_{1/n}XO_2):yYO_2:gGeO_2:(1-g)SiO_2$$

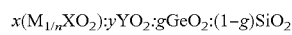

in which
M is selected between $H^+$, at least one inorganic cation of charge +n, and a mixture of both,
X is at least one chemical element of oxidation state +3,
Y is at least one chemical element with oxidation state +4 different from Si,
x takes a value between 0 and 0.2, both included,
y takes a value between 0 and 0.1, both included,
g takes a value between 0 and 0.5, both included.

Embodiment 4

The method of Embodiment 3, wherein x takes a value of essentially zero, y takes a value of essentially zero, and g takes a value of essentially zero.

Embodiment 5

The method of Embodiment 3, wherein a) x takes a value of greater than zero, b) y takes a value of greater than zero, c) g takes a value of greater than zero, or d) a combination thereof.

Embodiment 6

The method of any of the above embodiments, wherein exposing the input fluid stream to an adsorbent comprises exposing the input fluid stream to an adsorbent in a swing adsorption vessel.

Embodiment 7

The method of any of the above embodiments, wherein the first temperature and the second temperature are the same, wherein the first pressure and the second pressure are the same, or a combination thereof.

Embodiment 8

The method of any of the above embodiments, wherein forming an adsorbed product fluid stream comprises modifying the second temperature of the adsorbent.

Embodiment 9

The method of any of the above embodiments, wherein forming an adsorbed product fluid stream comprises exposing a fluid stream comprising a third component to the adsorbent comprising zeolite ITQ-55, at least a portion of the third component being adsorbed by the adsorbent comprising zeolite ITQ-55.

Embodiment 10

The method of any of the above embodiments, wherein the adsorbent has less than about 20% of open pore volume in pores having diameters greater than about 20 Angstroms and less than about 1 micron.

Embodiment 11

The method of any of the above embodiments, wherein maintaining the adsorbent at a second pressure and a second temperature for a storage period of time comprises exposing the adsorbent to an environment having a partial pressure of the first fluid component of about 0.1 MPaa or less.

Embodiment 12

The method of any of the above embodiments, wherein the input fluid stream further comprises a second component, a molar ratio of the first component to the second component in the adsorbed product stream is greater than a molar ratio of the first component to the second component in the input fluid stream.

Embodiment 13

The method of Embodiment 12, wherein the second fluid component is methane, ethane, methanol, dimethyl ether, an organic compound containing 3 or more heavy atoms, or a combination thereof.

Embodiment 14

The method of Embodiment 12, wherein the first fluid component is $H_2$ and the second fluid component is a nitrogen oxide, a sulfur oxide, a hydrocarbon, a carbon oxide, or a combination thereof, the input fluid stream optionally comprising syngas.

Embodiment 15

The method of Embodiment 12, wherein the first fluid component is $H_2$ and the second fluid component is $H_2S$, $NH_3$, or a combination thereof.

Embodiment 16

The method of any of the above embodiments, wherein the first fluid component is $CO_2$, $H_2$, or a combination thereof.

Embodiment 17

The method of any of the above embodiments, wherein the first fluid component is ethylene, acetylene, formaldehyde, or a combination thereof.

Embodiment 18

The method of any of the above embodiments, wherein the first fluid component is a noble gas, a molecular halogen, a halogen hydride, or a combination thereof.

Embodiment 19

The method of any of the above embodiments, wherein the first fluid component is methane, ethylene, ethane, methanol, dimethyl ether, or a combination thereof.

ADDITIONAL CATALYSIS EMBODIMENTS

Embodiment 1

A method for converting organic compounds, comprising: exposing an input fluid stream comprising an organic compound to a catalyst comprising zeolite ITQ-55 under effective conversion conditions to form a converted organic compound, the conversion being catalyzed by the catalyst comprising zeolite ITQ-55, wherein the tetrahedral atom is defined by connecting the nearest T atoms in the manner described in the following Table:

| ITQ-55 tetrahedral atom interconnections | |
|---|---|
| T atom | Connected to: |
| T1 | T6, T7, T55, T73 |
| T2 | T3, T5, T9, T56 |
| T3 | T2, T7, T21, T27 |
| T4 | T8, T9, T58, T73 |
| T5 | T2, T8, T52, T59 |
| T6 | T1, T8, T53, T60 |
| T7 | T1, T3, T50, T61 |
| T8 | T4, T5, T6, T51 |
| T9 | T2, T4, T21, T63 |
| T10 | T15, T16, T64, T74 |
| T11 | T12, T14, T18, T65 |
| T12 | T11, T16, T30, T36 |
| T13 | T17, T18, T67, T74 |
| T14 | T11, T17, T43, T68 |
| T15 | T10, T17, T44, T69 |
| T16 | T10, T12, T41, T70 |
| T17 | T13, T14, T15, T42 |
| T18 | T11, T13, T30, T72 |
| T19 | T24, T25, T37, T73 |
| T20 | T21, T23, T27, T38 |
| T21 | T3, T9, T20, T25 |
| T22 | T26, T27, T40, T73 |
| T23 | T20, T26, T41, T70 |
| T24 | T19, T26, T42, T71 |
| T25 | T19, T21, T43, T68 |
| T26 | T22, T23, T24, T69 |
| T27 | T3, T20, T22, T45 |
| T28 | T33, T34, T46, T74 |
| T29 | T30, T32, T36, T47 |
| T30 | T12, T18, T29, T34 |
| T31 | T35, T36, T49, T74 |
| T32 | T29, T35, T50, T61 |
| T33 | T28, T35, T51, T62 |
| T34 | T28, T30, T52, T59 |
| T35 | T31, T32, T33, T60 |
| T36 | T12, T29, T31, T54 |
| T37 | T19, T42, T43, T75 |
| T38 | T20, T39, T41, T45 |
| T39 | T38, T43, T57, T63 |
| T40 | T22, T44, T45, T75 |
| T41 | T16, T23, T38, T44 |
| T42 | T17, T24, T37, T44 |
| T43 | T14, T25, T37, T39 |
| T44 | T15, T40, T41, T42 |
| T45 | T27, T38, T40, T57 |
| T46 | T28, T51, T52, T76 |
| T47 | T29, T48, T50, T54 |
| T48 | T47, T52, T66, T72 |
| T49 | T31, T53, T54, T76 |
| T50 | T7, T32, T47, T53 |
| T51 | T8, T33, T46, T53 |
| T52 | T5, T34, T46, T48 |
| T53 | T6, T49, T50, T51 |
| T54 | T36, T47, T49, T66 |
| T55 | T1, T60, T61, T75 |
| T56 | T2, T57, T59, T63 |
| T57 | T39, T45, T56, T61 |
| T58 | T4, T62, T63, T75 |
| T59 | T5, T34, T56, T62 |
| T60 | T6, T35, T55, T62 |
| T61 | T7, T32, T55, T57 |
| T62 | T33, T58, T59, T60 |
| T63 | T9, T39, T56, T58 |
| T64 | T10, T69, T70, T76 |
| T65 | T11, T66, T68, T72 |
| T66 | T48, T54, T65, T70 |
| T67 | T13, T71, T72, T76 |
| T68 | T14, T25, T65, T71 |
| T69 | T15, T26, T64, T71 |
| T70 | T16, T23, T64, T66 |
| T71 | T24, T67, T68, T69 |
| T72 | T18, T48, T65, T67 |
| T73 | T1, T4, T19, T22 |
| T74 | T10, T13, T28, T31 |
| T75 | T37, T40, T55, T58 |
| T76 | T46, T49, T64, T67. |

Embodiment 2

A method for converting organic compounds, comprising: exposing an input fluid stream comprising an organic compound to a catalyst comprising zeolite ITQ-55 under effective conversion conditions to form a converted organic compound, the conversion being catalyzed by the catalyst comprising zeolite ITQ-55, wherein the zeolite ITQ-55, as synthesized, has an X-ray diffraction pattern with, at least, the angle values 2θ (degrees) and relative intensities ($I/I_0$):

| 2θ (degrees) ± 0.5 | Intensity (I/I₀) |
| --- | --- |
| 5.8 | w |
| 7.7 | w |
| 8.9 | w |
| 9.3 | mf |
| 9.9 | w |
| 10.1 | w |
| 13.2 | m |
| 13.4 | w |
| 14.7 | w |
| 15.1 | m |
| 15.4 | w |
| 15.5 | w |
| 17.4 | m |
| 17.7 | m |
| 19.9 | m |
| 20.6 | m |
| 21.2 | f |
| 21.6 | f |
| 22.0 | f |
| 23.1 | mf |
| 24.4 | m |
| 27.0 | m | where $I_0$ is the intensity from the most intense pick to which is assigned a value of 100 w is a weak relative intensity between 0 and 20%, m is an average relative intensity between 20 and 40%, f is a strong relative intensity between 40 and 60%, and mf is a very strong relative intensity between 60 and 100%.

Embodiment 3

The method of any of the above embodiments, wherein the zeolite ITQ-55 has, in calcined state and in absence of defects in its crystalline matrix manifested by the presence of silanols, an empiric formula

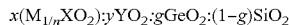

$$x(M_{1/n}XO_2):yYO_2:gGeO_2:(1-g)SiO_2$$

in which

M is selected between H⁺, at least one inorganic cation of charge +n, and a mixture of both, X is at least one chemical element of oxidation state +3, Y is at least one chemical element with oxidation state +4 different from Si, x takes a value between 0 and 0.2, both included, y takes a value between 0 and 0.1, both included, g takes a value between 0 and 0.5, both included.

Embodiment 4

The method of Embodiment 3, wherein x takes a value of essentially zero, y takes a value of essentially zero, and g takes a value of essentially zero.

Embodiment 5

The method of Embodiment 3, wherein X is selected from Al, Ga, B, Fe, Cr, and combinations thereof, y takes the value 0, and g takes the value 0.

Embodiment 6

The method of Embodiment 5, wherein the zeolite ITQ-55 comprises Si, O, and Al.

Embodiment 7

The method of Embodiment 6, wherein a ratio of Si to Al is from about 10:1 to about 1000:1, optionally at least about 100:1.

Embodiment 8

The method of any of the above embodiments, wherein exposing the input fluid stream to the catalyst comprising zeolite ITQ-55 comprises exposing the input fluid stream to catalyst particles comprising zeolite ITQ-55.

Embodiment 9

The method of Embodiment 8, wherein the input fluid stream is exposed to the catalyst particles comprising zeolite ITQ-55 in a fluidized bed reactor or a riser reactor.

Embodiment 10

The method of any of Embodiments 8 or 9, wherein the catalyst particles comprising zeolite ITQ-55 further comprise a support, the support comprising silica, alumina, silica-alumina, zirconia, titania, or a combination thereof.

Embodiment 11

The method of any of Embodiments 8 to 10, wherein the catalyst particles comprise a Group VI metal, a Group VIII metal, or a combination thereof.

Embodiment 12

The method of any of Embodiments 8 or 11, wherein the catalyst particles further comprise a zeolite having a framework structure different from zeolite ITQ-55.

Embodiment 13

The method of Embodiment 12, wherein the zeolite having a framework structure different from zeolite ITQ-55 comprises a zeolite having a framework structure of MFI or FAU.

Embodiment 14

The method of any of the above embodiments, wherein the converted organic compound has a higher molecular weight than the organic compound, or wherein the converted organic compound has a lower molecular weight than the organic compound.

Embodiment 15

The method of any of the above embodiments, wherein the organic compound comprises methanol, methane, dimethyl ether, ethylene, acetylene, or a combination thereof.

Embodiment 16

The method of Embodiment 15, wherein the input feed further comprises $O_2$, $H_2O$, or a combination thereof.

Embodiment 17

The method of any of Embodiments 15 or 16, wherein the converted organic compound comprises ethylene.

81

Embodiment 18

The method of any of the above embodiments, wherein the organic compound comprises methanol and the converted organic compound comprises dimethyl ether.

Embodiment 19

The method of any of the above embodiments, wherein the organic compound comprises methanol and the converted organic compound comprises an olefin.

Embodiment 20

The method of any of the above embodiments, wherein the organic compound comprises methanol and the converted organic compound comprises a $C_6$-$C_{11}$ aromatic.

Embodiment 21

The method of any of the above embodiments, wherein the organic compound comprises methane and the converted organic compound comprises an alcohol, an olefin, a $C_6$-$C_1$ aromatic, or a combination thereof.

Embodiment 22

The method of any of the above embodiments, wherein the input feed is exposed to the catalyst comprising ITQ-55 in the presence of hydrogen.

Embodiment 23

The method of Embodiment 22, wherein organic compound comprises a sulfur-containing compound and the converted organic compound comprises a desulfurized organic compound.

Embodiment 24

The method of any of the above embodiments, wherein exposing the input fluid to the catalyst comprising zeolite ITQ-55 comprises: exposing the input fluid to the catalyst at conditions comprising a first temperature and a first pressure; and modifying the conditions to a second temperature and a second pressure to expose at least a portion of the input fluid to the catalyst at a second temperature and a second pressure, a diffusion rate of the organic compound at the second temperature and the second pressure being about 50% or less of the diffusion rate at the first temperature and the first pressure, or about 40% or less, or about 30% or less, or about 20% or less, or about 10% or less.

Embodiment 25

The method of Embodiment 24, wherein the second temperature is the same as the first temperature.

Embodiment 26

The method of Embodiment 24, wherein the second temperature is lower than the first temperature.

Embodiment 27

The method of any of Embodiments 24 to 26, wherein the first pressure is at least about 100 bar (10 MPaa) and the second pressure is about 50 bar (5 MPaa) or less.

82

ADDITIONAL COMMON EMBODIMENTS

The following Embodiments are suitable for combination with any of the Additional Separation Embodiments, Additional Storage Embodiments, or Additional Catalysis Embodiments described above.

Embodiment 1

The method of any of the above Additional Separation Embodiments, Additional Storage Embodiments, and/or Additional Catalysis Embodiments, wherein the zeolite ITQ-55, as synthesized, has an X-ray diffraction pattern with, at least, the angle values 2θ (degrees) and relative intensities ($I/I_0$):

| 2θ (degrees) ± 0.5 | Intensity ($I/I_0$) |
|---|---|
| 5.8 | w |
| 7.7 | w |
| 8.9 | w |
| 9.3 | mf |
| 9.9 | w |
| 10.1 | w |
| 13.2 | m |
| 13.4 | w |
| 14.7 | w |
| 15.1 | m |
| 15.4 | w |
| 15.5 | w |
| 17.4 | m |
| 17.7 | m |
| 19.9 | m |
| 20.6 | m |
| 21.2 | f |
| 21.6 | f |
| 22.0 | f |
| 23.1 | mf |
| 24.4 | m |
| 27.0 | m | where $I_0$ is the intensity from the most intense pick to which is assigned a value of 100 w is a weak relative intensity between 0 and 20%,
m is an average relative intensity between 20 and 40%,
f is a strong relative intensity between 40 and 60%,
and mf is a very strong relative intensity between 60 and 100%.

Embodiment 2

The method of any of the above Additional Separation Embodiments, Additional Storage Embodiments, Additional Catalysis Embodiments, and/or Additional Common Embodiment 1, wherein the ITQ-55 has a framework of tetrahedral (T) atoms connected by bridging atoms, wherein the tetrahedral atom is defined by connecting the nearest T atoms in the manner described in the following Table:

| ITQ-55 tetrahedral atom interconnections | |
|---|---|
| T atom | Connected to: |
| T1 | T6, T7, T55, T73 |
| T2 | T3, T5, T9, T56 |
| T3 | T2, T7, T21, T27 |
| T4 | T8, T9, T58, T73 |
| T5 | T2, T8, T52, T59 |
| T6 | T1, T8, T53, T60 |
| T7 | T1, T3, T50, T61 |
| T8 | T4, T5, T6, T51 |
| T9 | T2, T4, T21, T63 |
| T10 | T15, T16, T64, T74 |

ITQ-55 tetrahedral atom interconnections

| T atom | Connected to: |
|---|---|
| T11 | T12, T14, T18, T65 |
| T12 | T11, T16, T30, T36 |
| T13 | T17, T18, T67, T74 |
| T14 | T11, T17, T43, T68 |
| T15 | T10, T17, T44, T69 |
| T16 | T10, T12, T41, T70 |
| T17 | T13, T14, T15, T42 |
| T18 | T11, T13, T30, T72 |
| T19 | T24, T25, T37, T73 |
| T20 | T21, T23, T27, T38 |
| T21 | T3, T9, T20, T25 |
| T22 | T26, T27, T40, T73 |
| T23 | T20, T26, T41, T70 |
| T24 | T19, T26, T42, T71 |
| T25 | T19, T21, T43, T68 |
| T26 | T22, T23, T24, T69 |
| T27 | T3, T20, T22, T45 |
| T28 | T33, T34, T46, T74 |
| T29 | T30, T32, T36, T47 |
| T30 | T12, T18, T29, T34 |
| T31 | T35, T36, T49, T74 |
| T32 | T29, T35, T50, T61 |
| T33 | T28, T35, T51, T62 |
| T34 | T28, T30, T52, T59 |
| T35 | T31, T32, T33, T60 |
| T36 | T12, T29, T31, T54 |
| T37 | T19, T42, T43, T75 |
| T38 | T20, T39, T41, T45 |
| T39 | T38, T43, T57, T63 |
| T40 | T22, T44, T45, T75 |
| T41 | T16, T23, T38, T44 |
| T42 | T17, T24, T37, T44 |
| T43 | T14, T25, T37, T39 |
| T44 | T15, T40, T41, T42 |
| T45 | T27, T38, T40, T57 |
| T46 | T28, T51, T52, T76 |
| T47 | T29, T48, T50, T54 |
| T48 | T47, T52, T66, T72 |
| T49 | T31, T53, T54, T76 |
| T50 | T7, T32, T47, T53 |
| T51 | T8, T33, T46, T53 |
| T52 | T5, T34, T46, T48 |
| T53 | T6, T49, T50, T51 |
| T54 | T36, T47, T49, T66 |
| T55 | T1, T60, T61, T75 |
| T56 | T2, T57, T59, T63 |
| T57 | T39, T45, T56, T61 |
| T58 | T4, T62, T63, T75 |
| T59 | T5, T34, T56, T62 |
| T60 | T6, T35, T55, T62 |
| T61 | T7, T32, T55, T57 |
| T62 | T33, T58, T59, T60 |
| T63 | T9, T39, T56, T58 |
| T64 | T10, T69, T70, T76 |
| T65 | T11, T66, T68, T72 |
| T66 | T48, T54, T65, T70 |
| T67 | T13, T71, T72, T76 |
| T68 | T14, T25, T65, T71 |
| T69 | T15, T26, T64, T71 |
| T70 | T16, T23, T64, T66 |
| T71 | T24, T67, T68, T69 |
| T72 | T18, T48, T65, T67 |
| T73 | T1, T4, T19, T22 |
| T74 | T10, T13, T28, T31 |
| T75 | T37, T40, T55, T58 |
| T76 | T46, T49, T64, T67. |

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

What is claimed is:

1. A method for separating fluids, comprising:
    exposing an input fluid stream comprising a first fluid component and a second fluid component to an adsorbent comprising zeolite ITQ-55 to form a rejection product fluid stream, a molar ratio of the first fluid component to the second fluid component in the rejection product fluid stream being less than a molar ratio of the first fluid component to the second fluid component in the input fluid stream;
    collecting the rejection product fluid stream;
    forming an adsorbed product fluid stream, a molar ratio of the first fluid component to the second fluid component in the adsorbed product stream being greater than the molar ratio of the first fluid component to the second fluid component in the input fluid stream; and
    collecting the adsorbed product stream,
    wherein the zeolite ITQ-55 has a framework of tetrahedral (T) atoms connected by bridging atoms, wherein the tetrahedral atom is defined by connecting the nearest T atoms in the manner described in the following Table:

ITQ-55 tetrahedral atom interconnections

| T atom | Connected to: |
|---|---|
| T1 | T6, T7, T55, T73 |
| T2 | T3, T5, T9, T56 |
| T3 | T2, T7, T21, T27 |
| T4 | T8, T9, T58, T73 |
| T5 | T2, T8, T52, T59 |
| T6 | T1, T8, T53, T60 |
| T7 | T1, T3, T50, T61 |
| T8 | T4, T5, T6, T51 |
| T9 | T2, T4, T21, T63 |
| T10 | T15, T16, T64, T74 |
| T11 | T12, T14, T18, T65 |
| T12 | T11, T16, T30, T36 |
| T13 | T17, T18, T67, T74 |
| T14 | T11, T17, T43, T68 |
| T15 | T10, T17, T44, T69 |
| T16 | T10, T12, T41, T70 |
| T17 | T13, T14, T15, T42 |
| T18 | T11, T13, T30, T72 |
| T19 | T24, T25, T37, T73 |
| T20 | T21, T23, T27, T38 |
| T21 | T3, T9, T20, T25 |
| T22 | T26, T27, T40, T73 |
| T23 | T20, T26, T41, T70 |
| T24 | T19, T26, T42, T71 |
| T25 | T19, T21, T43, T68 |
| T26 | T22, T23, T24, T69 |
| T27 | T3, T20, T22, T45 |
| T28 | T33, T34, T46, T74 |
| T29 | T30, T32, T36, T47 |
| T30 | T12, T18, T29, T34 |
| T31 | T35, T36, T49, T74 |
| T32 | T29, T35, T50, T61 |
| T33 | T28, T35, T51, T62 |

-continued

ITQ-55 tetrahedral atom interconnections

| T atom | Connected to: |
|---|---|
| T34 | T28, T30, T52, T59 |
| T35 | T31, T32, T33, T60 |
| T36 | T12, T29, T31, T54 |
| T37 | T19, T42, T43, T75 |
| T38 | T20, T39, T41, T45 |
| T39 | T38, T43, T57, T63 |
| T40 | T22, T44, T45, T75 |
| T41 | T16, T23, T38, T44 |
| T42 | T17, T24, T37, T44 |
| T43 | T14, T25, T37, T39 |
| T44 | T15, T40, T41, T42 |
| T45 | T27, T38, T40, T57 |
| T46 | T28, T51, T52, T76 |
| T47 | T29, T48, T50, T54 |
| T48 | T47, T52, T66, T72 |
| T49 | T31, T53, T54, T76 |
| T50 | T7, T32, T47, T53 |
| T51 | T8, T33, T46, T53 |
| T52 | T5, T34, T46, T48 |
| T53 | T6, T49, T50, T51 |
| T54 | T36, T47, T49, T66 |
| T55 | T1, T60, T61, T75 |
| T56 | T2, T57, T59, T63 |
| T57 | T39, T45, T56, T61 |
| T58 | T4, T62, T63, T75 |
| T59 | T5, T34, T56, T62 |
| T60 | T6, T35, T55, T62 |
| T61 | T7, T32, T55, T57 |
| T62 | T33, T58, T59, T60 |
| T63 | T9, T39, T56, T58 |
| T64 | T10, T69, T70, T76 |
| T65 | T11, T66, T68, T72 |
| T66 | T48, T54, T65, T70 |
| T67 | T13, T71, T72, T76 |
| T68 | T14, T25, T65, T71 |
| T69 | T15, T26, T64, T71 |
| T70 | T16, T23, T64, T66 |
| T71 | T24, T67, T68, T69 |
| T72 | T18, T48, T65, T67 |
| T73 | T1, T4, T19, T22 |
| T74 | T10, T13, T28, T31 |
| T75 | T37, T40, T55, T58 |
| T76 | T46, T49, T64, T67. |

2. The method of claim 1, wherein the zeolite ITQ-55 has, in calcined state and in absence of defects in its crystalline matrix manifested by the presence of silanols, an empiric formula

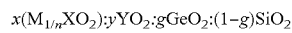
$x(M_{1/n}XO_2):yYO_2:gGeO_2:(1-g)SiO_2$ in which

M is selected between H⁺, at least one inorganic cation of charge +n, and a mixture of both, X is at least one chemical element of oxidation state +3, Y is at least one chemical element with oxidation state +4 different from Si, x takes a value between 0 and 0.2, both included, y takes a value between 0 and 0.1, both included, g takes a value between 0 and 0.5, both included.

3. The method of claim 2, wherein x takes a value of essentially zero, y takes a value of essentially zero, and g takes a value of essentially zero.

4. The method of claim 2, wherein a) x takes a value of greater than zero, b) y takes a value of greater than zero, c) g takes a value of greater than zero, or d) a combination thereof.

5. The method of claim 1, wherein forming an adsorbed product fluid stream comprises modifying at least one of a temperature or a pressure of the adsorbent.

6. The method of claim 1, wherein forming an adsorbed product fluid stream comprises exposing a fluid stream comprising a third component to the adsorbent comprising zeolite ITQ-55, at least a portion of the third component being adsorbed by the adsorbent comprising zeolite ITQ-55.

7. The method of claim 1, wherein exposing the input fluid stream to an adsorbent comprises exposing the input fluid stream to an adsorbent in a swing adsorption vessel.

8. The method of claim 7, wherein exposing the input fluid stream to an adsorbent comprises exposing the input fluid stream to the adsorbent under pressure swing adsorption conditions, temperature swing adsorption conditions, rapid cycle pressure swing adsorption conditions, or a combination thereof.

9. The method of claim 7, wherein the input fluid stream comprises natural gas.

10. The method of claim 9, wherein the input fluid stream is exposed to the adsorbent comprising zeolite ITQ-55 at a pressure of about 5 psia (about 0.03 MPa) to about 5000 psia (about 35 MPa), optionally at least about 250 psia (about 1.7 MPa), or at least about 500 psia (about 3.4 MPa), or at least about 1000 psia (about 6.9 MPa).

11. The method of claim 9, wherein the input fluid stream is exposed to the adsorbent at a temperature of about −18° C. to about 399° C., or about 316° C. or less, or about 260° C. or less.

12. The method of claim 9, wherein the first fluid component is $N_2$, $H_2O$, $CO_2$, or a combination thereof.

13. The method of claim 9, wherein the first fluid component is at least one of $N_2$ and $H_2O$.

14. The method of claim 9, wherein the first fluid component is $N_2$.

15. The method of claim 9, wherein the second fluid component is $CH_4$, a hydrocarbon having a higher molecular weight than $CH_4$, or a combination thereof.

16. The method of claim 1, wherein the input fluid stream is exposed to the adsorbent at effective conditions for performing a kinetic separation of the first component from the second component.

17. The method of claim 1, wherein the input fluid stream is exposed to the adsorbent at effective conditions for performing an equilibrium separation of the first component from the second component.

18. The method of claim 1, wherein the adsorbent has less than about 20% of open pore volume in pores having diameters greater than about 20 Angstroms and less than about 1 micron.

19. The method of claim 1, wherein the second fluid component is methane, ethane, methanol, dimethyl ether, an organic compound containing 3 or more heavy atoms, or a combination thereof.

20. The method of claim 19, wherein the first fluid component is CO, $CO_2$, $H_2$, $H_2O$, or a combination thereof.

21. The method of claim 20, wherein the first fluid component is $CO_2$ and the second fluid component is $CH_4$.

22. The method of claim 21, wherein the input fluid stream comprises natural gas.

23. The method of claim 19, wherein the first fluid component is ethylene, acetylene, formaldehyde, or a combination thereof.

24. The method of claim 19, wherein the first fluid component is $H_2S$, $NH_3$, or a combination thereof.

25. The method of claim 19, wherein the first fluid component is $SO_2$, $N_2O$, NO, $NO_2$, a sulfur oxide, or a combination thereof.

26. The method of claim 19, wherein the first fluid component is $N_2$.

27. The method of claim 26, wherein the input fluid stream is exposed to the adsorbent at a temperature of about 223 K to about 523 K.

28. The method of claim 19, wherein the first fluid component is a noble gas, a molecular halogen, a halogen hydride, or a combination thereof.

29. The method of claim 1, wherein the first fluid component is methane, ethylene, ethane, methanol, dimethyl ether, or a combination thereof.

30. The method of claim 1, wherein the second fluid component is nitrogen, the first fluid component being hydrogen, a noble gas, oxygen, a nitrogen oxide, $CO_2$, CO, a molecular halogen, a halogen hydride, or a combination thereof.

31. The method of claim 30, wherein the first fluid component is $CO_2$.

32. The method of claim 31, wherein the input fluid stream comprises a flue gas.

33. The method of claim 30, wherein the first fluid component is $O_2$.

34. The method of claim 33, wherein the input fluid stream comprises air.

35. The method of claim 30, wherein the molecular halogen or the halogen halide comprise F, Cl, Br, or a combination thereof as the halogen.

36. The method of claim 1, wherein the first fluid component is $CO_2$ and the second fluid component comprises one or more hydrocarbons.

37. The method of claim 36, wherein the one or more hydrocarbons are methane, ethane, ethylene, or a combination thereof.

38. The method of claim 1, wherein the first fluid component is ethylene and the second fluid component is ethane, methane, or a combination thereof.

39. The method of claim 1, wherein the first fluid component is a nitrogen oxide and the second fluid component is a sulfur oxide.

40. The method of claim 1, wherein the first fluid component is $H_2$ and the second fluid component is a nitrogen oxide, a sulfur oxide, a hydrocarbon, a carbon oxide, or a combination thereof.

41. The method of claim 1, wherein the first fluid component is $H_2$ and the second fluid component is $H_2S$, $NH_3$, or a combination thereof.

42. The method of claim 1, wherein the first fluid component is $H_2O$ and the second fluid component is $H_2$.

43. The method of claim 1, wherein the first fluid component is He, Ne, Ar, Kr, or a combination thereof and the second fluid component is $N_2$, $H_2O$, CO, $CO_2$, a hydrocarbon, or a combination thereof.

44. The method of claim 1, wherein the first fluid component is methanol, dimethyl ether, or a combination thereof.

45. The method of claim 1, wherein the second fluid component is methanol, dimethyl ether, or a combination thereof.

46. The method of claim 1, wherein the first fluid component is acetylene and the second fluid component is ethylene, methane, ethane, or a combination thereof.

47. A method for separating fluids, comprising:
exposing an input fluid stream comprising a first fluid component and a second fluid component to an adsorbent comprising zeolite ITQ-55 to form a rejection product fluid stream, a molar ratio of the first fluid component to the second fluid component in the rejection product fluid stream being less than a molar ratio of the first fluid component to the second fluid component in the input fluid stream;
collecting the rejection product fluid stream;
forming an adsorbed product fluid stream, a molar ratio of the first fluid component to the second fluid component in the adsorbed product stream being greater than the molar ratio of the first fluid component to the second fluid component in the input fluid stream; and
collecting the adsorbed product stream, wherein the zeolite ITQ-55, as synthesized, has an X-ray diffraction pattern with, at least, the angle values 2θ (degrees) and relative intensities ($I/I_0$):

| 2θ (degrees) ± 0.5 | Intensity ($I/I_0$) |
|---|---|
| 5.8 | w |
| 7.7 | w |
| 8.9 | w |
| 9.3 | mf |
| 9.9 | w |
| 10.1 | w |
| 13.2 | m |
| 13.4 | w |
| 14.7 | w |
| 15.1 | m |
| 15.4 | w |
| 15.5 | w |
| 17.4 | m |
| 17.7 | m |
| 19.9 | m |
| 20.6 | m |
| 21.2 | f |
| 21.6 | f |
| 22.0 | f |
| 23.1 | mf |
| 24.4 | m |
| 27.0 | m | where $I_0$ is the intensity from the most intense pick to which is assigned a value of 100
w is a weak relative intensity between 0 and 20%,
m is an average relative intensity between 20 and 40%,
f is a strong relative intensity between 40 and 60%,
and mf is a very strong relative intensity between 60 and 100%.

* * * * *